United States Patent
Matsunaga et al.

(10) Patent No.: US 11,746,375 B2
(45) Date of Patent: Sep. 5, 2023

(54) PCR VESSEL, PCR VESSEL CONTAINING REAGENT, AND REAGENT CASSETTE

(71) Applicant: YAMATO-ESULON CO., LTD., Yao (JP)

(72) Inventors: Takashi Matsunaga, Yao (JP); Yoshinori Yamaguchi, Toyonaka (JP); Tetsuji Matsunaga, Yao (JP)

(73) Assignee: YAMATO-ESULON CO., LTD., Yao (JP)

( * ) Notice: Subject to any disclaimer, the term of this patent is extended or adjusted under 35 U.S.C. 154(b) by 646 days.

(21) Appl. No.: 16/606,411

(22) PCT Filed: Apr. 10, 2018

(86) PCT No.: PCT/JP2018/015000
§ 371 (c)(1),
(2) Date: Oct. 18, 2019

(87) PCT Pub. No.: WO2018/193905
PCT Pub. Date: Oct. 25, 2018

(65) Prior Publication Data
US 2020/0181682 A1   Jun. 11, 2020

(30) Foreign Application Priority Data

Apr. 19, 2017 (JP) .................... 2017-082629
Aug. 24, 2017 (JP) .................... 2017-160775
Dec. 29, 2017 (JP) .................... 2017-255105

(51) Int. Cl.
*C12Q 1/686* (2018.01)
*B01L 3/00* (2006.01)
*C12N 15/10* (2006.01)

(52) U.S. Cl.
CPC ............ *C12Q 1/686* (2013.01); *B01L 3/502* (2013.01); *C12N 15/10* (2013.01)

(58) Field of Classification Search
None
See application file for complete search history.

(56) References Cited

U.S. PATENT DOCUMENTS 5,273,907 A    12/1993  Malmquist
5,364,591 A *  11/1994  Green ................ A61B 10/0096
                                                         436/538

(Continued)

FOREIGN PATENT DOCUMENTS

CN    1506452 A    6/2004
CN    2864677 Y    1/2007

(Continued)

*Primary Examiner* — William H. Beisner
(74) *Attorney, Agent, or Firm* — Rabin & Berdo, P.C.

(57) ABSTRACT

A PCR vessel (1) is mainly constituted of a vessel body (11) having a reaction chamber (12) storing and reacting a specimen and a reagent at the time of PCR on a bottom portion (14) thereof, a lid body (6) fittable with the vessel body (11), and a reagent cassette (16) stored in a portion between a lower surface (7) of the lid body (5) and the reaction chamber (12) in the vessel body (11). The reagent cassette (16) has at least one reagent storing portion capable of sealing the reagent with sealing means such as paraffin solid before PCR and melted by heating in PCR. When structuring the PCR vessel in this manner, the sealing means is melted by heating in PCR and the reagent storing portion is opened when storing a specimen necessary for PCR in the vessel body and performing PCR in a state previously storing and sealing the reagent in the reagent storing portion. Then, the specimen and the reagent move to the lower reaction chamber.

18 Claims, 33 Drawing Sheets

(56) References Cited

U.S. PATENT DOCUMENTS

| | | | |
|---|---|---|---|
| 5,556,773 A * | 9/1996 | Yourno | C12Q 1/6848 |
| | | | 435/5 |
| 5,840,878 A * | 11/1998 | Collis | C12Q 1/24 |
| | | | 536/25.4 |
| 5,955,351 A | 9/1999 | Gerdes et al. | |
| 6,153,425 A | 11/2000 | Kozwich et al. | |
| 6,432,694 B1 | 8/2002 | Malmqvist | |
| 6,649,378 B1 | 11/2003 | Kozwich et al. | |
| 9,442,046 B2 * | 9/2016 | Biadillah | A61B 10/007 |
| 2004/0110167 A1 | 6/2004 | Gerdes et al. | |
| 2004/0112969 A1 | 6/2004 | Saga et al. | |
| 2012/0149005 A1 | 6/2012 | Kojima et al. | |
| 2014/0058043 A1 | 2/2014 | Miyamoto et al. | |
| 2016/0209332 A1 | 7/2016 | Miyamoto et al. | |

FOREIGN PATENT DOCUMENTS

| | | | | |
|---|---|---|---|---|
| CN | 101787347 A | * | 7/2010 | B01L 3/50825 |
| CN | 205741038 U | * | 11/2016 | |
| JP | 2001508644 A | | 7/2001 | |
| JP | 2002532059 A | | 10/2002 | |
| JP | 2009106221 A | * | 5/2009 | |
| JP | 2009106221 A | | 5/2009 | |
| JP | 2012118055 A | | 6/2012 | |
| WO | 2012121225 A1 | | 9/2012 | |

\* cited by examiner

FIG. 6
(1)
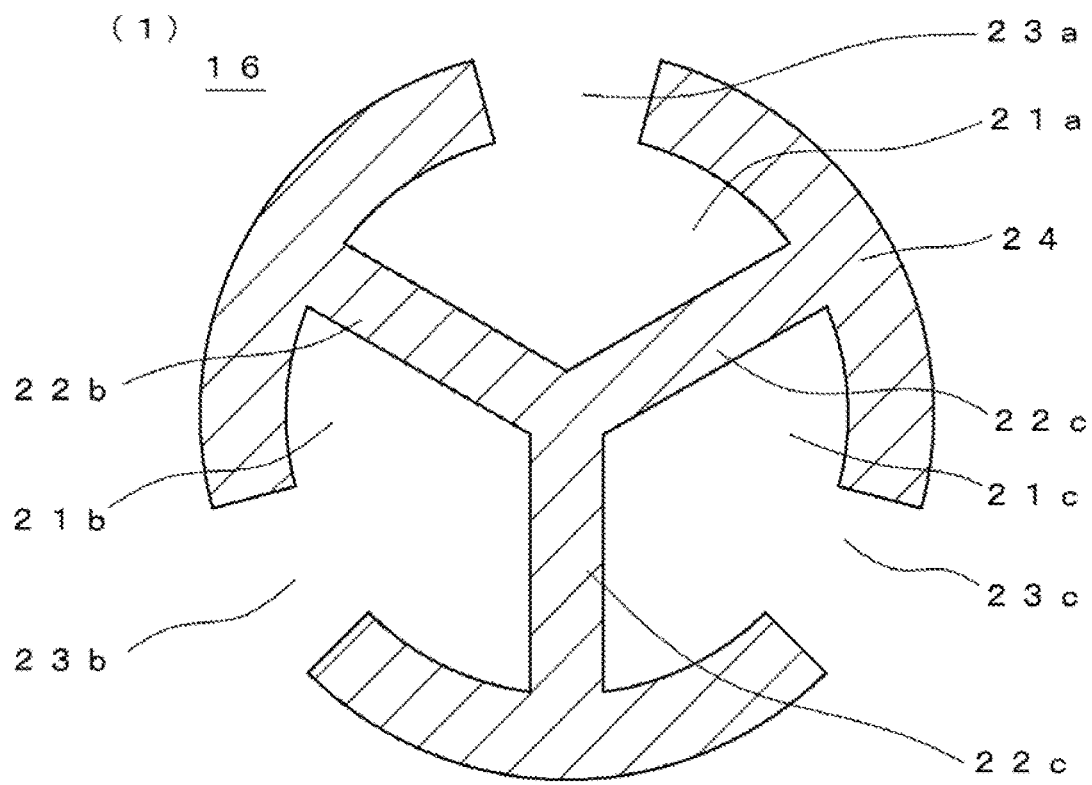
(2)
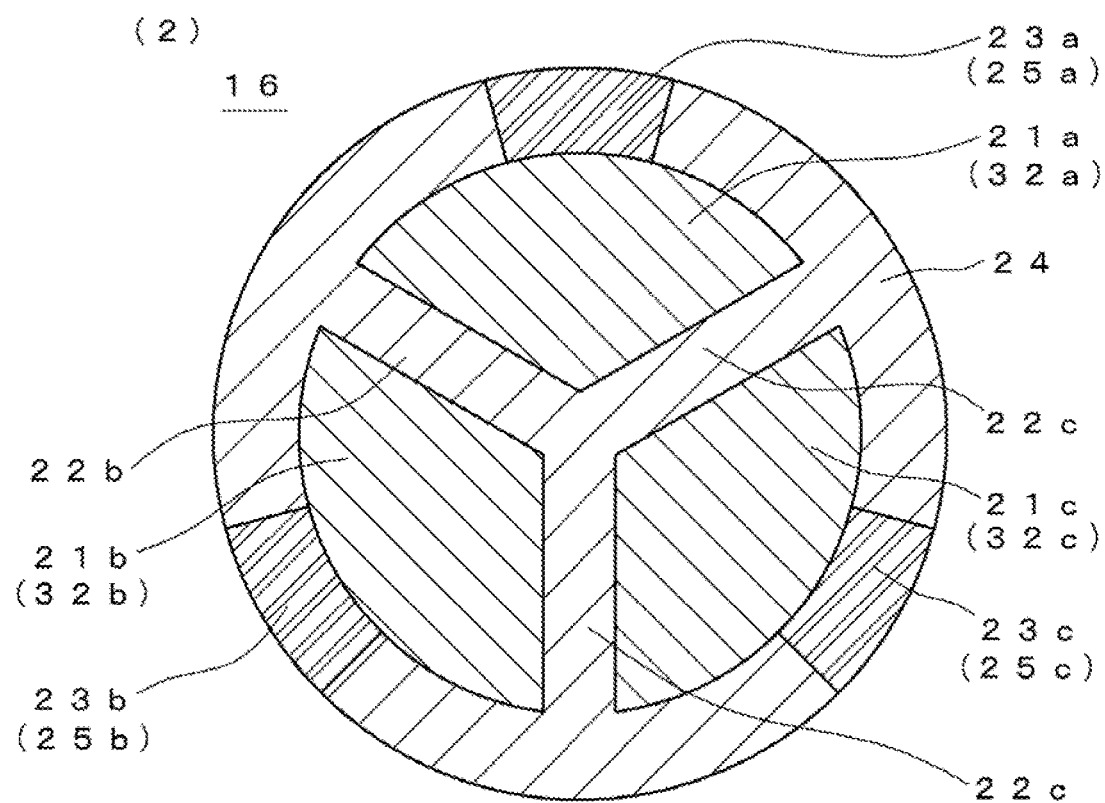

FIG. 15
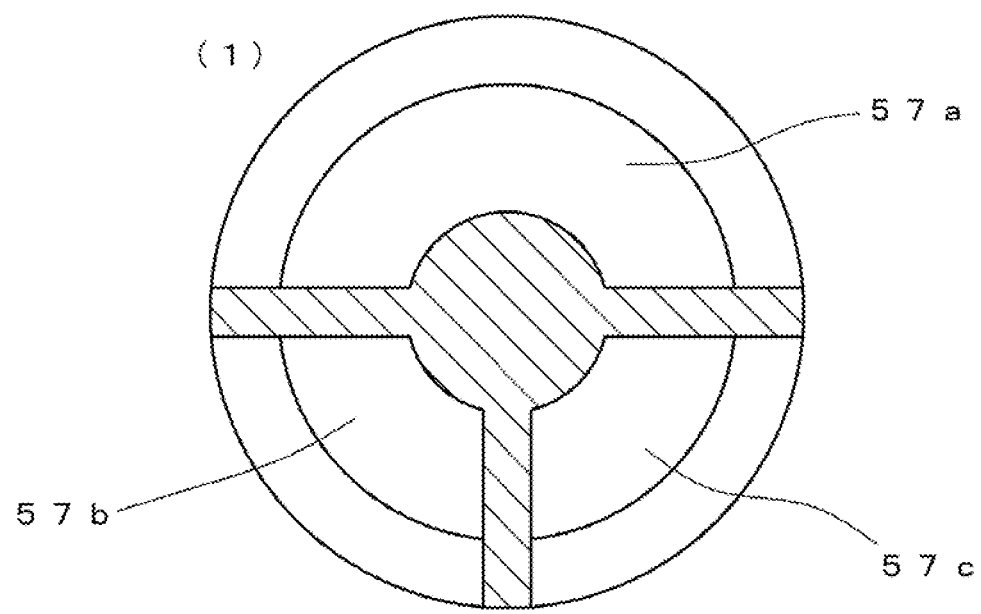
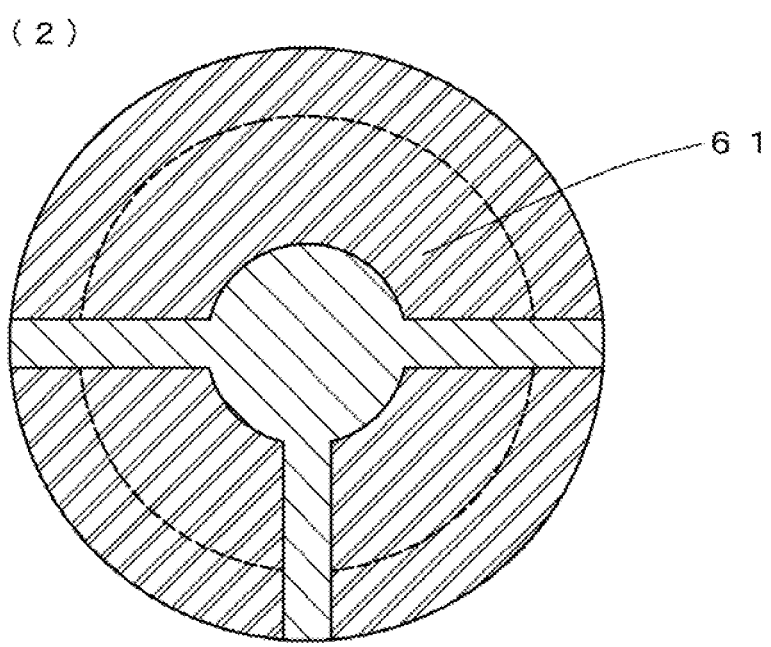

FIG. 17
(1)
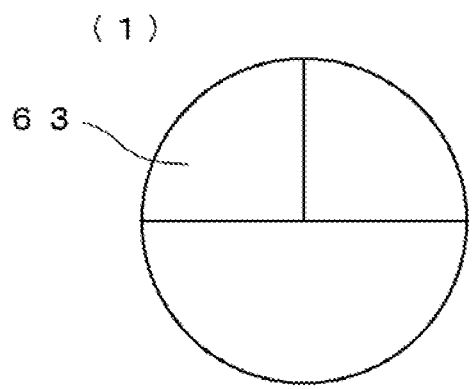
(4)
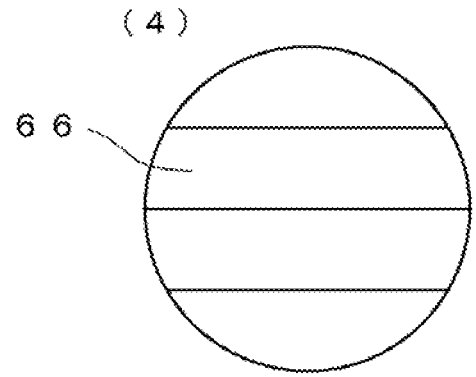
(2)
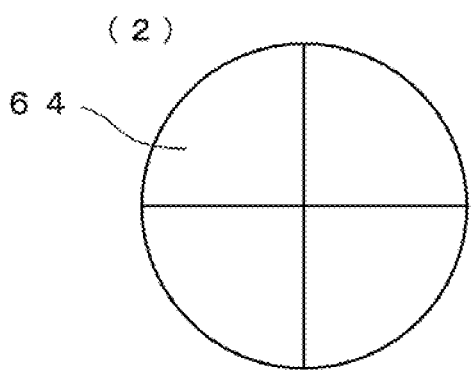
(5)
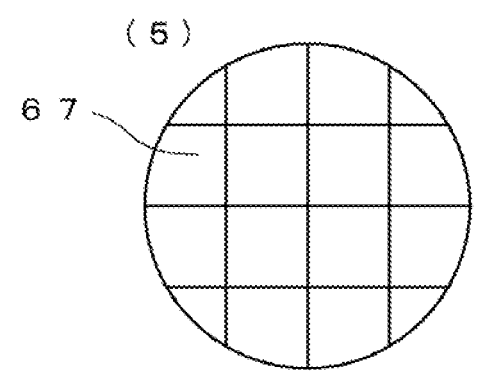
(3)
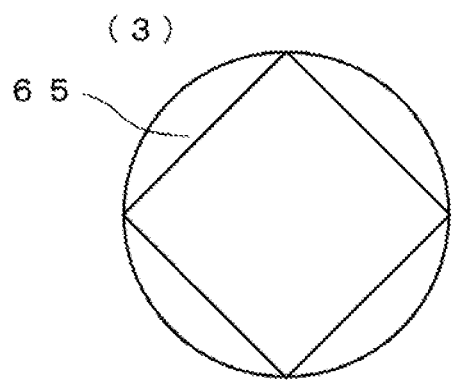
(6)
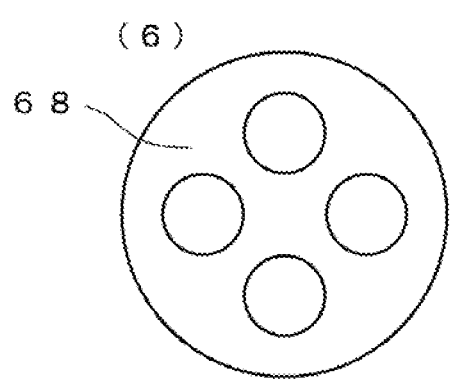

FIG. 19
PRIOR ART
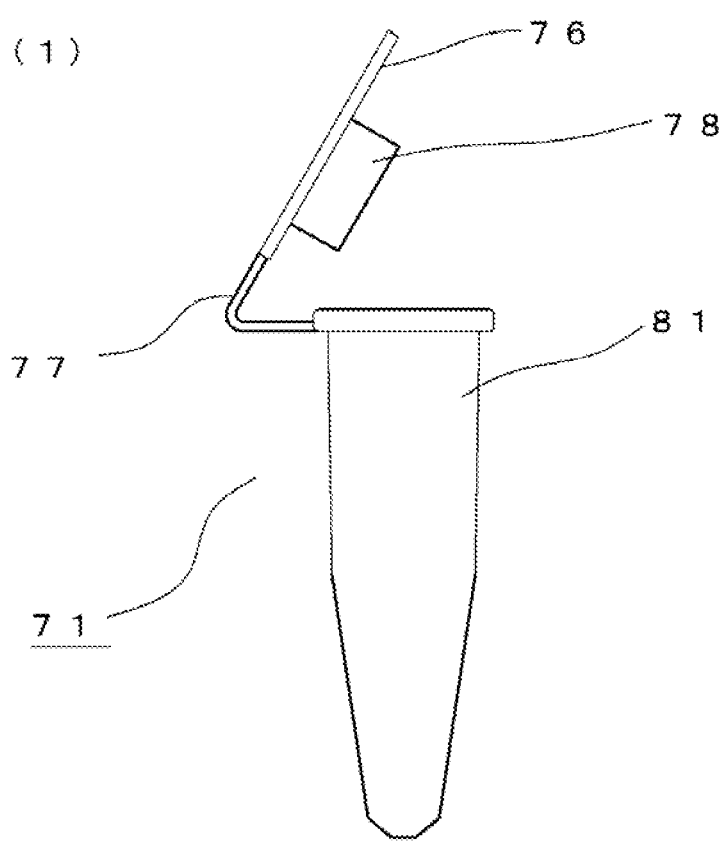
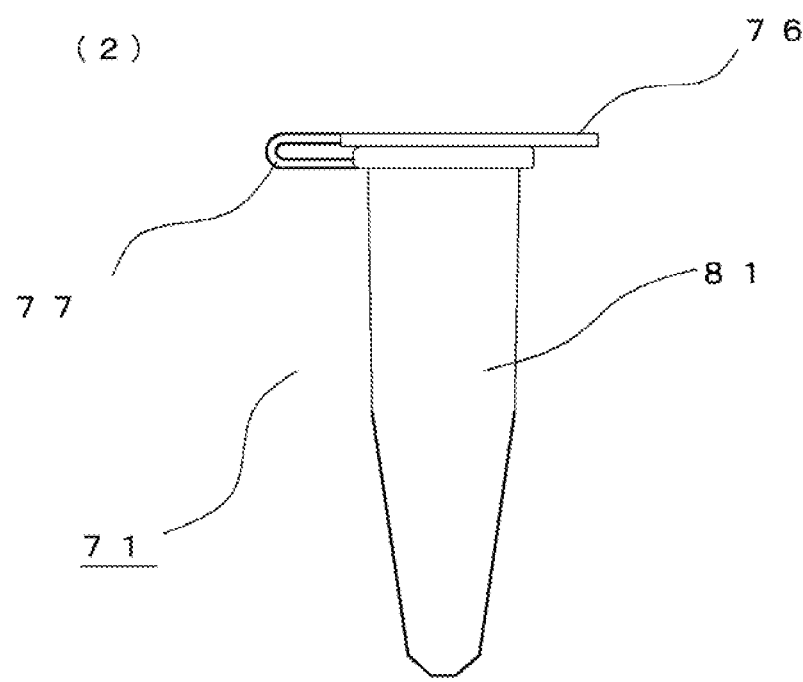

FIG. 23
(1)
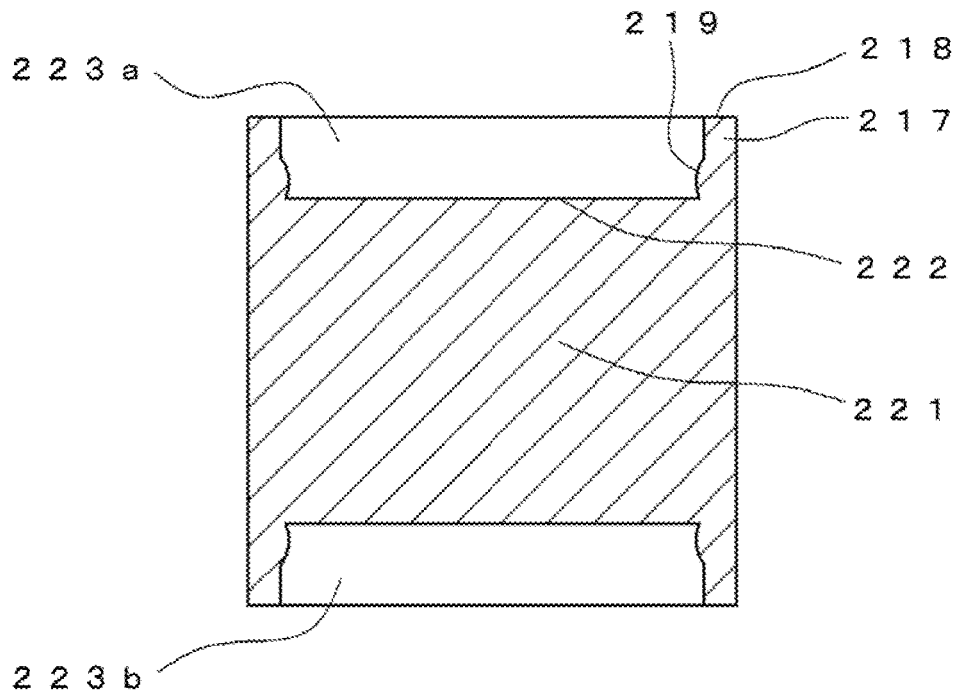
(2)
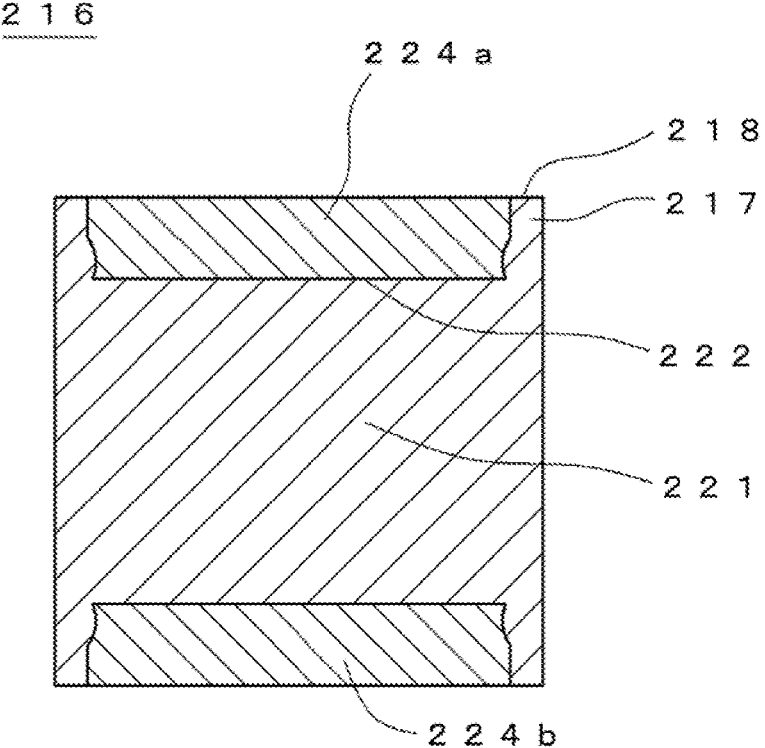

FIG. 31
(1)
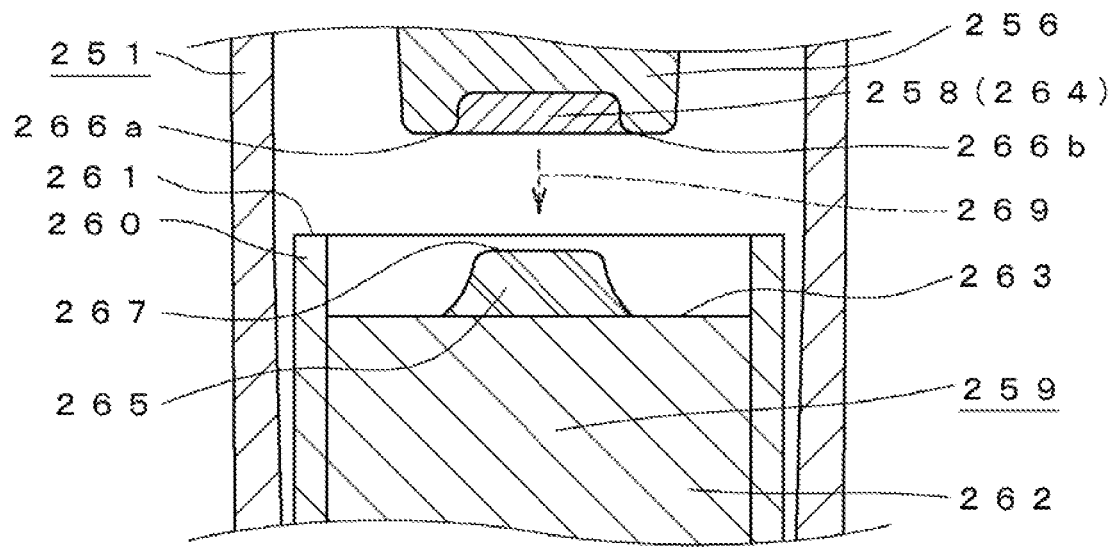
(2)
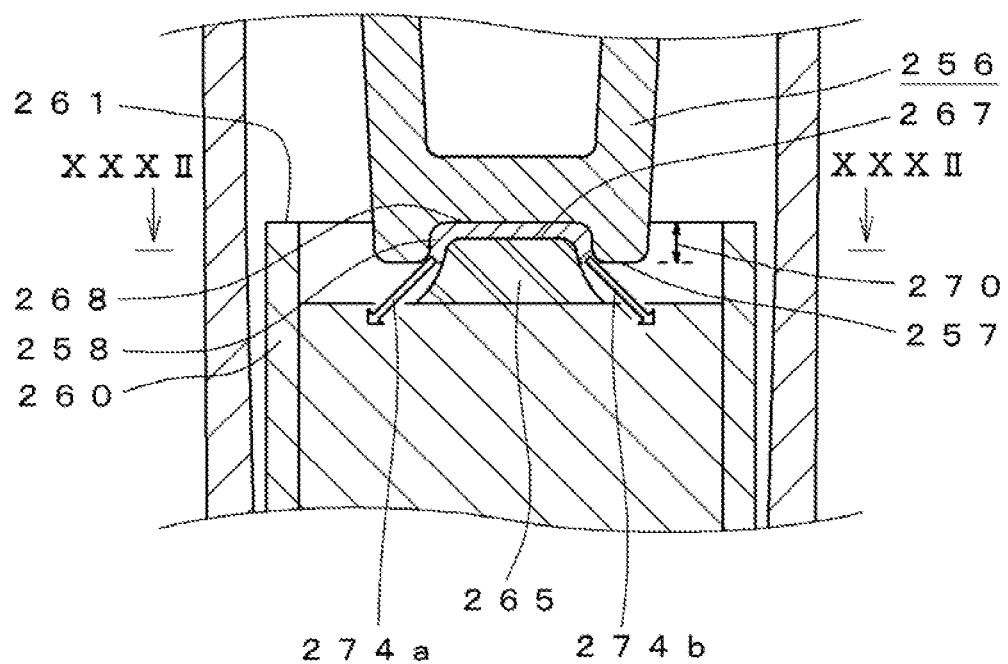

FIG. 33
(1)
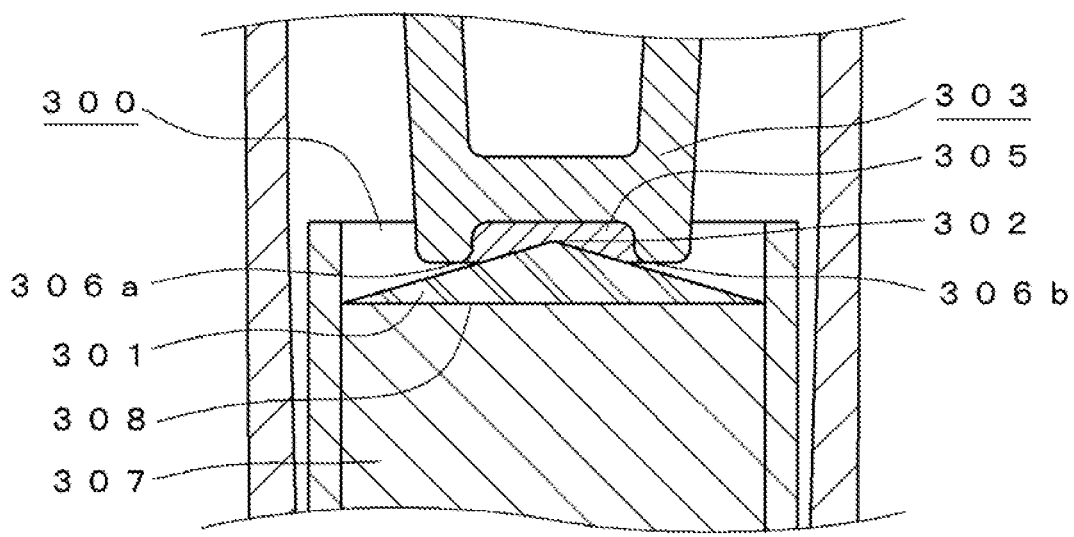
(2)
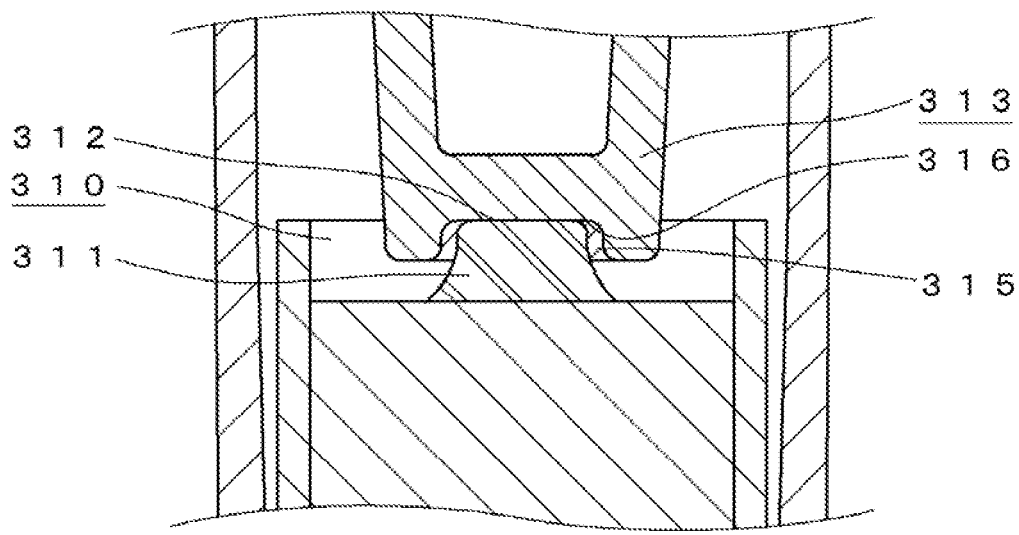

PCR VESSEL, PCR VESSEL CONTAINING REAGENT, AND REAGENT CASSETTE

TECHNICAL FIELD

The present invention relates to a PCR vessel, a PCR vessel containing a reagent, and a reagent cassette, and more particularly, it relates to a PCR vessel employed when performing PCR with a DNA detector, a PCR vessel containing a reagent, and a reagent cassette.

BACKGROUND ART

In general, a PCR vessel shown in FIGS. 19 and 20 is employed when amplifying DNA by polymerase chain reaction (referred to as "PCR" in this specification).

FIG. 19 illustrates schematic front elevational views showing the appearance of a conventional PCR vessel with (1) in a state where a lid body is opened and (2) in a state where the lid body is closed, while FIG. 20 is a sectional view showing a central sectional structure in the state where the lid body of the PCR vessel is closed as shown at (2) in FIG. 19.

Referring to these figures, a PCR vessel 71 is made of polypropylene, for example, and mainly constituted of a vessel body 81, a lid body 76 and a connecting portion 77.

The vessel body 81 has a cylindrical shape opened in an upper portion (a direction where the lid body is present with respect to the vessel body when the PCR vessel is in use), while a bottom portion thereof is closed.

The lid body 76 has a discoidal shape, with a size capable of completely covering the upper opening of the vessel body 81. In the lid body 76, a downwardly projecting circular ring-shaped lock portion 78 is formed on a lower surface thereof. As shown in FIG. 20, the outer surface of a sidewall of the lock portion 78 locks with an inner wall surface of the vessel body 81 in a state where the lid body 76 is closed, so that the lid body 76 is fixed in a state completely covering the upper opening of the lid body 81. Thus, the lid body prevents mixing of foreign matter into the vessel body 81 and evaporation of substances stored in the vessel body 81 during PCR reaching at least 90° C. at the maximum.

The connecting portion 77 is in the shape of a band flexible in the range of prescribed angles, and one end thereof is connected with an end portion of the lid body 76, while the other end is connected with an end portion of the vessel body 81. The connecting portion 77 is so flexed and brought into a closed state that the lid body 76 fits with the vessel body 81.

When using the PCR vessel 71, an unshown specimen (saliva, for example) containing target DNA and unshown respective reagents (water, a buffer solution, a primer, dNTP, DNA polymerase and a fluorescent reagent, for example) necessary for progress of PCR are first introduced into the vessel body 81 in necessary quantities with labware such as a micropipette in a state where the lid body 76 is opened as shown at (1) in FIG. 19. Then, the upper surface of the lid body 76 is pressed from above, whereby the outer surface of the lock portion 78 of the lid body 76 locks with the inner surface of the vessel body 81, and the lid body 76 is fixed in a closed state shown at (2) in FIG. 19. The PCR vessel 71 in this state is set in an unshown DNA amplifier such as a thermal cycler and a cycle of heating and cooling is repeated by a prescribed number of times, whereby PCR progresses to amplify the target DNA. After PCR is completed, it is also possible to recover substances, including the amplified target DNA, stored in the PCR vessel 71 into another vessel and to detect the presence of the target DNA by photodetection, if necessary.

In Japanese Unexamined Patent Publication No. 2009-106221, there is disclosed a reaction vessel containing a reagent employed for reaction in a state isolated from a reaction region by a partition wall, in which the partition wall is set to be temperature-controllable independently of a reaction solution and at least a part of the partition wall is fused by heating so that the reagent is dischargeable into the reaction region. Such a mode is disclosed that the partition wall is made of wax, grease or the like and set horizontally in the reaction vessel.

PRIOR ART

Patent Document

[Patent Document 1] Japanese Unexamined Patent Publication No. 2009-106221

In the aforementioned conventional PCR vessel, there have been such problems that labware such as a micropipette must be employed in order to measure reagents in quantities necessary for progress of PCR, it is complicated, and the yield of PCR is remarkably influenced by the dexterity of the ability of the experimenter. Further, there has also been apprehension of in-situ contamination with reagents and PCR products and contamination on the experimenter. Therefore, a technique with which even an unskilled operator easily and safely obtains stable measurement results of PCR has been awaited.

While one of means for solving the problems has been suggested in Japanese Unexamined Patent Publication No. 2009-106221, it has been practically difficult to stably form the partition wall in the reaction vessel. In other words, it is difficult to form a partition wall in a reaction vessel with wax in a melted state or the like since the shape is easily lost by an impact of dripping the wax in a melted state into the reaction vessel, and it has been difficult to set the partition wall absolutely without leaving a space between the partition wall and the inner surface of the reaction vessel so that reagents do not fall into the reaction region due to inclination or the like at the time of setting, even if a partition wall made of wax in a solid state or the like is previously prepared to be stored in the reaction vessel.

The present invention has been proposed in order to solve the aforementioned problems, and aims at providing a PCR vessel capable of simply and stably improving reliability and rapidity of PCR, a PCR vessel containing a reagent, and a reagent cassette.

DISCLOSURE OF THE INVENTION

In order to attain the aforementioned object, a PCR vessel according to a first aspect of the present invention is a PCR vessel including a vessel body having a reaction chamber storing and reacting a specimen and a reagent at the time of PCR on a bottom portion thereof, a lid body fittable with the vessel body, and a reagent cassette stored in a portion between a lower surface of the lid body and the reaction chamber in the vessel body, while the reagent cassette has at least one reagent storing portion capable of sealing the reagent with sealing means solid before PCR and melted by heating in PCR.

When structuring the PCR vessel in this manner, the sealing means is melted by heating in PCR and the reagent storing portion is opened when storing a specimen necessary for PCR in the vessel body and performing PCR in a state previously storing and sealing the reagent in the reagent storing portion. Then, the specimen and the reagent move to the lower reaction chamber.

The PCR vessel according to a second aspect of the present invention is such that, in the structure of the invention according to the first aspect, an upwardly concave recess portion capable of storing at least a part of the specimen through contact with the specimen is formed on the lower surface of the lid body, and the reagent storing portion has a shape penetrating in the vertical direction.

When structuring the PCR vessel in this manner, the sealing means is melted by heating in PCR and the reagent storing portion penetrates in the vertical direction when storing the specimen by employing the recess portion on the lower surface of the lid body and performing PCR in a state previously storing and sealing the reagent in the reagent storing portion. Then, the specimen moves from the recess portion on the lower surface of the lid body to the reagent storing portion, and the specimen and the reagent move to the lower reaction chamber.

The PCR vessel according to a third aspect of the present invention is such that, in the structure of the invention according to the first aspect or the second aspect, a plurality of reagent storing portions are provided in the reagent cassette, and the plurality of reagent storing portions are separated from each other by a partition wall.

When structuring the PCR vessel in this manner, the plurality of reagent storing portions can be sealed in a state where reagents stored in the respective ones thereof are not mixed with each other.

The PCR vessel according to a fourth aspect of the present invention is such that, in the structure of the invention according to any of the first aspect to the third aspect, the reagent cassette has a tubular shape opened in the vertical direction, and a slit extending in the vertical direction and communicating with the reagent storing portion is formed on a sidewall thereof.

When structuring the PCR vessel in this manner, the surface area of a portion of the reagent cassette from which the reagent flows out increases.

The PCR vessel according to a fifth aspect of the present invention is such that, in the structure of the invention according to any of the first aspect to the fourth aspect, the reaction chamber is in the shape of a truncated quadrangular pyramid, and made of a transparent material.

When structuring the PCR vessel in this manner, opposed surfaces are formed in the reaction chamber.

The PCR vessel according to a sixth aspect of the present invention is such that, in the structure of the invention according to any of the first aspect to the fifth aspect, the vessel body, the lid body and the reagent cassette are set in such a dimensional relation that a clearance is formed between the lower surface of the lid body and the reagent cassette when the lid body fits with the vessel body.

When structuring the PCR vessel in this manner, the clearance can be sealed with the sealing means at the time of use.

The PCR vessel according to a seventh aspect of the present invention is such that, in the structure of the invention according to any of the first aspect to the sixth aspect, at least a part of the inner surface of the vessel body inwardly projects toward the reagent cassette.

When structuring the PCR vessel in this manner, positioning of the reagent cassette in the vessel body is simplified.

The PCR vessel according to an eighth aspect of the present invention is such that, in the structure of the invention according to any of the first aspect to the seventh aspect, the thickness of the vessel body is at least 0.05 mm and not more than 0.5 mm.

When structuring the PCR vessel in this manner, the thicknesses of the portion of the vessel body in which the reagent cassette is stored and the reaction chamber are at least 0.05 mm and not more than 0.5 mm.

The PCR vessel according to a ninth aspect of the present invention is such that, in the structure of the invention according to any of the first aspect to the eighth aspect, the sealing means is wax, grease, paraffin or wax.

When structuring the PCR vessel in this manner, the sealing means is solid at ordinary temperature and entering a liquid state at the time of first heating in PCR.

The PCR vessel according to a tenth aspect of the present invention is such that, in the structure of the invention according to any of the first aspect to the ninth aspect, an inwardly concave recess-like portion is formed on at least one of an upper surface and a lower surface of the reagent cassette.

When structuring the PCR vessel in this manner, an inwardly concave portion is formed on the upper surface or the lower surface of the reagent cassette.

The PCR vessel according to an eleventh aspect of the present invention is such that, in the structure of the invention according to any of the first aspect to the tenth aspect, an upwardly concave recess portion capable of storing at least a part of the specimen through contact with the specimen is formed on the lower surface of the lid body, the reagent storing portion has a shape penetrating in the vertical direction, an upwardly convex projecting portion is formed on an upper surface of the reagent cassette, and the projecting portion enters at least a part of the recess portion when the lid body fits with the vessel body.

When structuring the PCR vessel in this manner, the specimen stored in the recess portion on the lower surface of the lid body can be easily scraped out at the time of use.

The PCR vessel according to a twelfth aspect of the present invention is such that, in the structure of the invention according to any of the first aspect to the eleventh aspect, a downwardly convex portion is formed on the lower surface of the reagent cassette.

When structuring the PCR vessel in this manner, the lower surface of the reagent cassette is not horizontal but convex toward the reaction chamber.

A PCR vessel containing a reagent according to a thirteenth aspect of the present invention is a PCR vessel containing a reagent employing the PCR vessel according to any of the first aspect to the twelfth aspect, in which the reagent is stored in the reagent storing portion and sealed by the sealing means in the reagent cassette.

When structuring the PCR vessel containing a reagent in this manner, the reagent is previously stored and sealed in the reagent cassette.

The PCR vessel containing a reagent according to a fourteenth aspect of the present invention is such that, in the structure of the invention according to the thirteenth aspect, the reaction chamber is filled with the sealing means.

When structuring the PCR vessel containing a reagent in this manner, the reaction chamber enters a state from which air is discharged before PCR, while the sealing means is melted so that the specimen and the reagent are stored through the reagent cassette at the time of PCR.

A reagent cassette according to a fifteenth aspect of the present invention is a reagent cassette stored in a PCR vessel, and includes a reagent storing portion, while a reagent necessary for PCR is stored in the reagent storing portion, and sealed with sealing means solid before PCR and melted by heating in PCR.

When structuring the reagent cassette in this manner, the reagent is previously stored and sealed in the reagent cassette.

A PCR vessel according to a sixteenth aspect of the present invention is a PCR vessel including a vessel body having a reaction chamber storing and reacting a specimen and a reagent at the time of PCR on a bottom portion thereof and a lid body fittable with the vessel body, while the lid body has at least one reagent storing portion formed on a forward end portion thereof through an exposed portion constituting a part of a lower surface of the forward end portion, an upwardly concave recess portion capable of storing at least a part of the specimen through contact with the specimen is formed on another part of the lower surface of the forward end portion, and the exposed portion of the reagent storing portion is sealable with sealing means solid before PCR and melted by heating in PCR.

When structuring the PCR vessel in this manner, the sealing means is melted by heating in PCR so that the reagent storing portion and the recess portion are opened when storing the specimen by employing the recess portion on the lower surface of the lid body and performing PCR in a state previously storing and sealing the reagent in the reagent storing portion. Then, the specimen and the reagent move to the lower reaction chamber.

The PCR vessel according to a seventeenth aspect of the present invention is such that, in the structure of the invention according to the sixteenth aspect, an opening penetrating the reagent storing portion is formed on a sidewall of the forward end portion.

When structuring the PCR vessel in this manner, the reagent can be injected from the opening formed on the sidewall of the forward end portion into the reagent storing portion.

A reagent cassette according to an eighteenth aspect of the present invention is a reagent cassette stored in a PCR vessel, and includes a basic framework and at least one reagent storing portion formed by the basic framework, at least partially externally exposed, and capable of storing a reagent necessary for PCR.

When structuring the reagent cassette in this manner, a sealing means is melted by heating in PCR so that the reagent storing portion is opened when storing a specimen necessary for PCR in the vessel and performing PCR in a state storing the reagent in the reagent storing portion and sealing the same with the sealing means solid before PCR and melted by heating in PCR. Then, the specimen and the reagent move to a reaction chamber on a lower portion of the vessel.

The reagent cassette according to a nineteenth aspect of the present invention is such that, in the structure of the invention according to the eighteenth aspect, the reagent storing portion has a shape exposed on opposed surfaces.

When structuring the reagent cassette in this manner, a sealing means is melted by heating in PCR and a specimen is mixed with the reagent in the process of moving from the opened reagent storing portion to another side of the exposed portion when storing the specimen on one side of the exposed portion of the reagent cassette.

The reagent cassette according to a twentieth aspect of the present invention is such that, in the structure of the invention according to the eighteenth aspect or the nineteenth aspect, a plurality of reagent storing portions are provided, and the plurality of reagent storing portions are formed by basic frameworks separated from each other by a partition wall.

When structuring the reagent cassette in this manner, the plurality of reagent storing portions can be sealed in a state where reagents stored in the respective ones thereof are not mixed with each other.

The reagent cassette according to a twenty-first aspect of the present invention is such that, in the structure of the invention according to the twentieth aspect, the reagent storing portions are provided in three, the partition walls are three platelike bodies extending in the same direction, the respective ones of the adjacent platelike bodies intersect with each other to mutually form an angle of 120°, and the reagent storing portions have shapes exposed on both ends in the same direction.

When structuring the reagent cassette in this manner, three reagent storing portions having identical volumes are formed.

The reagent cassette according to a twenty-second aspect of the present invention is such that, in the structure of the invention according to any of the eighteenth aspect to the twenty-first aspect, the basic framework has a tubular shape whose both ends in the axial direction are opened, and a slit extending in the axial direction and communicating with the reagent storing portion is formed on a sidewall thereof.

When structuring the reagent cassette in this manner, the surface area of a portion of the reagent cassette from which the reagent flows out increases.

The reagent cassette according to a twenty-third aspect of the present invention is such that, in the structure of the invention according to any of the eighteenth aspect to the twenty-second aspect, the basic framework is set in such a dimensional relation that at least a part of a lower surface thereof is in contact with the inner surface of the PCR vessel and at least a part of an upper surface thereof is in contact with the lower surface of the lid body of the PCR vessel in a state stored in the PCR vessel.

When structuring the reagent cassette in this manner, the reagent cassette is prevented from unpreparedly moving in the vertical direction in the PCR vessel.

The reagent cassette according to a twenty-fourth aspect of the present invention is such that, in the structure of the invention according to any of the eighteenth aspect to the twenty-third aspect, an inwardly concave recess-like portion is formed on at least a part of at least one of opposed surfaces of the basic framework.

When structuring the reagent cassette in this manner, the sealing means easily remains in the recess-like portion at the time of sealing.

The reagent cassette according to a twenty-fifth aspect of the present invention is such that, in the structure of the invention according to any of the eighteenth aspect to the twenty-fourth aspect, the reagent storing portion has a shape exposed in the vertical direction in a state stored in the PCR vessel, an upwardly convex projecting portion is formed on at least a part of an upper surface of the basic framework, and the projecting portion enters at least a part of a recess portion formed on a lower surface of a lid body of the PCR vessel in a state stored in the PCR vessel.

When structuring the reagent cassette in this manner, a substance stored in the recess portion of the lid body of the PCR vessel can be easily scraped out by the reagent cassette.

The reagent cassette according to a twenty-sixth aspect of the present invention is such that, in the structure of the invention according to any of the eighteenth aspect to the twenty-fifth aspect, an externally convex portion is formed on at least a part of one surface of the basic framework.

When structuring the reagent cassette in this manner, the lower surface of the reagent cassette can be rendered not horizontal but convex toward the reaction chamber.

A reagent cassette according to a twenty-seventh aspect of the present invention is a reagent cassette stored in a PCR vessel, and includes a basic framework, a reagent storing portion formed by the basic framework, externally exposed through an exposed portion, and storing a reagent necessary for PCR, and sealing means sealing the exposed portion by being solid before PCR and melted by heating in PCR.

When structuring the reagent cassette in this manner, the reagent is previously stored and sealed in the reagent cassette, and the sealing means is melted by heating in PCR so that the reagent storing portion is opened when storing a specimen necessary for PCR in the vessel and performing PCR. Then, the specimen and the reagent move to the reaction chamber on the lower portion of the vessel.

The reagent cassette according to a twenty-eighth aspect of the present invention is such that, in the structure of the invention according to the twenty-seventh aspect, the sealing means is wax, grease, paraffin or wax.

When structuring the reagent cassette in this manner, the sealing means is solid at ordinary temperature, and enters a liquid state at the time of first heating in PCR.

The reagent cassette according to a twenty-ninth aspect of the present invention is such that, in the structure of the invention according to the twenty-seventh aspect or the twenty-eighth aspect, the basic framework is not melted by heating in PCR.

When structuring the reagent cassette in this manner, only the sealing means is melted by heating in PCR so that the reagent storing portion is opened.

The reagent cassette according to a thirtieth aspect of the present invention is such that, in the structure of the invention according to any of the eighteenth aspect to the twenty-sixth aspect, the basic framework has a tubular shape opened on both ends in the axial direction while the inner portion thereof is divided by a partition wall extending in the axial direction, and at least one of both edges of the partition wall in the axial direction is positioned inward beyond at least one of corresponding both opposed open end surfaces of the basic framework.

When structuring the reagent cassette in this manner, the sealing means easily remains in a portion from an edge of the partition wall in the axial direction to an open end surface of the basic framework at the time of sealing.

A PCR vessel according to a thirty-first aspect of the present invention is a PCR vessel, and includes a vessel body having a reaction chamber storing and reacting a specimen and a reagent at the time of PCR on a bottom portion thereof, a lid body fittable with the vessel body and provided with an upwardly concave recess portion capable of storing at least a part of the specimen through contact with the specimen on a lower surface thereof and a reagent cassette stored in a portion between the lid body and the reaction chamber in the vessel body, while the reagent cassette includes a basic framework having a tubular shape opened in the vertical direction, a reagent storing portion capable of storing the reagent is formed in the basic framework, the reagent storing portion can seal the reagent with sealing means solid before PCR and melted by heating in PCR, and at least one of the vessel body, the lid body and the reagent cassette includes regulation means regulating the specimen or the reagent not to leak out of the reaction chamber at the time of PCR.

When structuring the PCR vessel in this manner, the specimen or the reagent stably flows into the reaction chamber at the time of PCR due to the regulation means.

A PCR vessel according to a thirty-second aspect of the present invention is a PCR vessel, and includes a vessel body having a reaction chamber storing and reacting a specimen and a reagent at the time of PCR on a bottom portion thereof, a lid body fittable with the vessel body and provided with an upwardly concave recess portion capable of storing at least a part of the specimen through contact with the specimen on a lower surface thereof and a reagent cassette stored in a portion between the lid body and the reaction chamber in the vessel body, while the reagent cassette includes a basic framework having a tubular shape opened in the vertical direction, and a reagent storing portion capable of storing the reagent is formed in the basic framework, the reagent storing portion can seal the reagent with sealing means solid before PCR and melted by heating in PCR, and an upper edge of the reaction chamber has a circular shape in plan view.

When structuring the PCR vessel in this manner, the specimen or the reagent stably flows into the reaction chamber at the time of PCR, also in a case where the reagent cassette is stored in the vessel body in a state rotating in the peripheral direction.

The PCR vessel according to a thirty-third aspect of the present invention is such that, in the structure of the invention according to the thirty-second aspect, the reaction chamber has a downwardly tapered conical shape.

When structuring the PCR vessel in this manner, the forward end of the reaction chamber is sharpened as compared with a semispherical one or a cylindrical one. Further, the thickness of the reaction chamber portion can be easily reduced in production.

A PCR vessel according to a thirty-fourth aspect of the present invention is a PCR vessel, and includes a vessel body having a reaction chamber storing and reacting a specimen and a reagent at the time of PCR on a bottom portion thereof, a lid body fittable with the vessel body and provided with an upwardly concave recess portion capable of storing at least a part of the specimen through contact with the specimen on a lower surface thereof and a reagent cassette stored in a portion between the lid body and the reaction chamber in the vessel body, while the reagent cassette includes a basic framework having a tubular shape opened in the vertical direction, and a reagent storing portion capable of storing the reagent is formed in the basic framework, the reagent storing portion can seal the reagent with sealing means solid before PCR and melted by heating in PCR, and an upper edge of the reaction chamber is set to be positioned outward beyond the maximum movable region of an outer edge of a lower end of the reagent storing portion at the time of storage.

When structuring the PCR vessel in this manner, the specimen or the reagent stably flows into the reaction chamber also in a state where the reagent cassette is stored while deviating in the lateral direction.

A PCR vessel according to a thirty-fifth aspect of the present invention is a PCR vessel, and includes a vessel body having a reaction chamber storing and reacting a specimen and a reagent at the time of PCR on a bottom portion thereof, a lid body fittable with the vessel body and provided with an upwardly concave recess portion capable of storing at least a part of the specimen through contact with the specimen on a lower surface thereof, and a reagent cassette stored in a portion between the lid body and the reaction chamber in the vessel body, while the reagent cassette includes a basic framework having a tubular shape opened in the vertical direction, and a plurality of reagent storing portions separated from each other by a partition wall extending in the vertical direction and capable of storing the reagent in the respective ones thereof are formed in the basic framework, the reagent storing portions can seal the reagent with sealing means solid before PCR and melted by heating in PCR, and an upper edge of the partition wall is positioned downward beyond an upper edge of the basic framework, and the lower surface of the lid body is arranged between the upper edge of the partition wall and the upper edge of the basic framework in a state where the lid body and the reagent cassette are mounted on the vessel body.

When structuring the PCR vessel in this manner, the lower surface of the lid body easily enters the sealing means of the reagent cassette in a state mounted on the vessel body.

The PCR vessel according to a thirty-sixth aspect of the present invention is such that, in the structure of the invention according to the thirty-fifth aspect, the upper edge of the partition wall further includes an upwardly convex projecting portion in a portion inward beyond a lower edge of the recess portion of the lid body in plan view projection, and an upper edge of the projecting portion is arranged on a vertical height position between the lower surface of the lid body and the upper edge of the basic framework and downward beyond an upper edge of the recess portion.

When structuring the PCR vessel in this manner, the projecting portion of the reagent cassette easily enters the recess portion of the lid body in a state mounted on the vessel body.

The PCR vessel according to a thirty-seventh aspect of the present invention is such that, in the structure of the invention according to any of the thirty-second aspect, the thirty-third aspect, the thirty-fifth aspect and the thirty-sixth aspect, an upper edge of the reaction chamber is set to be positioned outward beyond the maximum movable region of an outer edge of a lower end of the reagent storing portion at the time of storage.

When structuring the PCR vessel in this manner, the specimen or the reagent stably flows into the reaction chamber also in a state where the reagent cassette is stored while deviating in the lateral direction.

The PCR vessel according to a thirty-eighth aspect of the present invention is such that, in the structure of the invention according to any of the thirty-second aspect, the thirty-third aspect and the thirty-seventh aspect, a plurality of reagent storing portions separated from each other by a partition wall extending in the vertical direction and capable of storing the reagent in the respective ones thereof are formed in the basic framework, and an upper edge of the partition wall is positioned downward beyond an upper edge of the basic framework, and the lower surface of the lid body is arranged between the upper edge of the partition wall and the upper edge of the basic framework in a state where the lid body and the reagent cassette are mounted on the vessel body.

When structuring the PCR vessel in this manner, the lower surface of the lid body easily enters the sealing means of the reagent cassette in a state mounted on the vessel body.

The PCR vessel according to a thirty-ninth aspect of the present invention is such that, in the structure according to any of the thirty-first aspect to the thirty-eighth aspect, the reaction chamber is made of a transparent material.

When structuring the PCR vessel in this manner, optical transmission of the reaction chamber increases.

The PCR vessel according to a fortieth aspect of the present invention is such that, in the structure of the invention according to any of the thirty-first aspect to the thirty-ninth aspect, the thickness of the reaction chamber of the vessel body is at least 0.05 mm and not more than 0.5 mm.

When structuring the PCR vessel in this manner, heat transmission efficiency from outside the vessel with respect to the reaction chamber is improved.

The PCR vessel according to a forty-first aspect of the present invention is such that, in the structure of the invention according to any of the thirty-first aspect to the fortieth aspect, the sealing means is wax, grease, paraffin or wax.

When structuring the PCR vessel in this manner, the sealing means is solid at ordinary temperature and enters a liquid state at the time of first heating in PCR.

A PCR vessel containing a reagent according to a forty-second aspect of the present invention is a PCR vessel containing a reagent employing the PCR vessel according to any of the thirty-first aspect to the forty-first aspect of the present invention, in which the reagent is stored in the reagent storing portion of the reagent cassette and sealed with the sealing means.

When structuring the PCR vessel containing a reagent in this manner, the reagent is previously stored and sealed in the reagent cassette.

As described above, the PCR vessel according to the first aspect of the present invention is such that the sealing means is melted by heating in PCR and the reagent storing portion is opened when storing a specimen necessary for PCR in the vessel body and performing PCR in a state previously storing and sealing the reagent in the reagent storing portion. Then, the specimen and the reagent move to the lower reaction chamber, whereby the PCR vessel can simply and stably improve reliability and rapidity of PCR.

The PCR vessel according to the second aspect of the present invention is such that, in addition to the effect of the invention according to the first aspect, the sealing means is melted by heating in PCR and the reagent storing portion penetrates in the vertical direction when storing the specimen by employing the recess portion on the lower surface of the lid body and performing PCR in a state previously storing and sealing the reagent in the reagent storing portion. Then, the specimen moves from the recess portion on the lower surface of the lid body to the reagent storing portion and the specimen and the reagent move to the lower reaction chamber, whereby the PCR vessel can further improve simplicity, reliability and rapidity of PCR.

The PCR vessel according to the third aspect of the present invention is such that, in addition to the effect of the invention according to the first aspect or the second aspect, the plurality of reagent storing portions can be sealed in a state where reagents stored in the respective ones thereof are not mixed with each other, whereby reagents not suitable to be previously mixed with each other can be easily employed.

The PCR vessel according to the fourth aspect of the present invention is such that, in addition to the effect of the invention according to any of the first aspect to the third aspect, the surface area of a portion of the reagent cassette from which the reagent flows out increases, whereby the reagent can easily fall from the reagent cassette toward the reaction chamber.

The PCR vessel according to the fifth aspect of the present invention is such that, in addition to the effect of the invention according to any of the first aspect to the fourth aspect, opposed surfaces are formed in the reaction chamber, whereby reliability of photodetection in a case of performing photodetection in the horizontal direction with respect to the reaction chamber after PCR is improved.

The PCR vessel according to the sixth aspect of the present invention is such that, in addition to the effect of the invention according to any of the first aspect to the fifth aspect, the clearance can be sealed with the sealing means at the time of use, whereby such apprehension that the stored reagent leaks out decreases as compared with a case of setting the PCR vessel to such a dimensional relation that no clearance is formed between the lower surface of the lid body and the reagent cassette when the lid body is fitted and the reagent cassette is pressed.

The PCR vessel according to the seventh aspect of the present invention is such that, in addition to the effect of the invention according to any of the first aspect to the sixth aspect, positioning of the reagent cassette in the vessel body is simplified, whereby the reagent can be induced to a position capable of easily falling from the reagent cassette to the reaction chamber, and reliability of PCR is improved.

The PCR vessel according to the eighth aspect of the present invention is such that, in addition to the effect of the invention according to any of the first aspect to the seventh aspect, the thicknesses of the portion of the vessel body in which the reagent cassette is stored and the reaction chamber are at least 0.05 mm and not more than 0.5 mm, whereby the sealing means is properly melted by heating in PCR, and PCR is properly performed.

The PCR vessel according to the ninth aspect of the present invention is such that, in addition to the effect of the invention according to any of the first aspect to the eighth aspect, the sealing means is solid at ordinary temperature and enters a liquid state at the time of first heating in PCR, whereby reliability of PCR is improved.

The PCR vessel according to the tenth aspect of the present invention is such that, in addition to the effect of the invention according to any of the first aspect to the ninth aspect, an inwardly concave portion is formed on the upper surface or the lower surface of the reagent cassette, whereby reliability of sealing with the sealing means is improved.

The PCR vessel according to the eleventh aspect of the present invention is such that, in addition to the effect of the invention according to any of the first aspect to the tenth aspect, the specimen stored in the recess portion on the lower surface of the lid body can be easily scraped out at the time of use, whereby the specimen easily reaches the reaction chamber, and reliability of PCR is improved.

The PCR vessel according to the twelfth aspect of the present invention is such that, in addition to the effect of the invention according to any of the first aspect to the eleventh aspect, the lower surface of the reagent cassette is not horizontal but convex toward the reaction chamber, whereby the reagent can easily fall into the reaction chamber, and reliability of PCR is improved.

The PCR vessel containing a reagent according to the thirteenth aspect of the present invention is such that, in addition to the effect of the invention according to any of the first aspect to the twelfth aspect, the reagent is previously stored and sealed in the reagent cassette, whereby a desired quantity and type of reagent can be previously stored, and reliability and rapidity of PCR can be simply and stably improved.

The PCR vessel containing a reagent according to the fourteenth aspect of the present invention is such that, in addition to the effect of the invention according to the thirteenth aspect, the reaction chamber enters a state where air is discharged before PCR while the sealing means is melted and the specimen and the reagent are stored through the reagent cassette at the time of PCR, whereby the specimen and the reagent can be easily guided to the reaction chamber, and reliability of PCR is improved.

The reagent cassette according to the fifteenth aspect of the present invention is such that the reagent is previously stored and sealed in the reagent cassette, whereby a desired quantity and type of reagent can be previously stored, and reliability and rapidity of PCR can be simply and stably improved by employing the same for a PCR vessel.

The PCR vessel according to the sixteenth aspect of the present invention is such that the sealing means is melted by heating in PCR and the reagent storing portion and the recess portion are opened when storing the specimen by employing the recess portion on the lower surface of the lid body and performing PCR in a state previously storing and sealing the reagent in the reagent storing portion. Then, the specimen and the reagent move to the lower reaction chamber, whereby the PCR vessel can simply and stably improve reliability and rapidity of PCR.

The PCR vessel according to the seventeenth aspect of the present invention is such that, in addition to the effect of the invention according to the sixteenth aspect, the reagent can be injected from the opening formed on the sidewall of the forward end portion into the reagent storing portion, whereby availability is improved.

The reagent cassette according to the eighteenth aspect of the present invention is such that the sealing means is melted by heating in PCR and the reagent storing portion is opened when storing a specimen necessary for PCR in the vessel and performing PCR in a state storing the reagent in the reagent storing portion and sealing the same with the sealing means solid before PCR and melted by heating in PCR. Then, the specimen and the reagent move to a reaction chamber on a lower portion of the vessel, whereby reliability and rapidity of PCR can be simply and stably improved.

The reagent cassette according to the nineteenth aspect of the present invention is such that the sealing means is melted by heating in PCR and the specimen is mixed with the reagent in the process of moving from the opened reagent storing portion to another side of the exposed portion when storing the specimen on one side of the exposed portion of the reagent cassette, whereby reliability and rapidity of PCR can be simply and stably improved.

The reagent cassette according to the twentieth aspect of the present invention is such that, in addition to the effect of the invention according to the eighteenth aspect or the nineteenth aspect, the plurality of reagent storing portions can be sealed in a state where reagents stored in the respective ones thereof are not mixed with each other, whereby reagents not suitable to be previously mixed with each other can be easily employed.

The reagent cassette according to the twenty-first aspect of the present invention is such that, in addition to the effect of the invention according to the twentieth aspect, three reagent storing portions having identical volumes are formed, whereby reagents can easily fall.

The reagent cassette according to the twenty-second aspect of the present is such that, in addition to the effect of the invention according to any of the eighteenth aspect to the twenty-first aspect, the surface area of a portion of the reagent cassette from which the reagent flows out increases, whereby the reagent can easily fall.

The reagent cassette according to the twenty-third aspect of the present invention is such that, in addition to the effect of the invention according to any of the eighteenth aspect to the twenty-second aspect, the reagent cassette is prevented from unpreparedly moving in the vertical direction in the PCR vessel, whereby stability of reaction is improved.

The reagent cassette according to the twenty-fourth aspect of the present invention is such that, in addition to the effect of the invention according to any of the eighteenth aspect to the twenty-third aspect, the sealing means easily remains in the recess-like portion at the time of sealing, whereby reliability of reaction is improved.

The reagent cassette according to the twenty-fifth aspect of the present invention is such that, in addition to the effect according to any of the eighteenth aspect to the twenty-fourth aspect, a substance stored in the recess portion of the lid body of the PCR vessel can be easily scraped out by the reagent cassette, whereby reliability of PCR is improved.

The reagent cassette according to the twenty-sixth aspect of the present invention is such that, in addition to the effect of the invention according to any of the eighteenth aspect to the twenty-fifth aspect, the lower surface of the reagent cassette can be rendered not horizontal but convex toward the reaction chamber, whereby the reagent can easily fall into the reaction chamber, and reliability of PCR is improved.

The reagent cassette according to the twenty-seventh aspect of the present invention is such that the reagent is previously stored and sealed in the reagent cassette, and the sealing means is melted by heating in PCR and the reagent storing portion is opened when storing a specimen necessary for PCR in the vessel and performing PCR. Then, the specimen and the reagent move to the reaction chamber on the lower portion of the vessel, whereby a desired quantity and type of reagent can be previously stored, and reliability and rapidity of PCR can be simply and stably improved by employing the same for a PCR vessel.

The reagent cassette according to the twenty-eighth aspect of the present invention is such that, in addition to the effect of the invention according to the twenty-seventh aspect, the sealing means is solid at ordinary temperature and enters a liquid state at the time of first heating in PCR, whereby reliability of PCR is improved.

The reagent cassette according to the twenty-ninth aspect of the present invention is such that, in addition to the effect of the invention according to the twenty-seventh aspect or the twenty-eighth aspect, only the sealing means is melted by heating in PCR and the reagent storing portion is opened, whereby stability of reaction is improved.

The reagent cassette according to the thirtieth aspect of the present invention is such that, in addition to the effect of the invention according to any of the eighteenth aspect to the twenty-sixth aspect, the sealing means easily remains in a portion from an edge of the partition wall in the axial direction to an open end surface of the basic framework at the time of sealing, whereby reliability of sealing is improved.

The PCR vessel according to the thirty-first aspect of the present invention is such that the specimen or the reagent stably flows into the reaction chamber at the time of PCR due to the regulation means, whereby stability of PCR is improved.

The PCR vessel according to the thirty-second aspect of the present invention is such that the specimen or the reagent stably flows into the reaction chamber at the time of PCR also in a case where the reagent cassette is stored in the vessel body in a state rotating in the peripheral direction, whereby stability of PCR is improved.

The PCR vessel according to the thirty-third aspect of the present invention is such that, in addition to the effect of the invention according to the thirty-second aspect, the forward end of the reaction chamber is sharpened as compared with a semispherical one or a cylindrical one, whereby adhesiveness to a heater heating the PCR vessel increases. Further, the thickness of the reaction chamber portion can be easily reduced in production, whereby the heating time can be shortened. Therefore, efficiency of PCR is improved.

The PCR vessel according to the thirty-fourth aspect of the present invention is such that the specimen or the reagent stably flows into the reaction chamber also in a state where the reagent cassette is stored while deviating in the lateral direction, whereby stability of PCR is improved.

The PCR vessel according to the thirty-fifth aspect of the present invention is such that the lower surface of the lid body easily enters the sealing means of the reagent cassette in a state mounted on the vessel body, whereby the specimen stored in the lid body easily flows into the reagent cassette, and stability of PCR is improved.

The PCR vessel according to the thirty-sixth aspect of the present invention is such that, in addition to the effect of the invention according to the thirty-fifth aspect, the projecting portion of the reagent cassette easily enters the recess portion of the lid body in a state mounted on the vessel body, whereby the specimen stored in the recess portion of the lid body can be easily pushed out by the projecting portion of the reagent cassette, for preventing the specimen from remaining in the recess portion.

The PCR vessel according to the thirty-seventh aspect of the present invention is such that, in addition to the effect of the invention according to any of the thirty-second aspect, the thirty-third aspect, the thirty-fifth aspect and the thirty-sixth aspect, the specimen or the reagent stably flows into the reaction chamber also in a state where the reagent cassette is stored while deviating in the lateral direction, whereby stability of PCR is further improved.

The PCR vessel according to the thirty-eighth aspect of the present invention is such that, in addition to the effect of the invention according to any of the thirty-second aspect, the thirty-third aspect and the thirty-seventh aspect, the lower surface of the lid body easily enters the sealing means of the reagent cassette in a state mounted on the vessel body, whereby the specimen stored in the lid body easily flows into the reagent cassette, and stability of PCR is further improved.

The PCR vessel according to the thirty-ninth aspect of the present invention is such that, in addition to the effect of the invention according to any of the thirty-first aspect to the thirty-eighth aspect, optical transmission of the reaction chamber increases, whereby reliability of photodetection in a case of performing photodetection in the horizontal direction with respect to the reaction chamber after PCR is improved.

The PCR vessel according to the fortieth aspect of the present invention is such that, in addition to the effect of the invention according to any of the thirty-first aspect to the thirty-ninth aspect, heat transmission efficiency from outside the vessel with respect to the reaction chamber is excellent, whereby the sealing means is properly melted by heating in PCR, and PCR is properly performed.

The PCR vessel according to the forty-first aspect of the present invention is such that, in addition to the effect of the invention according to any of the thirty-first aspect to the fortieth aspect, the sealing means is solid at ordinary temperature and enters a liquid state at the time of first heating in PCR, whereby reliability of PCR is improved.

The PCR vessel containing a reagent according to the forty-second aspect of the present invention is such that the reagent is previously stored and sealed in the reagent cassette, whereby a desired quantity and type of reagent can be previously stored, and reliability and rapidity of PCR can be simply and stably improved by employing the same for a PCR vessel.

BRIEF DESCRIPTION OF THE DRAWINGS

FIG. 6 End views along a line VI-VI shown in FIG. 5, with (1) in a state before storing reagents, and (2) in a state after storing and sealing the reagents.

FIG. 15 Sectional views along a line XV-XV shown in FIG. 14, with (1) in a state before storing reagents, and (2) in a state after storing and sealing the reagents.

FIG. 17 Schematic plan views of reagent cassettes of PCR vessels according to other embodiments of the present invention.

FIG. 19 Schematic front elevational views showing the appearance of a conventional PCR vessel, with (1) in a state where a lid body is opened, and (2) in a state where the lid body is closed.

FIG. 23 A front elevational view and a partially fragmented sectional view showing a central sectional structure of a reagent cassette of the PCR vessel shown in FIG. 22, with (1) in a state before storing reagents, and (2) in a state after storing and sealing the reagents.

FIG. 31 Sectional views showing a central sectional structure around an upper portion of a reagent cassette and a lower portion of a lid body in a PCR vessel according to a fifth embodiment of the present invention, with (1) in a state before the lid body is mounted, and (2) in a state where the lid body is mounted.

FIG. 33 Sectional views, corresponding to FIG. 31, showing the structures of reagent cassettes of PCR vessels according to further embodiments of the present invention.

DESCRIPTION OF EMBODIMENTS

Figure 1:
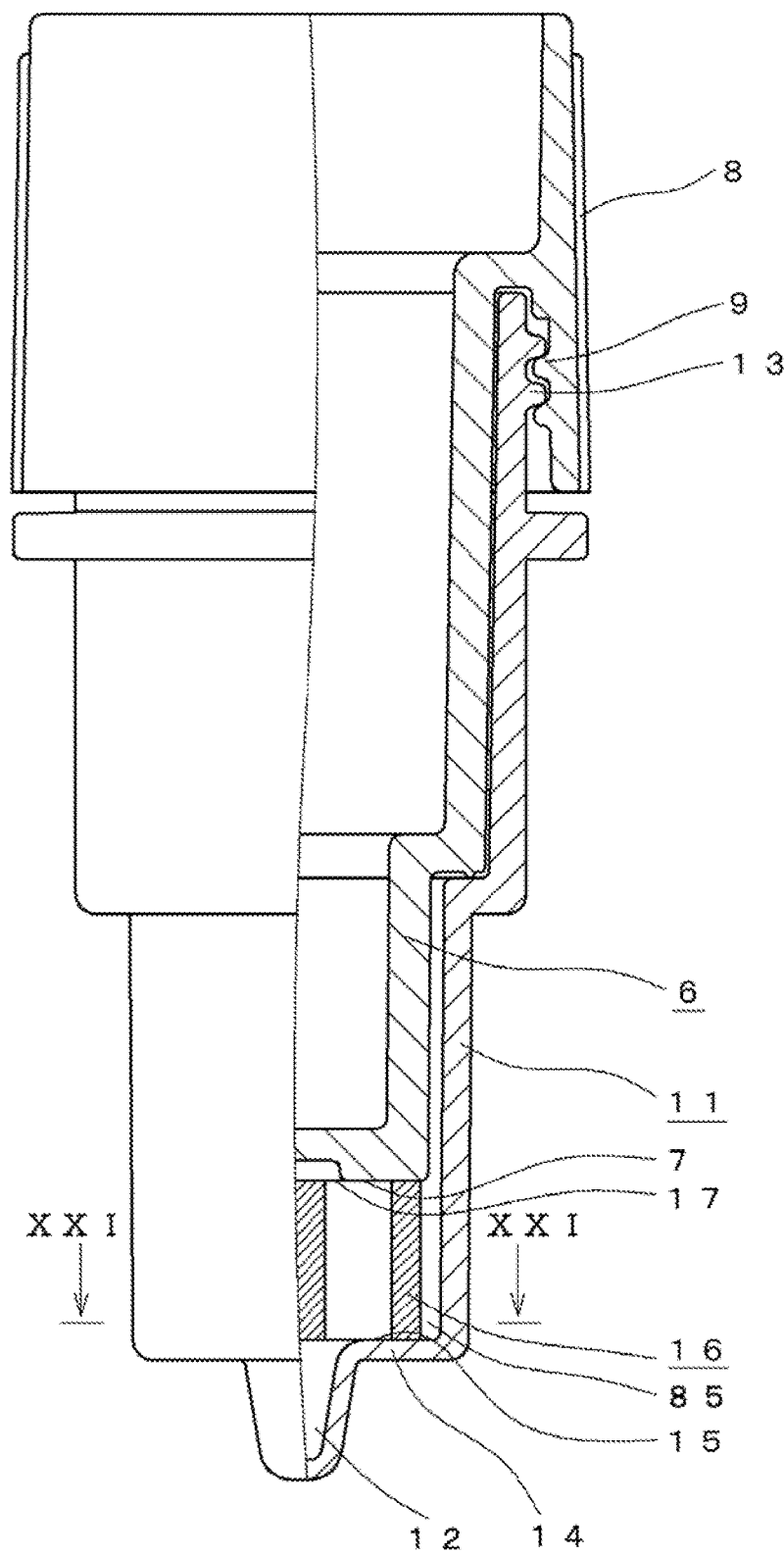
FIG. 1 A front elevational view and a partially fragmented sectional view showing the appearance and a central sectional structure of a PCR vessel according to a first embodiment of the present invention.

FIG. 1 illustrates a front elevational view and a partially fragmented sectional view showing the appearance and a central sectional structure of a PCR vessel according to a first embodiment of the present invention.

Referring to the figure, a PCR vessel 1 is made of transparent polypropylene, for example, has a horizontal section in the shape of a circular ring, and is mainly constituted of a vessel body 11 having a reaction chamber 12 storing and reacting a specimen and reagents at the time of PCR on a bottom portion 14 thereof, a lid body 6 fittable with the vessel body 11 and a reagent cassette 16 stored in a portion between a lower surface 7 of the lid body 6 and the reaction chamber 12 in the vessel body 11. In the figure, the PCR vessel 1 is in a tightly closed state where a male screw portion 13 formed on an outer side surface of an upper portion of the vessel body 11 and a female screw portion 9 formed on an inner side surface of an upper portion of the lid body 6 fit with each other in a screw system, and prevents external infiltration of foreign matter. The lid body 6 can be shifted to an open state released from fitting between the lid body 6 and the vessel body 11 by grasping and rotating a knurling portion 8 on the upper portion thereof, and allows injection of the specimen into the vessel body 11, removal of the reagent cassette 16 from the vessel body 11 or storage thereof in the vessel body 11 in the open state.

When the PCR vessel 1 is in use, the specimen and the reagents are stored and reacted while positioning the reaction chamber 12 on the lowermost portion in the vertical direction shown in FIG. 1. In this specification, an upper direction indicates a direction where the reagent cassette and the lid body are positioned with respect to the reaction chamber at the time of use of the PCR vessel, while a lower direction reversely indicates a direction where the reaction chamber is positioned with respect to the reagent cassette and the lid body at the time of use of the PCR vessel.

In the PCR vessel 1, the reagent cassette 16 is set on a flat portion 15 extending outward from a peripheral edge of the upper end of the reaction chamber 12 on the bottom portion 14 of the vessel body 11 while a part of an upper surface 17 of the reagent cassette 16 and a part of the lower surface 7 of the lid body 6 are in contact with each other without a clearance in the tightly closed state shown in FIG. 1. Thus, the position of the reagent cassette 16 in the PCR vessel 1 is fixed.

Respective components of the PCR vessel 1 are now described.

Figure 2:
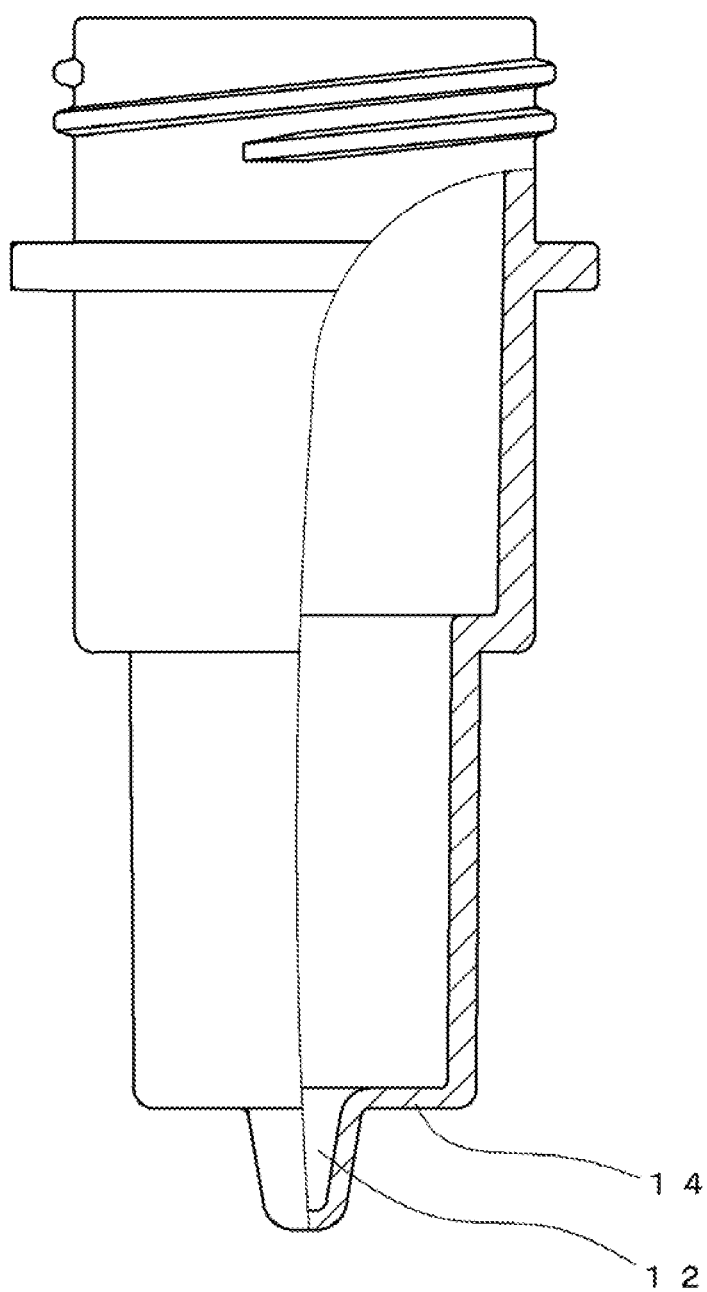
FIG. 2 A front elevational view and a partially fragmented sectional view showing the appearance and a central sectional structure of a vessel body of the PCR vessel shown in FIG. 1.
Figure 3:
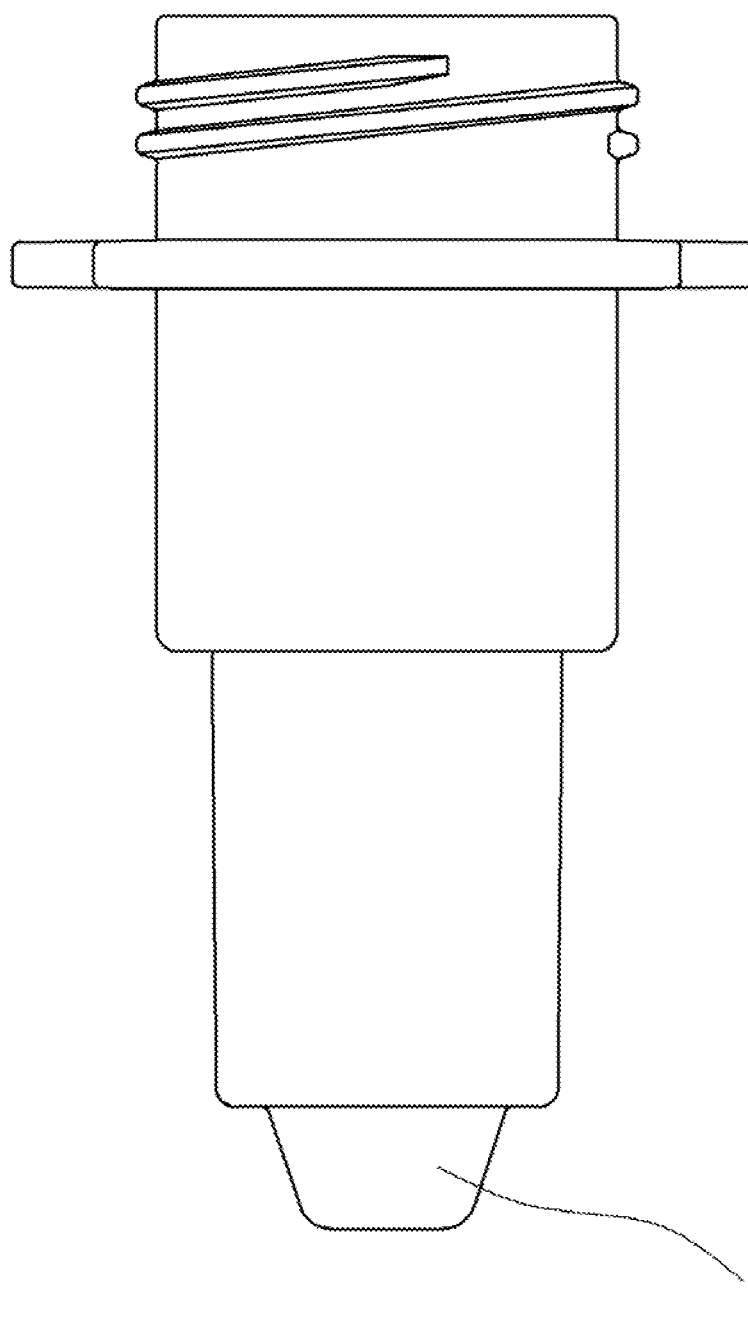
FIG. 3 A side elevational view showing the appearance of the vessel body of the PCR vessel shown in FIG. 1.

FIG. 2 illustrates a front elevational view and a partially fragmented sectional view showing the appearance and a central sectional structure of the vessel body of the PCR vessel shown in FIG. 1, and FIG. 3 is a side elevational view showing the appearance of the vessel body of the PCR vessel shown in FIG. 1.

Referring to these figures, the vessel body 11 has a cylindrical shape whose upper portion is opened, while the reaction chamber 12 provided on the bottom portion 14 thereof is in the shape of a downwardly tapered truncated quadrangular pyramid and made of a transparent material. The vessel body 11 is so structured in this manner that opposed surfaces are formed in the reaction chamber 12. Effects resulting from this are described later.

Figure 4:
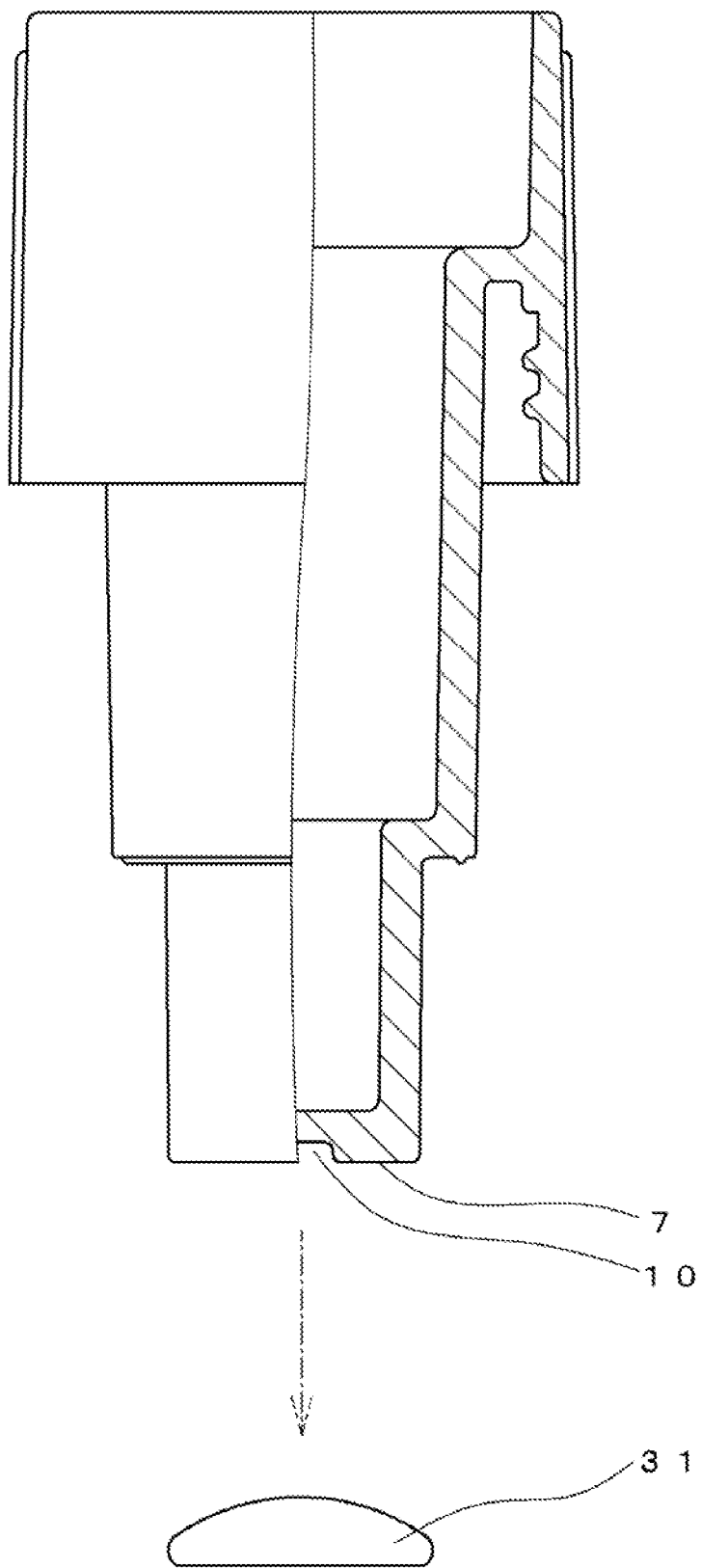
FIG. 4 A front elevational view and a partially fragmented sectional view showing the appearance and a central sectional structure of a lid body of the PCR vessel shown in FIG. 1.

FIG. 4 illustrates a front elevational view and a partially fragmented sectional view showing the appearance and a central sectional structure of the lid body of the PCR vessel shown in FIG. 1.

Referring to the figure, the lid body 6 is made of synthetic resin such as polypropylene, for example, and an upwardly concave recess portion 10 capable of storing at least a part of a specimen 31 through contact therewith is formed on the lower surface 7 thereof. At the time of use, a part (saliva containing target DNA, for example) of the specimen 31 can be simply collected in the recess portion 10 without employing labware or the like by bringing the recess portion 10 of the lid body 6 into contact with the specimen 31 (tunica mucosa oris, for example), as shown by arrow drawn with one-dot chain lines in the figure. Effects resulting from this are described later.

Figure 5:
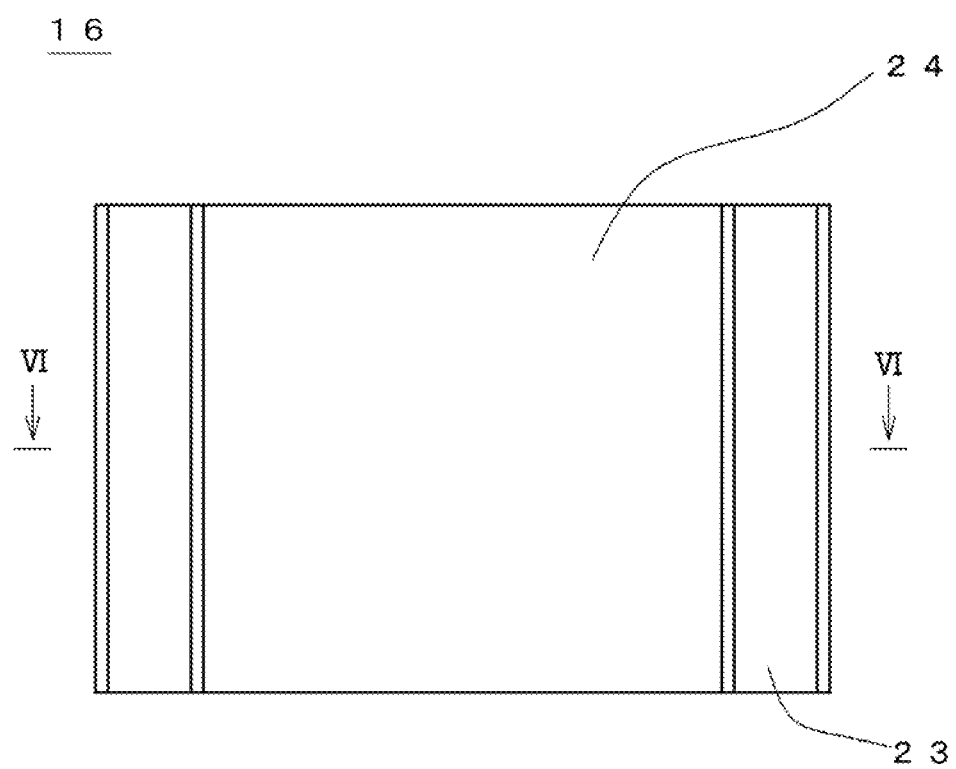
FIG. 5 A front elevational view showing the appearance of a reagent cassette of the PCR vessel shown in FIG. 1.

FIG. 5 is a front elevational view showing the appearance of the reagent cassette of the PCR vessel shown in FIG. 1, and FIG. 6 shows end views along a line VI-VI shown in FIG. 5, with (1) in a state before storing reagents, and (2) in a state after storing and sealing the reagents.

Referring to these figures, the reagent cassette 16 is made of synthetic resin such as polypropylene, for example, and has a basic framework of a cylindrical shape penetrating in the vertical direction, while respective ones of slits 23a to 23c extending in the vertical direction and communicating with respective ones of reagent storing portions 21a to 21c are formed on a sidewall 24 thereof. Effects resulting from this are described later.

Further, the reagent cassette 16 has the reagent storing portions 21a to 21c capable of sealing reagents 32a to 32c with paraffin members 25a to 25c solid before PCR and melted by heating in PCR. The melting point of paraffin is set to about 50° C. In other words, the respective ones of the reagent storing portions 21a to 21c can seal unshown openings in the vertical direction and the slits 23a to 23c with sealing means such as the paraffin members 25a to 25c in a state storing the respective ones of the reagents 32a to 32c. The reagent cassette 16 is so structured in this manner that the paraffin members 25a to 25c or the like are melted while the reagent cassette 16 made of synthetic resin itself is not melted by heating in PCR reaching at least 90° C. at the maximum and the reagent storing portions 21a to 21c are downwardly opened when performing PCR by storing a specimen necessary for PCR in the vessel body 11 in a tightly closed state storing the reagent cassette 16 in the vessel body 11 as shown in FIG. 1 in a state previously storing and sealing the reagents 32a to 32c in the reagent storing portions 21a to 21c as shown at (2) in FIG. 6. Then, the specimen and the reagents 32a to 32c move to the lower reaction chamber 12. Therefore, the PCR vessel according to the present invention is simple since no labware such as a micropipette is employed, stable since the reagent cassette has the basic framework (sidewall) made of synthetic resin, and can improve reliability and rapidity of PCR by removing trouble of reagent injection by an experimenter and preventing measurement errors and contamination with foreign matter.

When storing the reagents, paraffin is laid by pressing an unshown lower opening of the reagent cassette 16 and the slits 23a to 23c against the paraffin in a melted state and thereafter cooling the same, and prescribed quantities of reagents 32a to 32c are stored from above with an unshown automatic dispenser, whereafter the upper opening of the reagent cassette 16 is also filled up with paraffin to be sealed.

Further, the recess portion 10 is formed on the lower surface 7 of the lid body 6 and the reagent storing portions 21a to 21c have shapes penetrating in the vertical direction as described above with reference to FIG. 4, whereby the reagent storing portions 21a to 21c penetrate in the vertical direction when the paraffin members 25a to 25c are melted by heating in PCR. A part of the upper surface 17 of the reagent cassette 16 and a part of the lower surface 7 of the lid body 6 are in contact with each other without a clearance as described above with reference to FIG. 1, whereby the specimen moves from the recess portion 10 to the reagent storing portions 21a to 21c, and the specimen and the reagents 32a to 32c move to the lower reaction chamber 12 through the reagent storing portions 21a to 21c. Therefore, simplicity, reliability and rapidity of PCR can be further improved.

The reagent cassette 16 is provided with the plurality of reagent storing portions 21a to 21c, which are separated from each other by the respective ones of the partition walls 22a to 22c. The partition walls 22a to 22c are platelike bodies extending from the unshown upper surface to the lower surface of the reagent cassette 16 in the vertical direction, arranged to mutually form an angle of 120° in plan view, and separate the reagent storing portions 21a to 21c to have identical volumes. Thus, the reagents 32a to 32c stored in the respective ones of the reagent storing portions 21a to 21c can be sealed in a state not mixed with each other as shown at (2) in the figure. Therefore, reagents not suitable to be previously mixed with each other can be easily employed.

The reagents are reagents necessary for PCR, desired types may be selected in response to the use, and water, a buffer solution, a primer, dNTP, a magnesium compound, DNA polymerase, a fluorescent reagent and the like can be listed, for example. While the fluorescent reagent is not necessary for PCR itself, embodiments of the present invention are described in a state including the fluorescent reagent for the purpose of simultaneously performing photodetection in a DNA detector after completion of PCR.

Further, the reagent cassette 16 has a tubular shape opened in the vertical direction as described above, and the respective ones of the slits 23a to 23c extending in the vertical direction and communicating with the respective ones of the reagent storing portions 21a to 21c are formed on the sidewall 24 thereof. Thus, the surface area of a portion of the reagent cassette 16 from which the reagents 32a to 32c flow out increases, whereby the reagents 32a to 32c can easily fall from the reagent cassette 16 toward the reaction chamber 12.

A process of progressing PCR with the DNA detector by employing the PCR vessel 1 storing the specimen and the reagents is now described.

Figure 7:
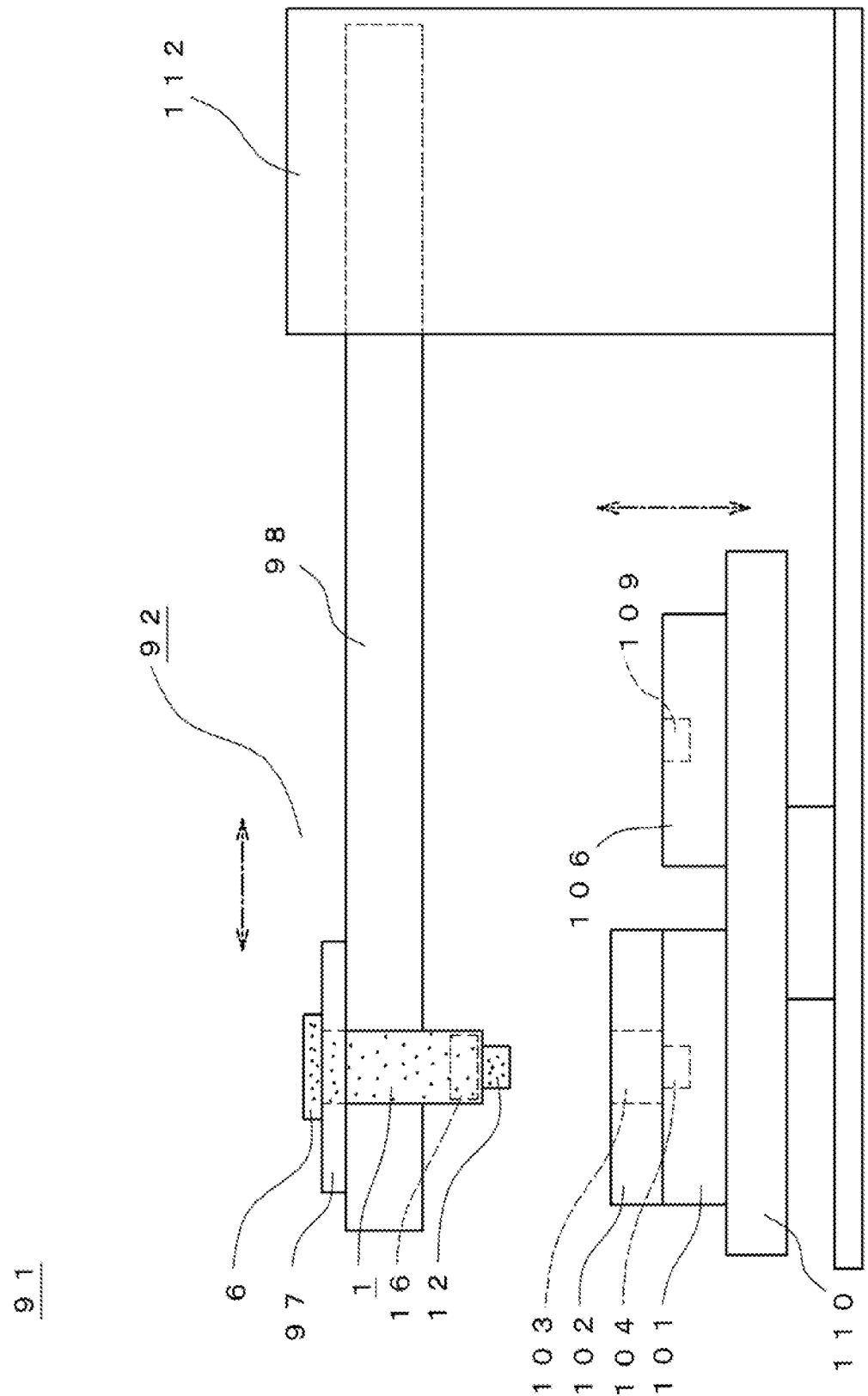
FIG. 7 A schematic front elevational view showing a state before operation of a DNA detector employing the PCR vessel shown in FIG. 1.

FIG. 7 is a schematic front elevational view showing a state before operation of the DNA detector employing the PCR vessel shown in FIG. 1.

Referring to the figure, a DNA detector 91 is mainly constituted of a DNA amplifying structure 92 progressing PCR by performing heating and cooling, a detecting portion 112 measuring PCR products stored in the PCR vessel completing PCR by photodetection and a control portion (not shown).

The DNA amplifying structure 92 is mainly constituted of a vessel holder 97 holding the PCR vessel 1, a support portion 98 supporting the vessel holder 97, a plate-shaped first heater 101 on a high-temperature side, a ring plate-shaped heating plate 102 fixed to an upper portion of the first heater 101, a plate-shaped second heater 106 on a low-temperature side and a seat 110 fixing the first heater 101 and the second heater 106 to an upper surface thereof.

The PCR vessel 1 is tightly closed with the lid body 6 in the state storing the reagent cassette 16 storing the reagents as described above and storing the specimen with the recess portion 10 of the lid body 6 or by a manual operation.

The vessel holder 97 holds the PCR vessel 1 so that the bottom surface of the PCR vessel 1 (the reaction chamber 12) is flush with the surfaces of the first heater 101 and the second heater 106.

The support portion 98 is configured to support the vessel holder 97. Following an instruction from the control portion, the support portion 98 can slide the vessel holder 97 in the vertical direction (the direction from the first heater 101 to the second heater 106 or the inverse direction thereof, and the direction from these to the detecting portion 112 or the inverse direction thereof) as shown by arrow in a one-dot chain line in the upper portion of the figure, whereby the PCR vessel 1 can be freely moved to a portion above the first heater 101, a portion above the second heater 106 or the detecting portion 112.

The first heater 101 is formed by a heating body covered with silicone rubber, for example, so configured that the temperature thereof is adjustable by the control portion, and has a recess 104 into which the reaction chamber 12 of the PCR vessel 1 is fittable on an upper surface thereof. The surface of the recess 104 is set to a high temperature of 120° C., for example, by the control portion.

The heating plate 102 is made of aluminum having high heat conductivity, for example, and has a through-hole 103 into which the PCR vessel 1 is insertable on a central portion thereof. The thickness of the heating plate 102 is substantially identical to the vertical height of the reagent cassette 16. The inner surface of the through-hole 103 is warmed up by heat conduction from the first heater 101 to reach 80° C., for example.

The second heater 106, similar to the aforementioned first heater 101 except for the temperature, is formed by a heating body covered with silicone rubber, for example, so configured that the temperature thereof is adjustable by the control portion, and has a recess 109 into which the reaction chamber 12 of the PCR vessel 1 is fittable on an upper surface thereof. The surface of the recess 109 is set to a low temperature of 50° C., for example, by the control portion.

The seat 110 is such that the first heater 101 and the second heater 106 are fixed to an upper surface thereof. Further, the seat 110 is controlled by the control portion to be slidable in the vertical direction (the direction from the reaction chamber 12 toward the recess 104 in a state before operation in FIG. 7 or the inverse direction thereof) as shown by arrow drawn in a one-dot chain line on a lower portion of the figure. Thus, the first heater 101 and the second heater 106 are ascendable or descendable.

Figure 8:
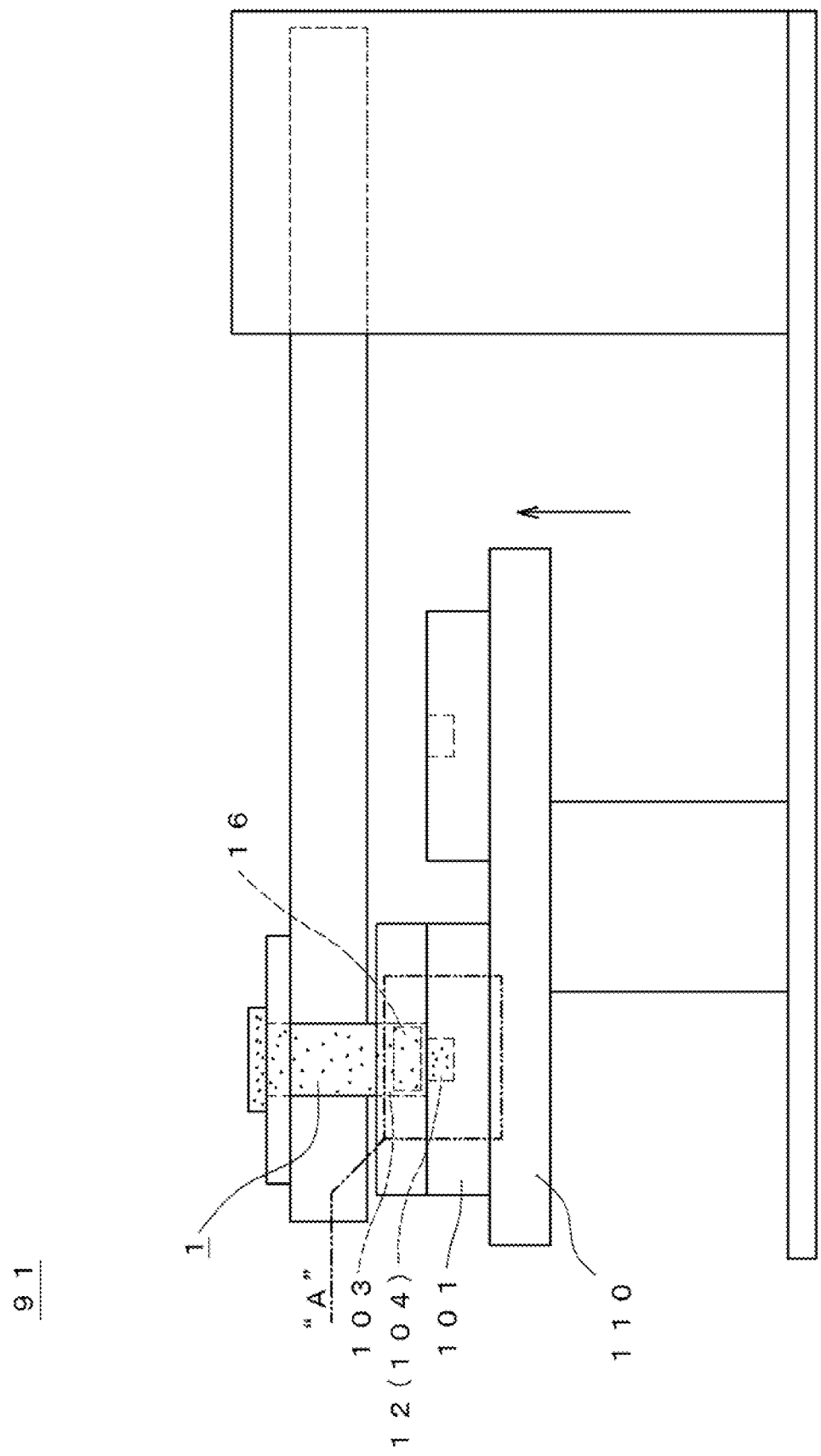
FIG. 8 A schematic front elevational view, corresponding to FIG. 7, showing an operating state of the DNA detector.

FIG. 8 is a schematic front elevational view, corresponding to FIG. 7, showing an operating state of the DNA detector.

Referring to the figure, the seat 110 first ascends in a direction of arrow drawn in a solid line in the figure from the state before operation shown in FIG. 7 following an instruction from the control portion, whereby the PCR vessel 102 passes through the through-hole 103 of the heating plate 102 while the reaction chamber 12 of the PCR vessel 1 fits into the recess 104 of the first heater 101.

Then, the portion of the PCR vessel 1 in which the reagent cassette 16 is stored is warmed up through the through-hole 103 by heating in PCR to melt the paraffin members on upper and lower portions of the reagent cassette 16, and to discharge the reagents or the specimen therein to the lower reaction chamber 12 (see also FIG. 9 described later). Further, the specimen and the reagents stored in the reaction chamber 12 of the PCR vessel 1 are heated through contact (first contact) between the surface of the reaction chamber 12 of the PCR vessel 1 and the surface of the recess 104 of the first heater 101.

The state of heating of the specimen and the reagents through this first contact is described in detail.

Figure 9:
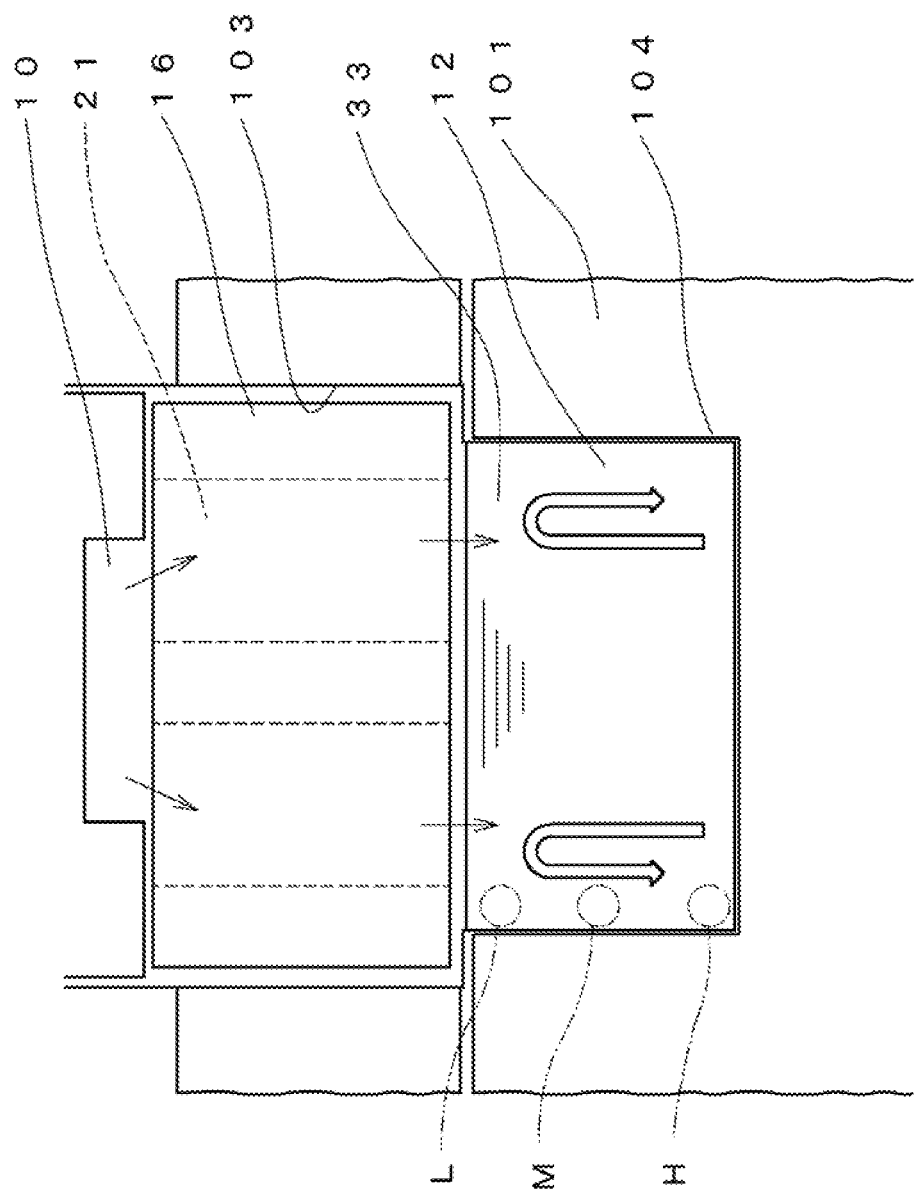
FIG. 9 A typical drawing of a portion A shown in FIG. 8.

FIG. 9 is a typical drawing of a portion A shown in FIG. 8.

Referring to the figure, the reagent cassette 16 first enters a state penetrating in the vertical direction since the paraffin members on the unshown upper and lower surfaces are melted by heating through the through-hole 103 as described above. Therefore, the specimen having been stored in the recess 10 moves to the reagent storing portion 21, as shown by arrow drawn in a solid line in the figure. Further, the specimen and the reagents having been stored in the reagent storing portion 21 move to the reaction chamber 12 and form a PCR solution 33 corresponding to the specimen and the reagents necessary for PCR.

The first heater 101, having the surface made of silicone rubber, is excellent in elasticity (shape recoverability from compressive deformation) and heat conductivity. In the first contact, therefore, the reaction chamber 12 fits into the recess 104 with high adhesiveness, and the PCR solution 33 is heated through direct heat conduction from the first heater 101 to the reaction chamber 12.

In addition thereto, an upper portion of the PCR solution 33 shown by L is at a relatively low temperature in the PCR solution 33 in heating since the same is outward, a lower portion of the PCR solution 33 shown by H is at a relatively high temperature since the same is a portion to which heat from the first heater 101 is strongly conducted, and a middle portion of the PCR solution 33 shown by M is at a temperature substantially intermediate between L and H. Thus, the heated solution in the lower portion starts ascending, and causes convection turning back on the top water surface, as shown by arrows in the figure. The PCR solution 33 is efficiently heated due to this heat convection. The PCR solution 33 is heated to 92° C., for example, and alteration of DNA is performed due to the first contact.

When the heating through the first contact by a prescribed time is completed, the seat 110 descends following an instruction from the control portion, is released from the first contact and returns to the state shown in FIG. 7. While illustration is omitted in the following, the support portion 98 thereafter horizontally moves the vessel holder 97 so that the PCR vessel 1 comes to a position above the second heater 106 following an instruction from the control portion.

Similarly to the case of the first contact described above with reference to FIG. 8, the seat 110 so ascends that the reaction chamber 12 of the PCR vessel 1 fits into the recess 109 of the second heater 106, to result in contact (second contact) between the surface of the reaction chamber 12 of the PCR vessel 1 and the surface of the recess 109 of the second heater 106. The PCR solution 33 is cooled to 65° C., for example, due to this second contact, and annealing is performed.

When cooling through the second contact by a prescribed time is completed, the seat 110 descends following an instruction from the control portion, the vessel holder 97 horizontally moves through the support portion 98, and the PCR vessel 1 returns to the state shown in FIG. 7 in which the same is positioned above the first heater 101.

The first contact and the second contact are alternately repeated in this manner, thereby PCR progresses. When the first contact and the second contact are repeated by a prescribed number of times and the PCR is completed, the process advances to a step of detecting amplified DNA.

Figure 10:
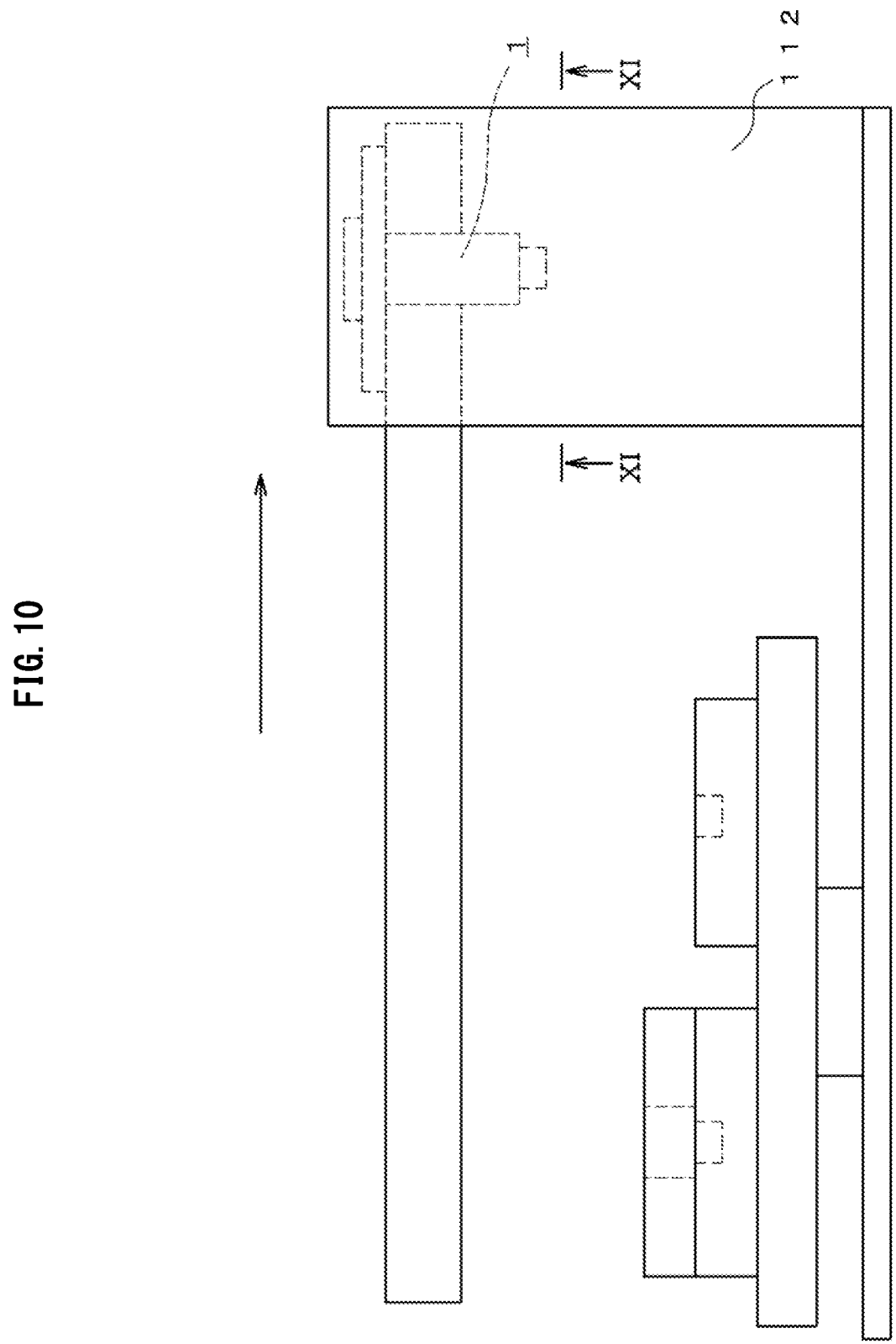
FIG. 10 A schematic front elevational view, corresponding to FIG. 7, showing a state where PCR is completed and the PCR vessel moves to a detecting portion.

FIG. 10 is a schematic front elevational view, corresponding to FIG. 7, showing a state where PCR is completed and the PCR vessel moves to the detecting portion.

Referring to the figure, the support portion 98 moves the vessel holder 97 in a direction shown by arrow in the figure following an instruction from the control portion after PCR is completed, whereby the PCR vessel 1 moves to the detecting portion 112.

Figure 11:
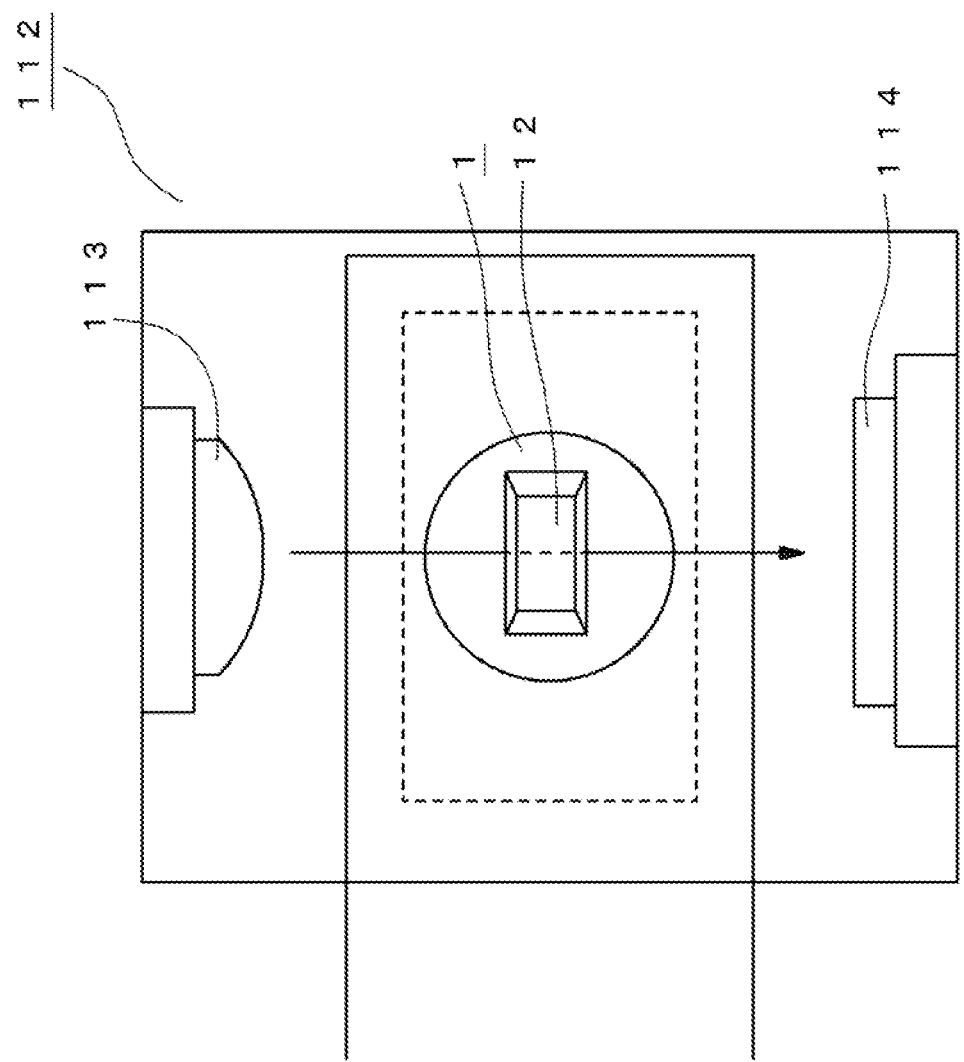
FIG. 11 A drawing seen along a line XI-XI shown in FIG. 10.

FIG. 11 is a drawing seen along a line XI-XI shown in FIG. 10.

Referring to the figure, the detecting portion 112 is mainly constituted of a light emitter 113 and a photodetector 114. The light emitter 113 and the photodetector 114 are arranged to face each other on a coaxial straight line in the horizontal direction. The PCR vessel 1 is so positioned that this straight line passes through the reaction chamber 12 in which amplified DNA is stored. The light emitter 113 is an LED lamp whose effective wavelength is 450 nm to 570 nm. The photodetector 114 is a photodiode whose effective wavelength is 300 nm to 820 nm.

In detection, the light emitter 113 emits excitation light toward the reaction chamber 12 of the PCR vessel 1 following an instruction from the control portion (not shown). The amplified DNA in the reaction chamber 12 is bonded to the fluorescent reagent included in the reagents, and reacts to the excitation light to fluoresce. The reaction chamber 12 transmits light since the same is made of a transparent material, so that the photodetector 114 can receive the light emission intensity of the fluorescing DNA. Thus, photodetection of the DNA is possible without transferring PCR products from the PCR vessel to another detection vessel. Then, quantitative measurement of the amplified DNA can be performed on the basis of the received light emission intensity.

Opposed surfaces are formed in the reaction chamber since the reaction chamber 12 of the PCR vessel 1 is in the shape of a truncated quadrangular pyramid and made of a transparent material as described above, thereby improving reliability in photodetection in a case of performing photodetection in the horizontal direction with respect to the reaction chamber after PCR.

As described above, the PCR vessel 1 makes it possible to simply and stably improve reliability and rapidity of PCR since the same includes the reagent cassette 16, and also makes it possible to easily and safely obtain stable measurement results even if the operator is not skilled due to synergistic effects with the recess portion 10 on the lower surface 7 of the lid body 6.

Further, such a reagent cassette 16 can also be stored in the PCR vessel 1 in a state where the reagents are previously stored in the reagent storing portion 21 thereof and sealed with sealing means such as paraffin. The reagent cassette is so structured in this manner that the reagents are previously stored and sealed in the reagent cassette, whereby desired quantities and types of reagents can be previously stored, and reliability and rapidity of PCR can be simply and stably improved by employing the reagent cassette for the PCR vessel.

Figure 12:
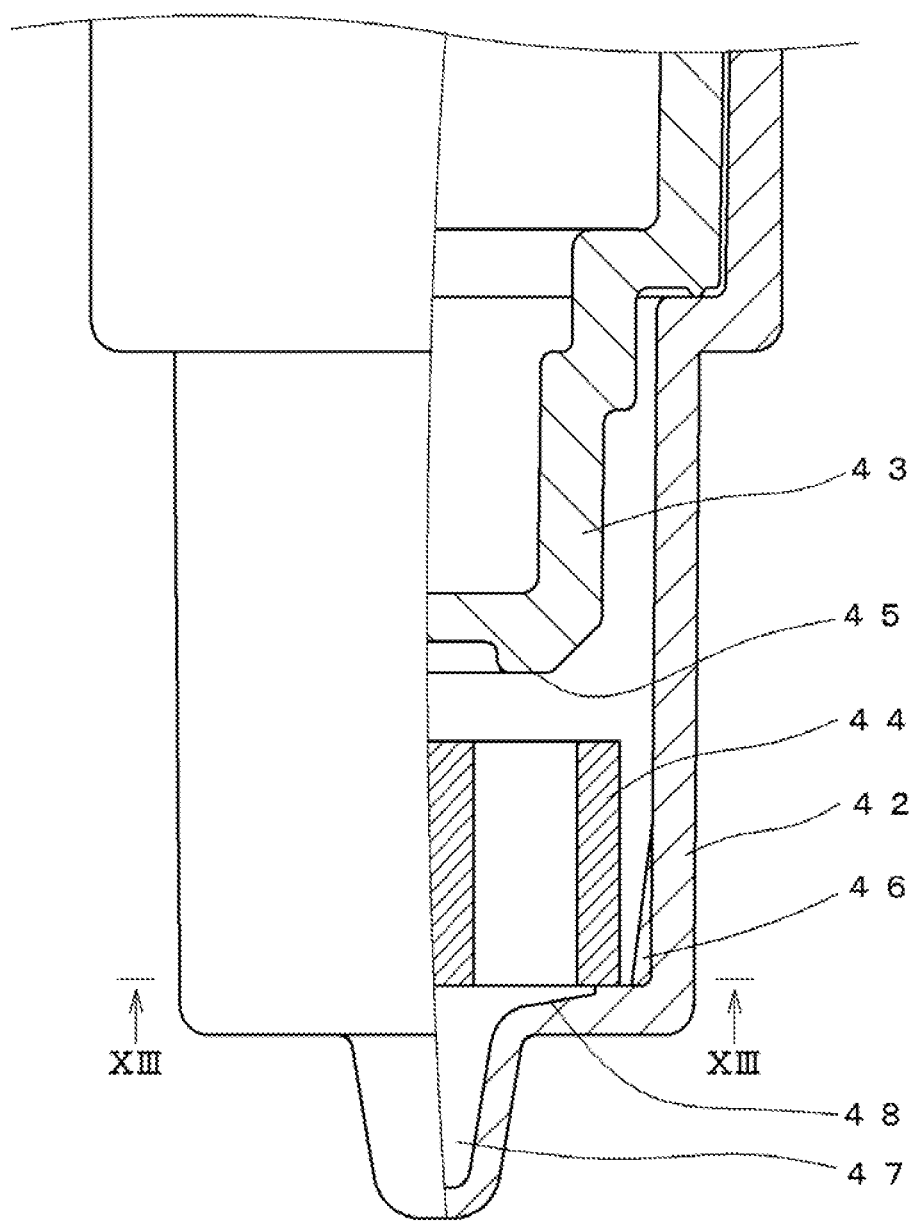
FIG. 12 A front elevational view and a partially fragmented sectional view showing the appearance and a central sectional structure of a lower half portion of a PCR vessel according to a second embodiment of the present invention.
Figure 13:
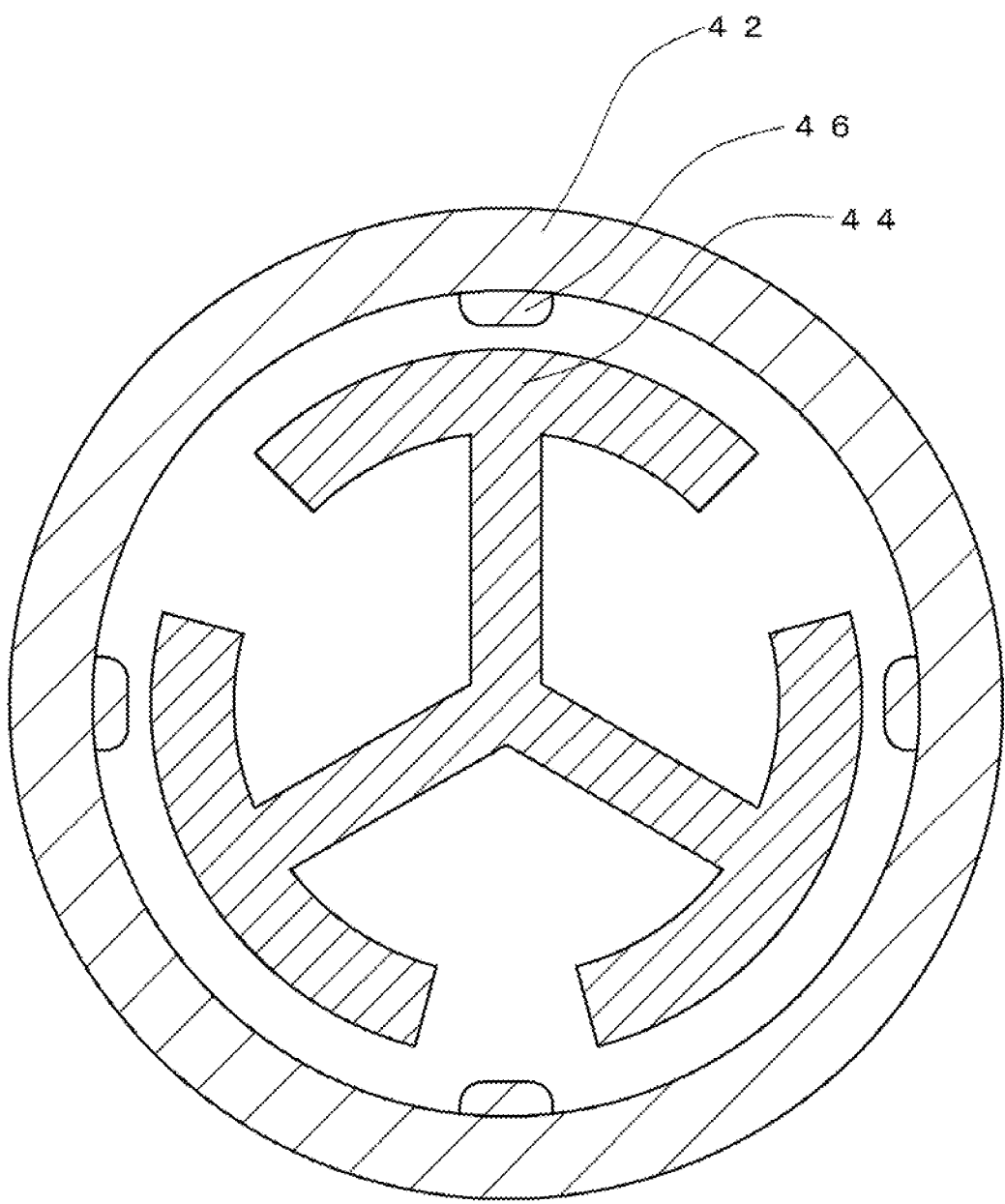
FIG. 13 An end view along a line XIII-XIII shown in FIG. 12.

FIG. 12 illustrates a front elevational view and a partially fragmented sectional view showing the appearance and a central sectional structure of a lower half portion of a PCR vessel according to a second embodiment of the present invention, and FIG. 13 is an end view along a line XIII-XIII shown in FIG. 12.

The basic structure of this PCR vessel 41 is similar to that of the PCR vessel 1 according to the first embodiment, and hence the same is described mainly with reference to different points.

Referring to these figures, a vessel body 42, a lid body 43 and a reagent cassette 44 are set in such a dimensional relation that a clearance is formed between a lower surface 45 of the lid body 43 and the reagent cassette 44 when the lid body 43 fits with the vessel body 42 as shown in FIG. 12. The PCR vessel 41 is so structured in this manner that the clearance is sealable with sealing means at the time of use, whereby such apprehension that stored reagents leak out decreases as compared with the case (the aforementioned first embodiment) of setting the dimensional relation so that no clearance is formed between the lower surface 45 of the lid body 43 and the reagent cassette 44 when the lid body 43 is fitted and the reagent cassette 44 is pressed in the vertical direction.

In the vessel body 42, a rib 46 forming a part of the inner surface thereof inwardly projects toward the reagent cassette 44. The vessel body 42 is so structured in this manner that positioning of the reagent cassette 44 in the vessel body 42 is simplified, whereby the reagent cassette 44 can be induced to a central position where reagents easily fall from the same into a reaction chamber 47, and reliability of PCR is improved.

The inner surface of a bottom portion 48 of the vessel body 42 downwardly inclines from a portion inward beyond the rib 46 toward the reaction chamber 47. Thus, the reagents easily fall from the reagent cassette 44 positioned by the rib 46 into the reaction chamber 47, whereby reliability of PCR is further improved.

Figure 14:
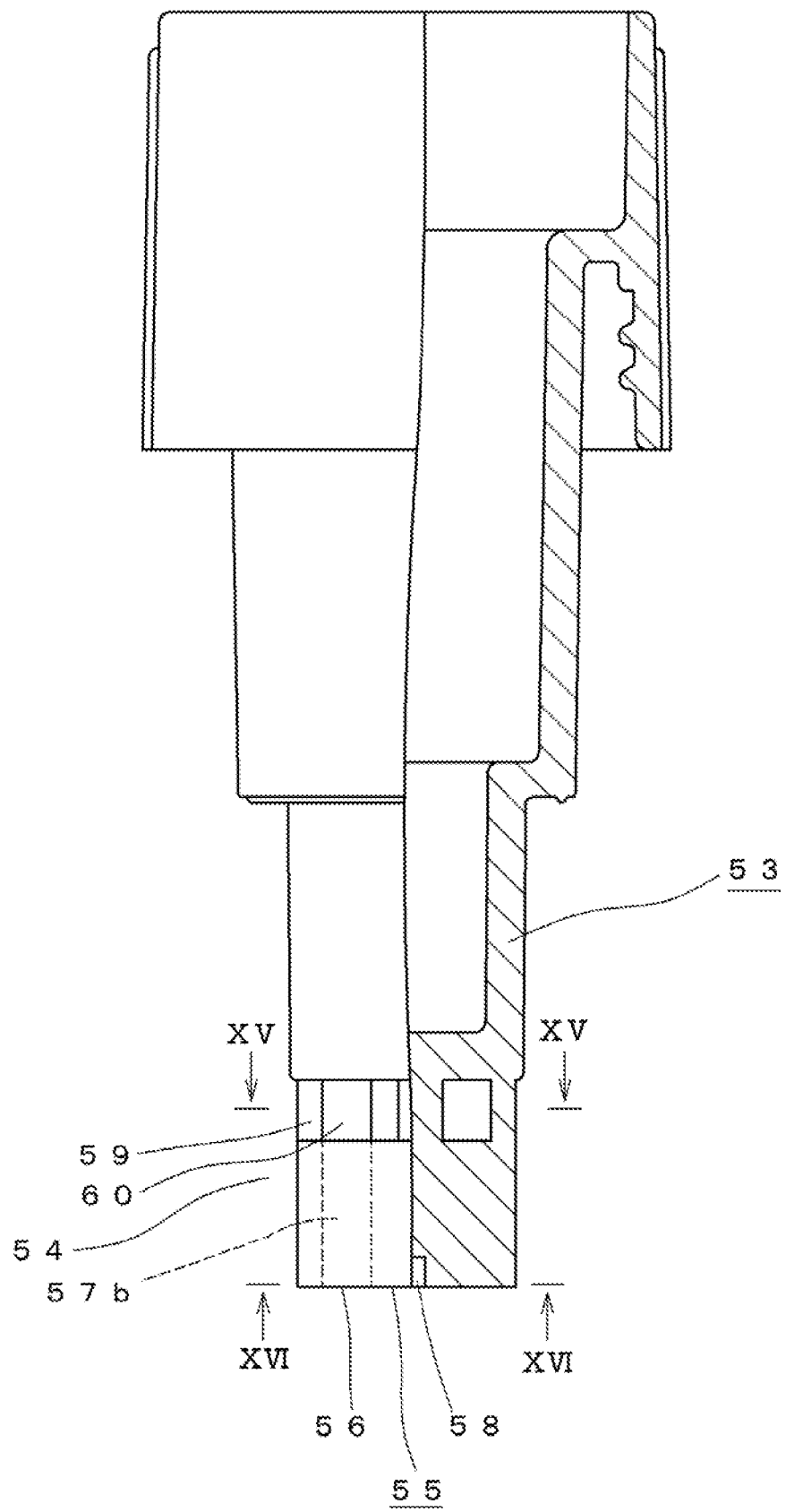
FIG. 14 A front elevational view and a partially fragmented sectional view showing the appearance and a central sectional structure of a lid body of a PCR vessel according to a third embodiment of the present invention.
Figure 16:
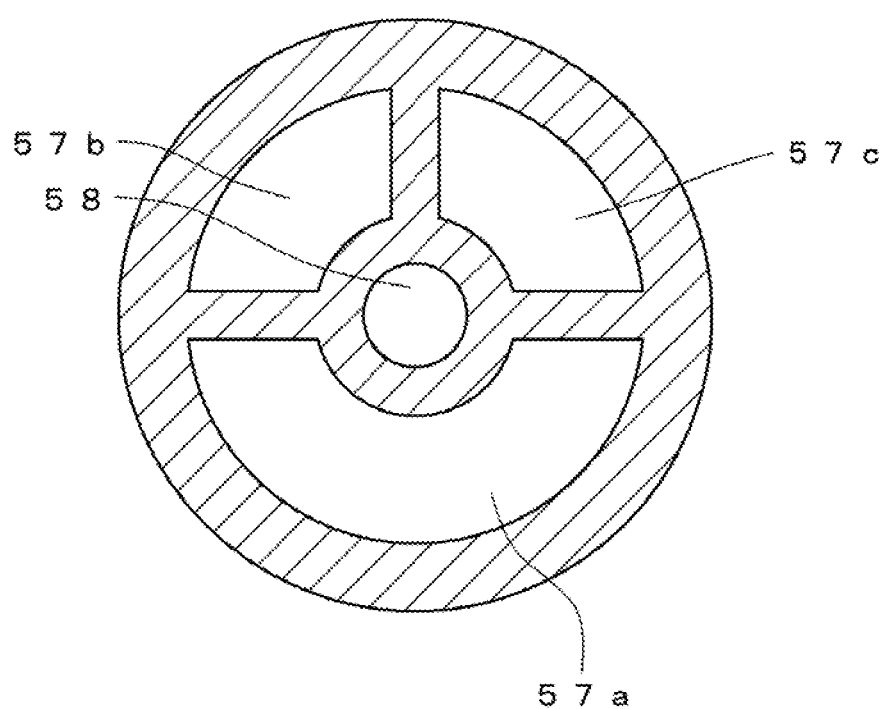
FIG. 16 An end view along a line XVI-XVI shown in FIG. 14.

FIG. 14 illustrates a front elevational view and a partially fragmented sectional view showing the appearance and a central sectional structure of a lid body of a PCR vessel according to a third embodiment of the present invention, FIG. 15 illustrates sectional views along a line XV-XV shown in FIG. 14, with (1) in a state before storing reagents and (2) in a state after storing and sealing the reagents, and FIG. 16 is an end view along a line XVI-XVI shown in FIG. 14.

The basic structure of this PCR vessel according to the third embodiment is similar to that of the PCR vessel 1 according to the first embodiment, and hence the same is described mainly with reference to different points.

Referring to these figures, a lid body 53 has a shape integrated with a reagent cassette on a forward end portion 54 thereof.

In other words, the unshown PCR vessel according to this third embodiment includes an unshown vessel body having a reaction chamber storing and reacting a specimen and reagents at the time of PCR on a bottom portion thereof and the lid body 53 fittable with the vessel body, the lid body 53 has reagent storing portions 57a to 57c formed on the forward end portion 54 through an exposed portion 56 corresponding to a part of a lower surface 55 of the forward end portion 54, an upwardly concave recess portion 58 capable of storing at least a part of the specimen through contact with the same is formed on another part of the lower surface 55 of the forward end portion 54, and the reagent storing portions 57a to 57c can seal the exposed portion 56 with sealing means solid before PCR and melted by heating in PCR.

The PCR vessel is so structured in this manner that the sealing means is melted by heating in PCR and the reagent storing portions 57a to 57c and the recess portion 58 are downwardly opened when storing the specimen by employing the recess portion 58 on the lower surface 55 of the lid body 53 and performing PCR in a state previously storing and sealing the reagents in the reagent storing portions 57a to 57c. Then, the specimen and the reagents move to an unshown lower reaction chamber. Therefore, the PCR vessel can simply and stably improve reliability and rapidity of PCR.

An opening 60 penetrating the reagent storing portion 57 is formed on a sidewall 59 of the forward end portion 54. Thus, the reagents can be injected from the opening 60 formed on the sidewall 59 of the forward end portion 54 toward the reagent storing portion 57, whereby availability is improved.

In other words, the lower surface 55 of the forward end portion 54 of the lid body 53 is first sealed with paraffin 61 in a melted state to seal the exposed portion 56 at the time of use of the PCR vessel according to this third embodiment. Even if the paraffin 61 enters the recess portion 58 at this time, no problem arises so far as a portion of an upwardly concave state remains. Then, after the reagents are injected from the opening 60 into the reagent storing portion 57, the opening 60 is sealed with the paraffin 61, whereby the reagent storing portion 57 enters a state where the reagents are sealed as shown at (2) in FIG. 15.

FIG. 17 illustrates schematic plan views of reagent cassettes of PCR vessels according to other embodiments of the present invention.

Referring to the figure, a reagent cassette 63 shown at (1) has a shape similar to that of the forward end portion according to the third embodiment. A reagent storing portion is divided by partition walls into three portions at volume ratios of 1:1:2. Storage quantities of the reagents can be properly distributed at the time of use as compared with the first embodiment.

In a reagent cassette 64 shown at (2), a reagent storing portion is divided into four sections at volume ratios of 1:1:1:1 by partition walls.

In a reagent cassette 65 shown at (3), a reagent storing portion is divided into five sections by four partition walls not passing through the center but forming rhomboids.

In a reagent cassette 66 shown at (4), a reagent storing portion is divided into four sections by three partition walls forming three parallel lines at regular intervals.

In a reagent cassette 67 shown at (5), a reagent storing portion is divided into a plurality of sections in a meshy manner by a plurality of partition walls.

In a reagent cassette 68 shown at (6), a plurality of reagent storing portions vascularly penetrate the reagent cassette 68 solid in a portion excluding the reagent storing portions in the vertical direction. In this case, the solid portion of the reagent cassette 68 functions as a partition wall.

The aforementioned modes of (1) to (6) are also applicable to any of the reagent cassettes (the forward end portion of the lid body in the case of the third embodiment) according to the first to third embodiments. It is also possible to apply these modes while changing the spatial angles between these partition walls, changing the vertical angles of the respective ones of the partition walls, or combining the division modes with these partition walls. Further, slits may be formed on sidewalls of the respective reagent cassettes.

Figure 18:
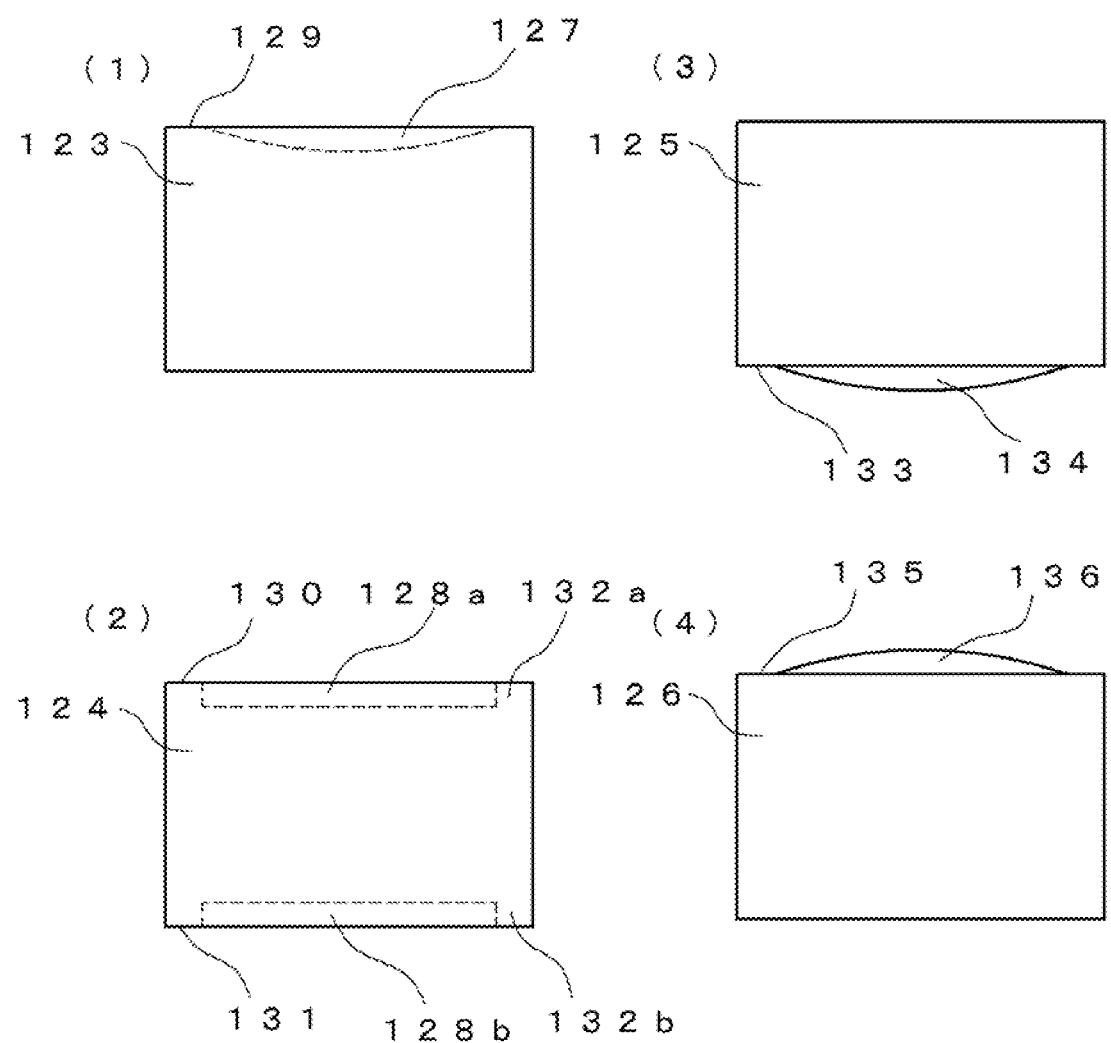
FIG. 18 Schematic front elevational views of reagent cassettes of PCR vessels according to further embodiments of the present invention.
Figure 20:
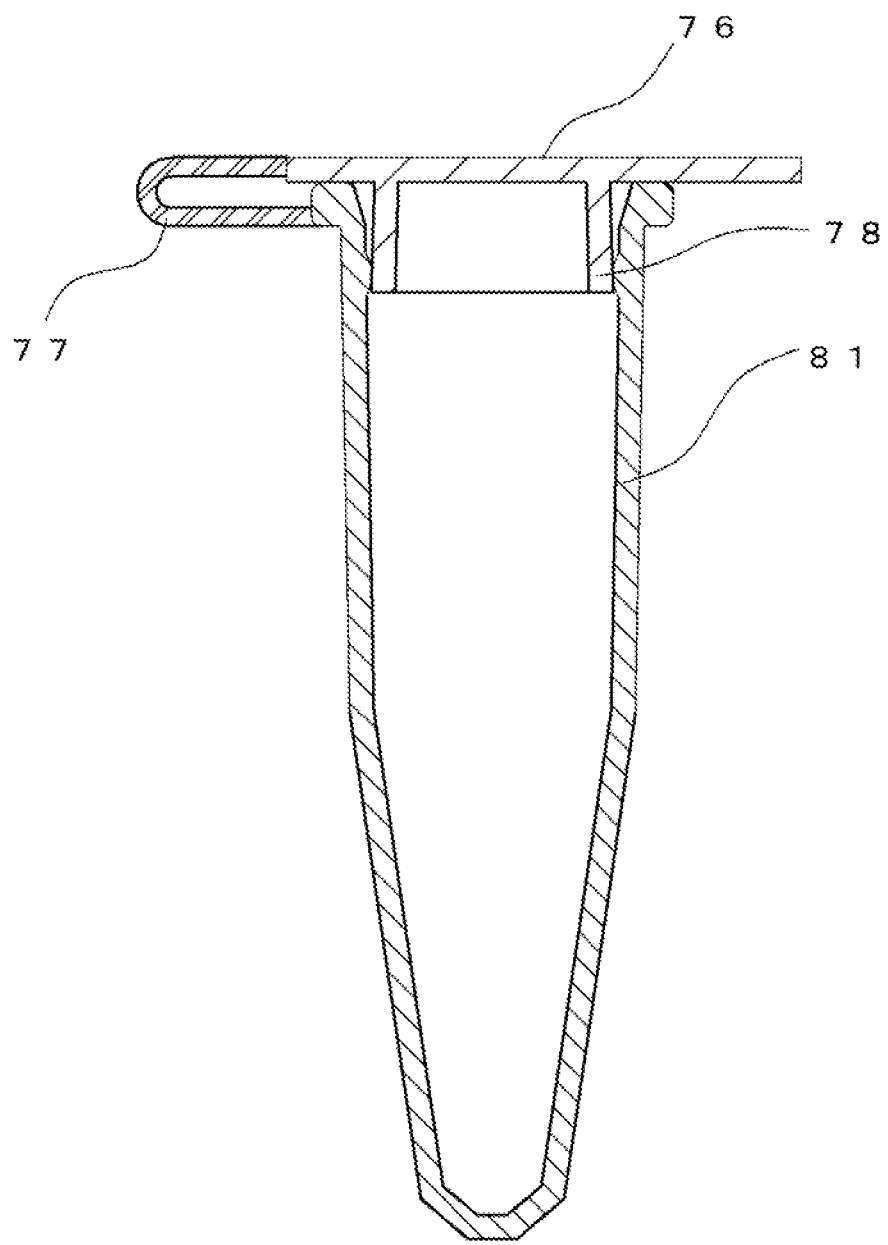
FIG. 20 A sectional view showing a central sectional structure in the state where the lid body of the PCR vessel is closed as shown at (2) in FIG. 19.

FIG. 18 illustrates schematic front elevational views of reagent cassettes of PCR vessels according to further embodiments of the present invention.

Referring to the figure, an inwardly (downwardly) concave recess portion 127 is formed on an upper surface 129 of a reagent cassette 123 at (1). An inwardly (upwardly) concave recess portion may be similarly formed on a lower surface, or recess portions may be formed on an upper surface 130 and a lower surface 131 as in a reagent cassette 124 shown at (2). When structuring the reagent cassette in this manner, the inwardly concave portion is formed on the upper surface or the lower surface of the reagent cassette, whereby sealing means such as paraffin easily remains in the recess portion at the time of sealing, and reliability of sealing with the sealing means is improved.

The reagent cassette 124 at (2) has such a mode that outwardly projecting full-peripheral ribs 132a and 132b are formed on peripheral edges of the respective ones of the upper surface 130 and the lower surface 131.

A downwardly convex projecting portion 134 is formed on a lower surface 133 of a reagent cassette 125 at (3). The reagent cassette is so structured in this manner that the lower surface of the reagent cassette is not horizontal but convex toward a reaction chamber, whereby reagents easily fall into the reaction chamber as compared with a case where the lower surface is horizontal, and reliability of PCR is improved.

An upwardly convex projecting portion 136 is formed on an upper surface 135 of a reagent cassette 126 at (4). In the PCR vessel 1 according to the first embodiment, for example, the recess portion 10 is formed on the lower surface 7 of the lid body 6 as described above, and the reagent storing portion 21 has the shape penetrating in the vertical direction. The projecting portion 136 is set to enter at least a part of the recess portion 10 when the lid body 6 fits with the vessel body 11. The reagent cassette is so structured in this manner that a specimen stored in the recess portion on the lower surface of the lid body can be easily scraped out at the time of use, whereby the specimen easily reaches the reaction chamber, and reliability of PCR is improved.

Outwardly (upwardly on the upper surface of the reagent cassette and downwardly on the lower surface of the reagent cassette) convex projecting portions may be formed on both of the upper surface and the lower surface of the reagent cassette. A case where the reagent cassette has a spherical shape is also included in this.

While the reagent cassette has had a cylindrical shape in each of the aforementioned embodiments, the same may have another shape. For example, the reagent cassette may have a tubular shape with a polygonal ring-shaped section, or a spherical shape. While the reagent cassette preferably has a cylindrical shape in view of ensuring orientation at a time of being stored in the vessel body, the present invention can be suitably carried out by making orientation unnecessary by providing a large number of through-holes in a plurality of directions such as upper, lower, left and right directions also in the case of a spherical shape, for example.

While the PCR vessel as well as the vessel body, the lid and the reagent cassette constituting the same have had specific shapes in each of the aforementioned embodiments, the same may have other shapes. The volumes thereof may be varied in response to the use, for example.

While the reagent cassette has had a plurality of reagent storing portions and the plurality of reagent storing portions have been separated from each other by the partition wall in each of the aforementioned embodiments, the reagent cassette may simply have at least one reagent storing portion.

Further, while the recess portion has been formed on the lower surface of the lid body in each of the aforementioned embodiments, the recess portion may not be formed. The present invention is applicable also to a case of manually introducing a specimen so far as the PCR vessel includes the reagent cassette.

While the reagent storing portion has penetrated in the vertical direction in each of the aforementioned embodiments, the same may be exposed at least in one direction.

While the slit has been formed on the sidewall of the reagent cassette to extend in the vertical direction and to part the sidewall in each of the aforementioned embodiments, the slit may simply be formed to communicate with at least the reagent storing portion. Further, the slit may not be formed.

While the reaction chamber has been in the shape of a truncated quadrangular pyramid and made of a transparent material in each of the aforementioned embodiments, the reaction chamber may have another shape such as a downwardly convex semispherical shape, for example, and the present invention can be applied without influencing PCR itself even if the reaction chamber is not made of a transparent material.

While four ribs have been formed on the inner surface of the vessel body to inwardly project toward the reagent cassette in the aforementioned second embodiment, the number of and the positional relation between the ribs can be properly changed, and at least a part of the inner surface of the vessel body may be inwardly projected.

The thickness of the vessel body is preferably at least 0.05 mm and not more than 0.5 mm in each of the aforementioned embodiments. When structuring the vessel body in this manner, the thicknesses of the portion in which the reagent cassette is stored in the vessel body and the reaction chamber are at least 0.05 mm and not more than 0.5 mm, whereby the sealing means is properly melted by heating in PCR, and PCR is properly performed.

While paraffin has been employed as the sealing means in each of the aforementioned embodiments, the sealing means may be wax, grease, paraffin or wax. Every one of these is sealing means solid at ordinary temperature and entering a liquid state in first heating of PCR, whereby reliability of PCR is improved. Solid includes semisolid or glassy so far as the sealing means is capable of sealing. Further, the liquid state (melted state) may simply be a state where fluidity increases as compared with the solid state to be released from sealing.

While the melting point of the sealing means has been about 50° C. in each of the aforementioned embodiments, the melting point (the temperature at which the sealing means shifts to the aforementioned melted state) is preferably 40° C. to 80° C., and more preferably 45° C. to 60° C. Further, the specific gravity is preferably smaller than that of water. Thus, the function/effect of being solid at ordinary temperature for isolating the reagents or the specimen and melted by first heating in PCR for inducing the reagents or the specimen to the lower reaction chamber can be more reliably attained.

While the reagent storing portion of the reagent cassette has been in a state storing no reagents in each of the aforementioned embodiments, the same may be in a state where reagents are stored and sealed with sealing means at the time of selling, for example. When structuring the reagent cassette in this manner, reagents are previously stored and sealed in the reagent cassette, whereby the same can previously store desired quantities and types of reagents, and reliability and rapidity of PCR can be simply and stably improved.

While the reaction chamber has been in a state storing no substance or storing only the specimen until PCR is started in each of the aforementioned embodiments, the same may be deaerated to enter a decompressed state or a vacuum state by chemical or physical treatment.

The reaction chamber may be brought into a state filled with sealing means. When structuring the reaction chamber in this manner, the reaction chamber enters a state where air is discharged before PCR while the sealing means is so melted that the specimen and the reagents are stored through the reagent cassette at the time of PCR, whereby the specimen and the reagents can be easily guided to the reaction chamber, and reliability of PCR is improved.

While the opening has been formed on the sidewall of the forward end portion in the aforementioned third embodiment, the present invention is applicable also when no opening is formed.

While the reagents have been stored in all reagent storing portions of the reagent cassette in each of the aforementioned embodiments, there may be a reagent storing portion in which no reagent is stored at the time of use.

While the PCR vessel has been made of polypropylene in each of the aforementioned embodiments, the same is preferably made of at least one type of material selected from a group consisting of polyethylene, polystyrene, polyethylene terephthalate, polyethylene naphthalate, polycarbonate, polyamide, acrylic, cyclic polyolefin and aromatic nylon. This is to make the whole PCR vessel including the reagent cassette not deformed or the like by heating in PCR.

While the specific DNA detector is employed in amplification of DNA and detection of the amplified DNA in each of the aforementioned embodiments, another DNA amplifier or an apparatus performing detection of amplified DNA may be employed.

A portion where the specimen or the reagents (both of the specimen and the reagents in a case of collecting the specimen by employing the recess portion of the lid body, or only the reagents in a case of directly storing the specimen in the vessel body without employing the recess portion of the lid body) flow from the reagent cassette into the reaction chamber is now described.

Figure 21:
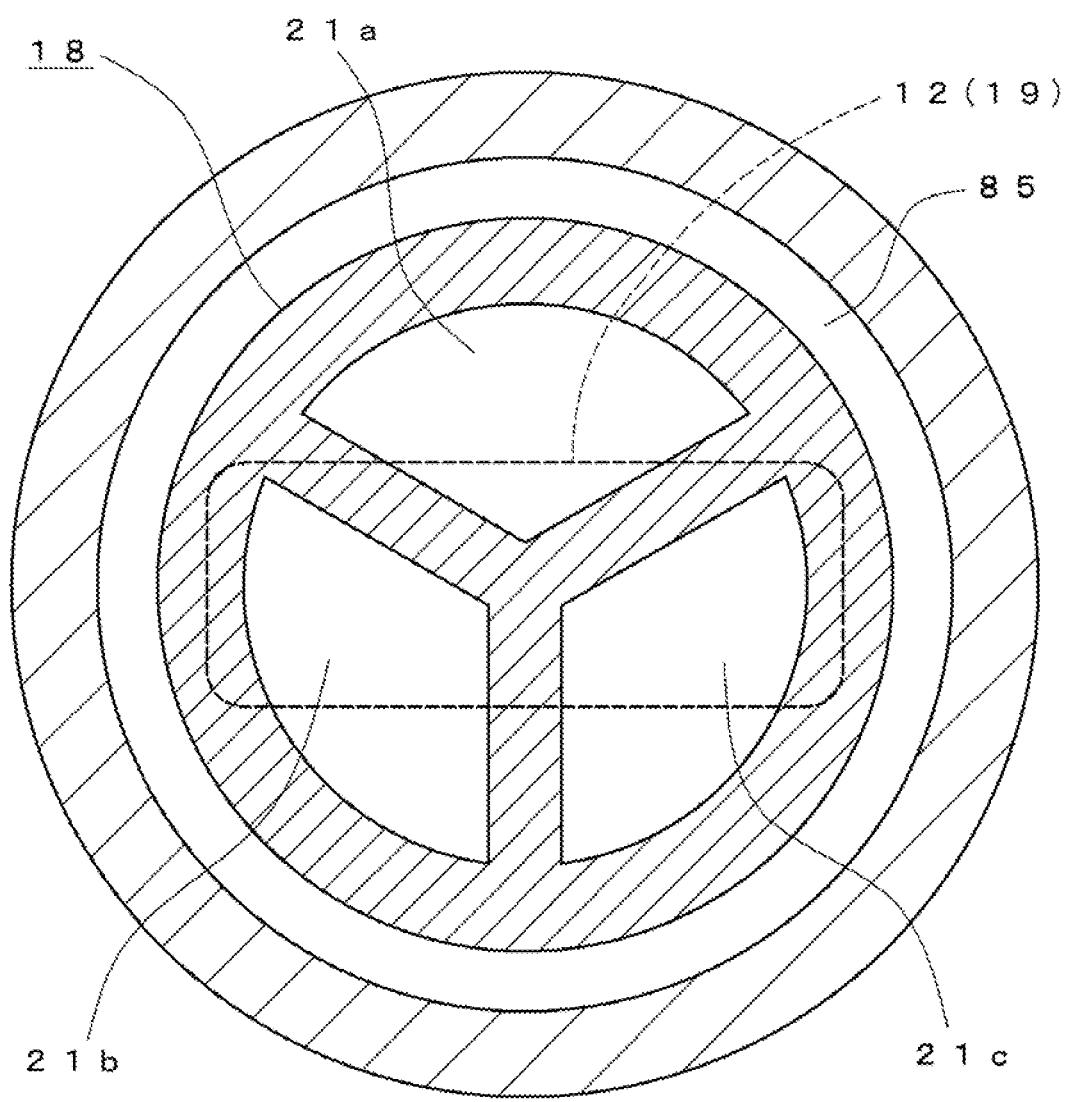
FIG. 21 A schematic sectional view along a line XXI-XXI shown in FIG. 1.

FIG. 21 is a schematic sectional view along a line XXI-XXI shown in FIG. 1.

Referring to the figure, the specimen or the reagents flow into an upper edge 19 of the reaction chamber 12 drawn in broken lines from reagent storing portions 21a to 21c of a reagent cassette 18 (that of a mode provided with no slits 23 in the aforementioned reagent cassette 16 in FIG. 5) in the storage state shown in FIG. 1.

In the PCR vessel according to the aforementioned first embodiment, however, the projection area of the upper edge 19 of the reaction chamber 12 in plan view has been smaller than those of the reagent storing portions 21a to 21c, as shown in FIG. 21. Therefore, the movement route of the specimen or the reagents flowing into the reaction chamber 12 at the time of PCR is in such a state that the arrival point (the upper edge 19 of the reaction chamber 12) is narrow with respect to departure points (the reagent storing portions 21a to 21c), and there has been such apprehension that the specimen or the reagents do not smoothly flow into the reaction chamber.

Since the reagent cassette 18 has a rotationally symmetrical shape in plan view, there is also a case where the specimen or the reagents are stored in a state rotating in the peripheral direction as compared with the state shown in FIG. 21. In such a case, there has been such apprehension that an adequate area of projection in plan view so decreases that the specimen or the reagents similarly do not smoothly flow into the reaction chamber since the upper edge 19 of the reaction chamber 12 is substantially rectangular while the reagent storing portions 21a to 21c form parts of a circular inner portion.

As shown in FIG. 1 and FIG. 21, further, a clearance 85 as a play is present between the reagent cassette 18 (the outer surface thereof) and the vessel body 11 (the inner surface thereof), and there is also a case where the reagent cassette 18 is stored in a position slightly deviating in plan view as compared with the central position shown in FIG. 21. Also in such a case, there has been such apprehension that the specimen or the reagents similarly do not smoothly flow into the reaction chamber.

In addition, there has been such apprehension that the specimen or the reagents are induced to the aforementioned clearance 85 due to surface tension at the time of PCR and the quantity flowing into the reaction chamber decreases.

As hereinabove described, there is apprehension for such a situation that the specimen or the reagents do not smoothly flow from the reagent storing portions 21a to 21c of the reagent cassette 18 into the reaction chamber 12 at the time of PCR in the aforementioned PCR vessel, and there has been still room for betterment in points of improvement in stability of PCR as well as improvement in PCR efficiency.

Figure 22:
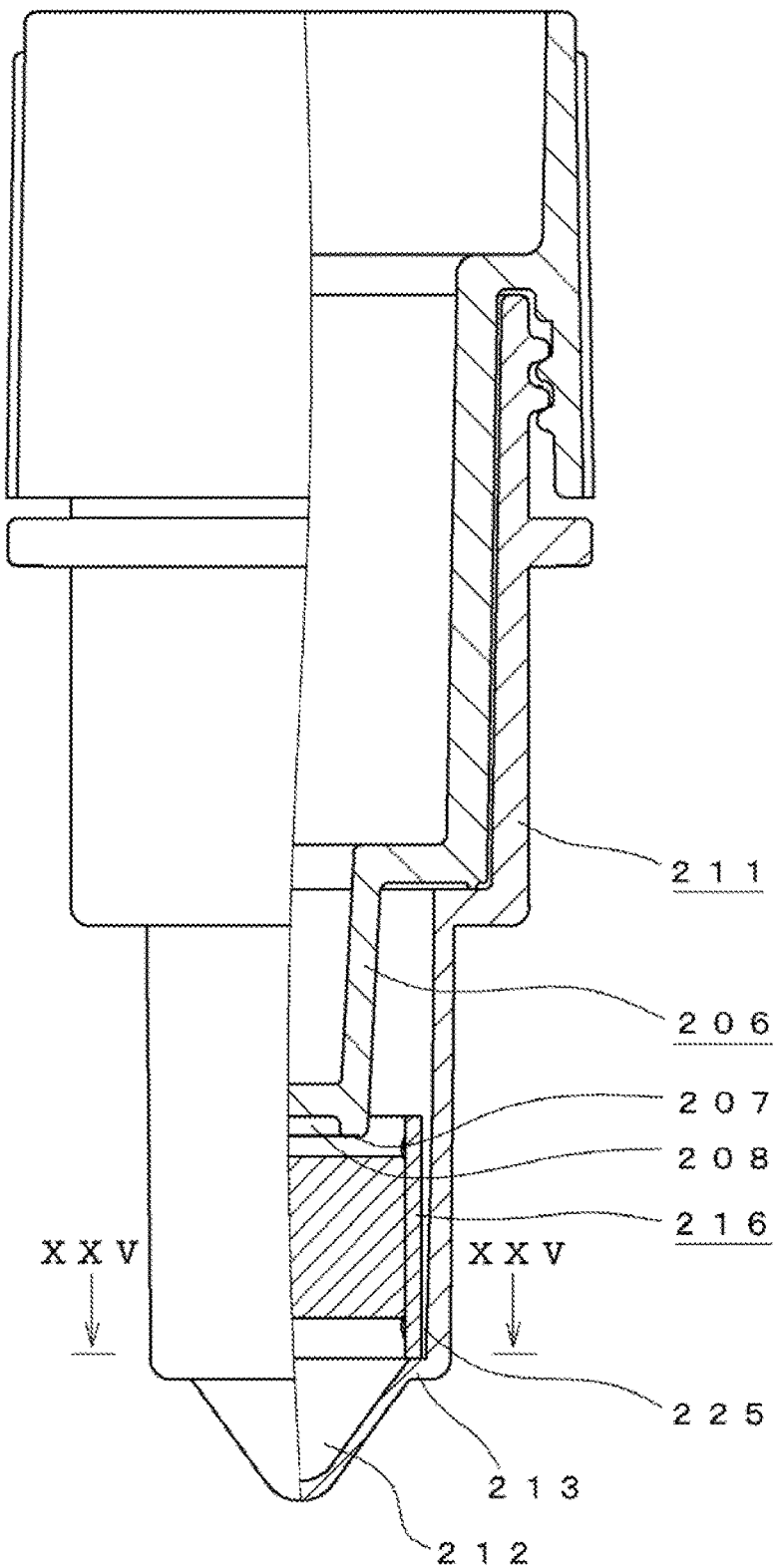
FIG. 22 A front elevational view and a partially fragmented sectional view showing the appearance and a central sectional structure of a PCR vessel according to a fourth embodiment of the present invention.

Those proposed in order to solve such problems are thirty-first to forty-second aspects of the present invention, and embodiments related to these are as follows:

FIG. 22 illustrates a front elevational view and a partially fragmented sectional view showing the appearance and a central sectional structure of a PCR vessel according to a fourth embodiment of the present invention.

The basic structure of a PCR vessel 201 according to the fourth embodiment of the present invention is similar to that of the aforementioned PCR vessel according to the first embodiment, and hence the same is described mainly with reference to different points.

Referring to the figure, the PCR vessel 201 is mainly constituted of a vessel body 211, a lid body 206 fittable with the vessel body 211 and a reagent cassette 216 stored in the vessel body 211. The vessel body 211 has a reaction chamber 212 storing and reacting a specimen and reagents at the time of PCR on a bottom portion 213 thereof. In the lid body 206, an upwardly concave recess portion 208 capable of storing at least a part of the specimen through contact with the specimen (not shown) is formed on a lower surface 207 thereof. The reagent cassette 216 is stored in a portion between the lid body 206 and the reaction chamber 212 in the vessel body 211.

At the time of use of the PCR vessel 201, it follows that the reaction chamber 212 is positioned on the lowermost portion for storing and reacting the specimen and the reagents in the vertical direction shown in FIG. 22. In this specification, an upper direction indicates a direction where the reagent cassette and the lid body are positioned with respect to the reaction chamber at the time of use of the PCR vessel, while a lower direction reversely indicates a direction where the reaction chamber is positioned with respect to the reagent cassette and the lid body at the time of use of the PCR vessel.

The reagents are reagents necessary for PCR, desired types may be selected in response to the use, and water, a buffer solution, a primer, dNTP, a magnesium compound, DNA polymerase, a fluorescent reagent and the like can be listed, for example. While the fluorescent reagent is not necessary for PCR itself, embodiments of the present invention are described in states including the fluorescent reagent for the purpose of simultaneously performing photodetection in a DNA detector after completion of PCR.

Further, the specimen indicates a specimen containing target DNA.

Figure 24:
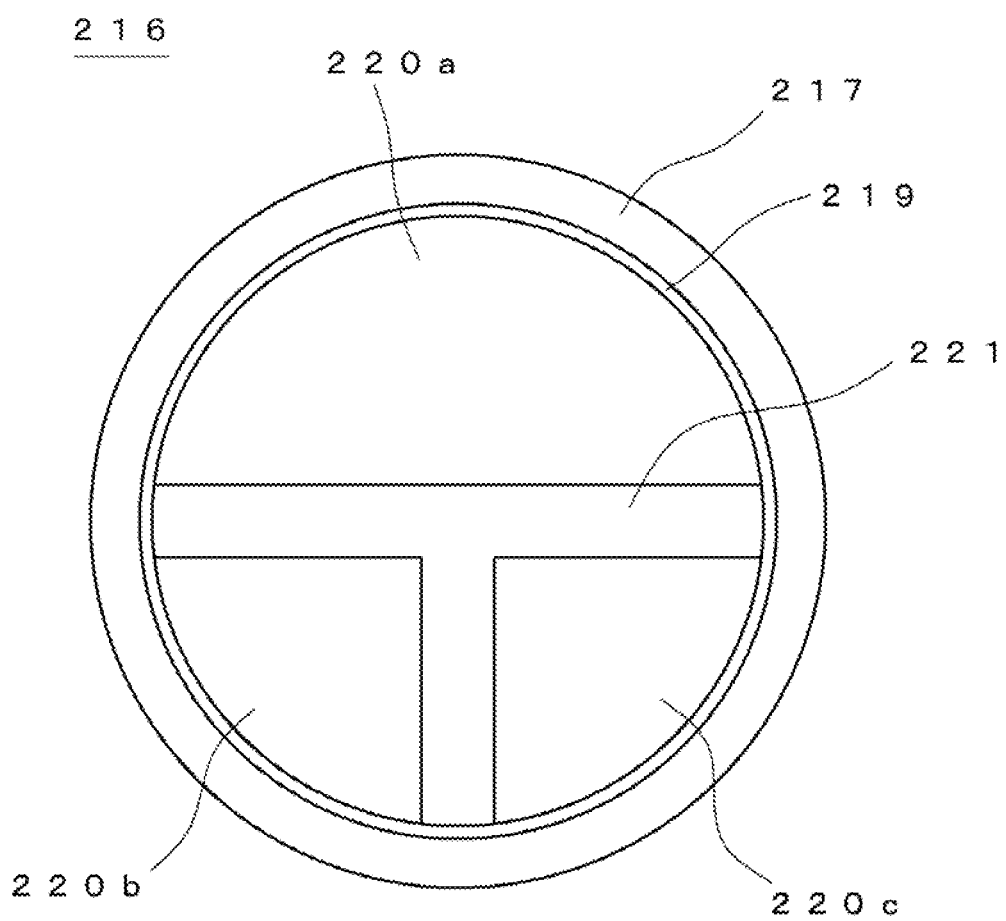
FIG. 24 A plan view showing the structure of the reagent cassette of the PCR vessel shown in FIG. 22.

FIG. 23 illustrates a front elevational view and a partially fragmented sectional view showing a central sectional structure of the reagent cassette of the PCR vessel shown in FIG. 22, with (1) in a state before storing reagents, and (2) in a state after storing and sealing the reagents, and FIG. 24 illustrates a plan view showing the structure of the reagent cassette of the PCR vessel shown in FIG. 22.

Referring to these figures, the reagent cassette 216 includes a sidewall 217 as a basic framework of a cylindrical shape opened in the vertical direction.

A plurality of reagent storing portions 220a to 220c separated from each other by a partition wall 221 of a T shape in plan view extending in the vertical direction and capable of storing reagents in the respective ones thereof are formed in the sidewall 217.

A step portion 223a is formed on an upper edge 222 of the partition wall 221, to be positioned downward beyond an upper edge 218 of the sidewall 217. A step portion 223b is similarly formed also on a lower side of the reagent cassette 216, so that the reagent cassette 216 is usable with no problem also when the same is stored in a vertically inverted state.

When using the reagent cassette 216 shown at (1) in FIG. 23, paraffin is laid on a lower surface of the reagent cassette 216 by first pressing the lower surface against the paraffin in a melted state and thereafter cooling the same, desired types and quantities of reagents are stored in the respective ones of the reagent storing portions 220a to 220c with an automatic dispenser, and an upper surface of the reagent cassette 216 is also filled with paraffin for sealing the reagents. Thus, the upper and lower step portions 223a and 223b of the reagent cassette 216 are filled with paraffin members 224a and 224b as sealing means solid before PCR and melted by heating in PCR, to enter states sealing the reagents in the reagent storing portions 220a to 220c. The paraffin members 224*a* and 224*b* may cover portions (upper and lower edges of the sidewall 217, for example) outward beyond the step portions 223*a* and 223*b*.

Returning and referring also to FIG. 22, the lower surface 207 of the lid body 206 is arranged between the upper edge 222 of the partition wall 221 and the upper edge 218 of the sidewall 217 in a state where the lid body 206 and the reagent cassette 216 are mounted on the vessel body 211. In other words, it follows that the lower surface 207 of the lid body 206 enters the step portion 223*a* of the reagent cassette 216 (the paraffin member 224*a* filling the same after sealing).

While there has been such apprehension that the specimen or the reagents leak out of the reagent cassette 18 at the time of PCR in the aforementioned PCR vessel according to the first embodiment since the lower surface 7 of the lid body 6 and the reagent cassette 18 (the upper end surface thereof) have been set in the dimensional relation substantially in contact with each other, the PCR vessel 201 according to the fourth embodiment includes such a structure (regulation means) that the lower surface 207 of the lid body 206 enters the step portion 223 of the reagent cassette 216 as described above, whereby the reagents or the specimen from the recess portion 208 on the lower surface 207 of the lid body 206 can be induced to smoothly flow into the reagent cassette 216 (i.e., can be regulated not to leak out of the reaction chamber 212 shown in FIG. 22), and stability of PCR is improved.

Inwardly projecting ribs 219 are formed on the whole periphery of the bottom (an upper side adjacent portion of a connecting portion between the upper end surface 222 of the partition wall 221 and the sidewall 217) of the step portion 223. These ribs 219 serve as dislocation preventers for sealing means such as paraffin, and prevent sealing of the reagents from unprepared releasing. The ribs 219 are present on an upper side and a lower side.

Another regulation means possessed by the PCR vessel 201 is now described.

Figure 25:
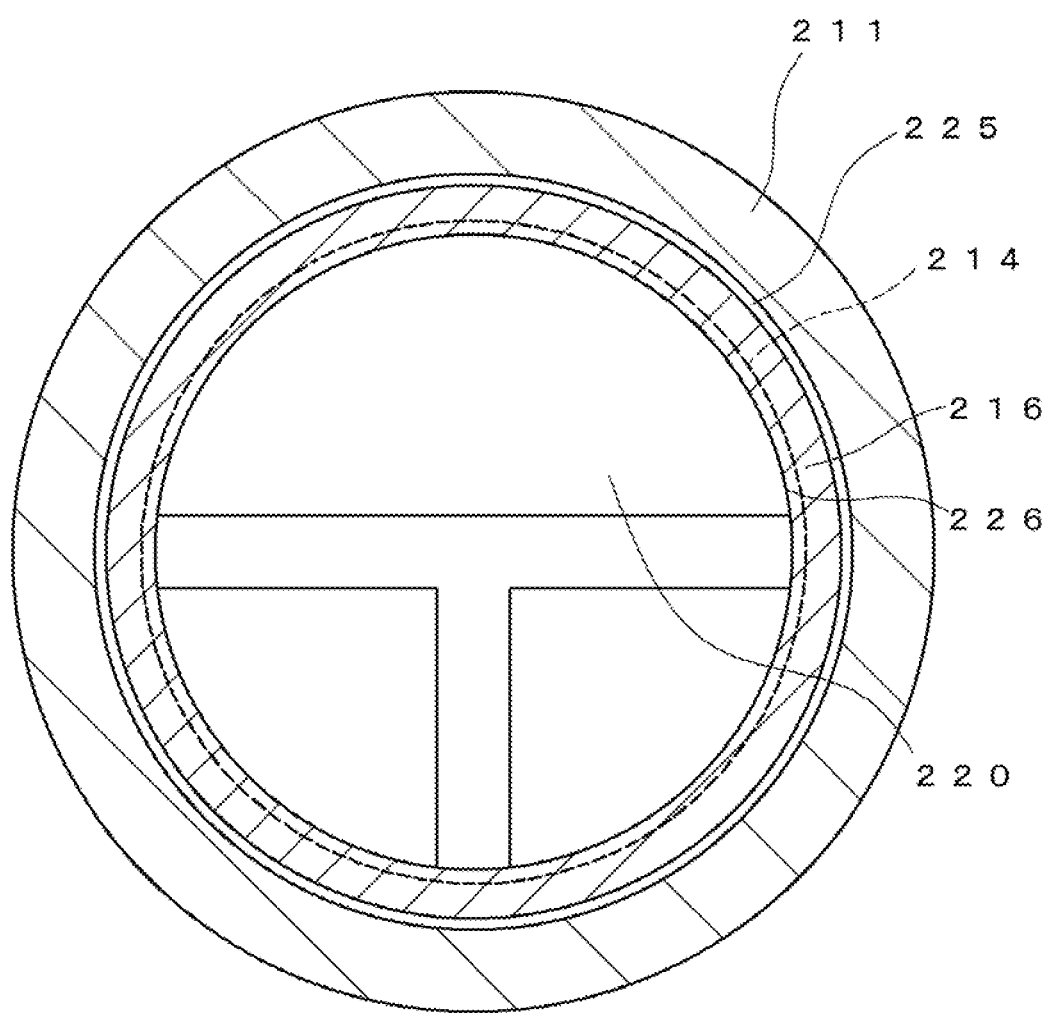
FIG. 25 A sectional view along a line XXV-XXV shown in FIG. 22.

FIG. 25 is a sectional view along a line XXV-XXV shown in FIG. 22.

Referring to FIG. 22 as well as FIG. 25, an upper edge 214 of the reaction chamber 212 drawn in broken lines is configured to be circular in plan view. The reaction chamber 212 is so structured in this manner that the relative projection position of the upper edge 214 of the reaction chamber 212 with respect to the reagent storing portions 220*a* to 220*c* of the reagent cassette 216 remains unchanged also in a case where the reagent cassette 216 is stored in the vessel body 211 in a state rotating in the peripheral direction, whereby the specimen or the reagents so stably flow into the reaction chamber 212 at the time of PCR that stability of PCR is improved.

As shown in FIG. 22, the reaction chamber 212 has a downwardly tapered conical shape. Effects of structuring the reaction chamber 212 in this manner are described later.

A clearance 225 between the vessel body 211 (the inner surface thereof) and the reagent cassette 216 (the outer surface thereof) is set to be narrow as compared with the clearance 85 in the PCR vessel according to the first embodiment. That is, the upper edge 214 of the reaction chamber 212 is set to be positioned outward beyond the maximum movable region of an outer edge 226 of the lower end of the reagent storing portion 220 at the time of storage. In other words, the upper edge 214 of the reaction chamber 212 drawn in the broken line shown in FIG. 25 is regularly positioned outward beyond the outer edge 226 of the lower end of the reagent storing portion 220 also in a case where the reagent cassette 216 moves to an end of one side in the lateral direction (a direction where the reagent cassette 216 is movable also in the state stored in the vessel body 211) and in a case where the same moves to an end on another side.

The reaction chamber 212 is so structured in this manner that the specimen or the reagents stably flow into the reaction chamber 212 also in a state where the reagent cassette 216 is stored while deviating in the lateral direction, whereby stability of PCR is improved.

A process of progressing PCR with a DNA detector while employing the PCR vessel 201 storing the specimen and the reagents is now described.

Figure 26:
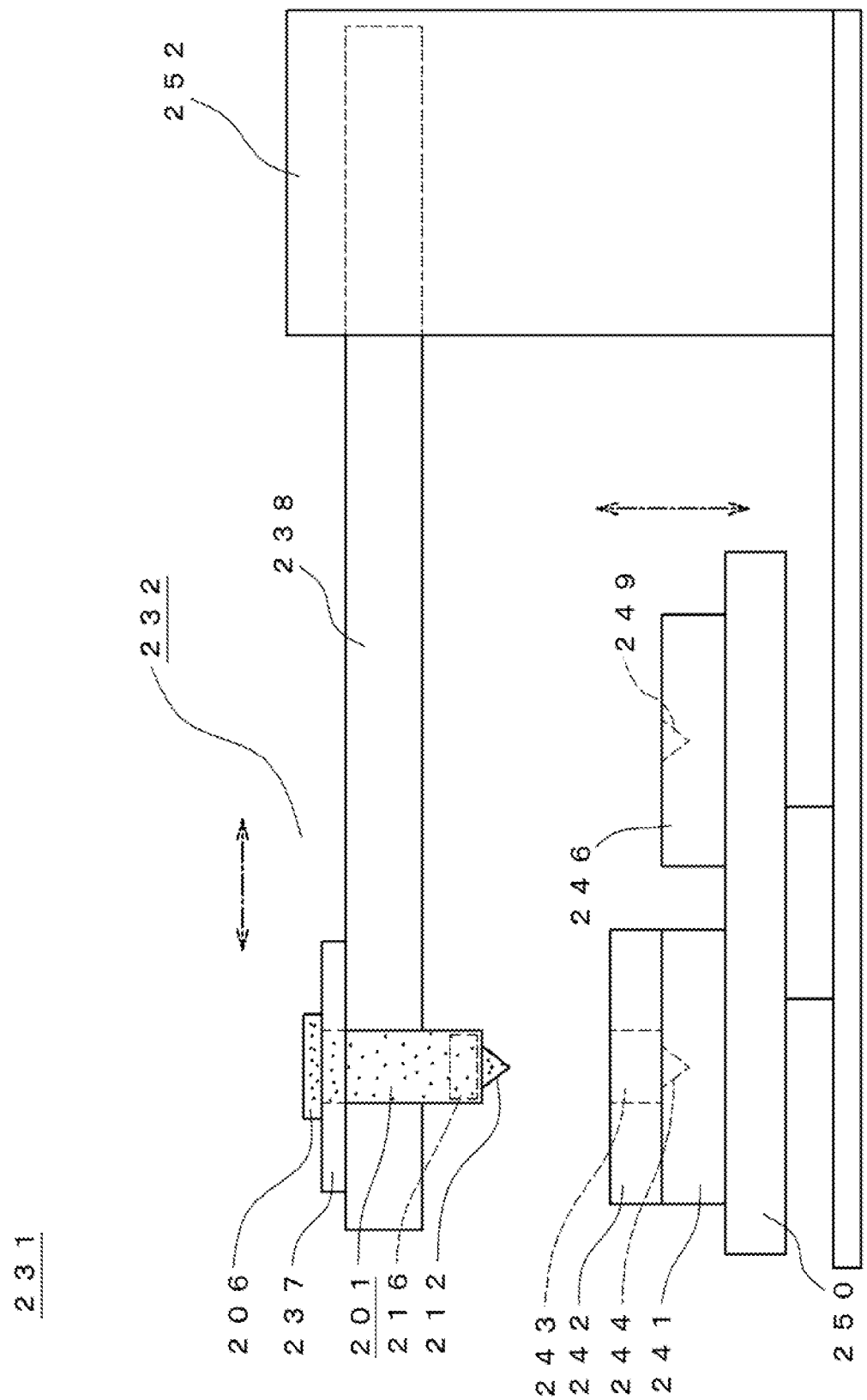
FIG. 26 A schematic front elevational view showing a state before operation of a DNA detector employing the PCR vessel shown in FIG. 22.

FIG. 26 is a schematic front elevational view showing a state before operation of a DNA detector employing the PCR vessel shown in FIG. 22.

Referring to the figure, a DNA detector 231 is mainly constituted of a DNA amplifying structure 232 progressing PCR by performing heating and cooling, a detecting portion 252 measuring PCR products stored in the PCR vessel completing PCR by photodetection and a control portion (not shown).

The DNA amplifying structure 232 is mainly constituted of a vessel holder 237 holding the PCR vessel 201, a support portion 238 supporting the vessel holder 237, a plate-type first heater 241 on a high-temperature side, a ring plate-shaped heating plate 242 fixed to an upper portion of the first heater 241, a plate-shaped second heater 246 on a low-temperature side and a seat 250 fixing the first heater 241 and the second heater 246 to an upper surface thereof.

The PCR vessel 201 stores the reagent cassette 216 storing the reagents as described above, and tightly is closed with the lid body 206 in a state storing the specimen by the recess portion 208 of the lid body 206 or by a manual operation.

The vessel holder 237 holds the PCR vessel 201 so that the bottom surface of the PCR vessel 201 (the reaction chamber 212) is flush with the surfaces of the first heater 241 and the second heater 246.

The support portion 238 is configured to support the vessel holder 237. Following an instruction from the control portion, the support portion 238 can slide the vessel holder 237 in the horizontal direction (the direction from the first heater 241 to the second heater 246 or the inverse direction thereof, i.e., the direction from these to the detecting portion 252 or the inverse direction thereof) as shown by arrow drawn in a one-dot chain line on an upper portion of the figure, whereby the PCR vessel 201 can be freely moved to a portion above the first heater 241, a portion above the second heater 246 or the detecting portion 252.

The first heater 241 is formed by a heating body covered with silicone rubber, for example, so structured that the temperature thereof is adjustable by the control portion, and has a recess 244 into which the reaction chamber 212 of the PCR vessel 201 is fittable on an upper surface thereof. The surface of the recess 244 is set to a high temperature of 120° C., for example, by the control portion.

The heating plate 242 is made of aluminum having high heat conductivity, for example, and has a through-hole 243 into which the PCR vessel 201 is insertable on a central portion thereof. The thickness of the heating plate 242 is substantially identical to the vertical height of the reagent cassette 216. The inner surface of the through-hole 243 is warmed up by heat conduction from the first heater 241 to reach 80° C., for example.

The second heater 246 is similar to the aforementioned first heater 241 except for the temperature, formed by a heating body covered with silicone rubber, for example, so structured that the temperature thereof is adjustable by the control portion, and has a recess 249 into which the reaction chamber 212 of the PCR vessel 201 is fittable on an upper surface thereof. The surface of the recess 249 is set to a low temperature of 50° C., for example, by the control portion.

The first heater 241 and the second heater 246 are fixed to the upper surface of the seat 250. The seat 250 is controlled by the control portion to be slidable in the vertical direction (a direction from the reaction chamber 212 toward the recess 244 in the state of FIG. 26 or the inverse direction thereof) as shown by arrow drawn in a one-dot chain line on a lower portion of the figure. Thus, the first heater 241 and the second heater 246 are ascendable or descendable.

Figure 27:
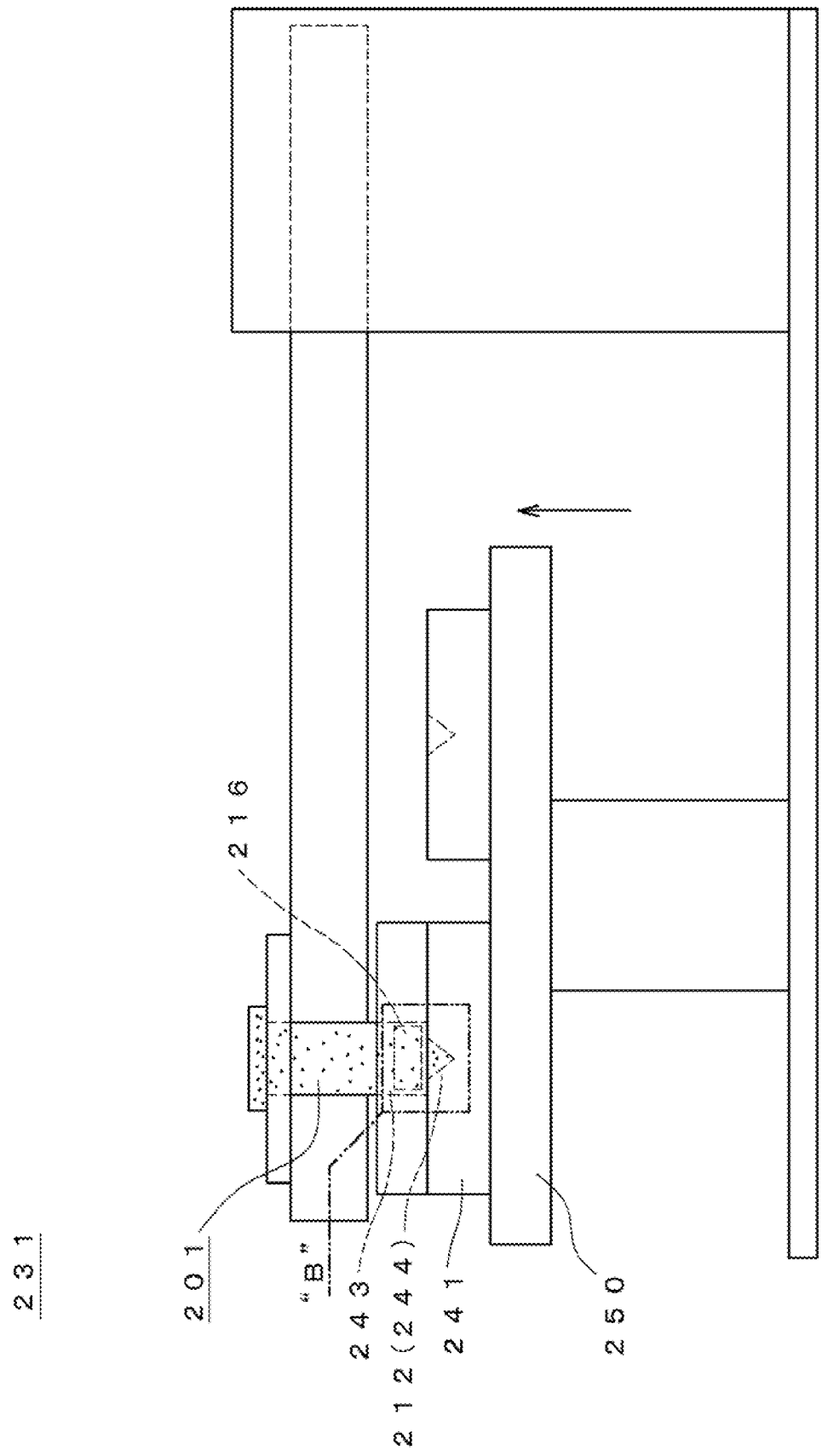
FIG. 27 A schematic front elevational view, corresponding to FIG. 26, showing an operating state of the DNA detector.

FIG. 27 is a schematic front elevational view, corresponding to FIG. 26, showing an operating state of the DNA detector.

Referring to the figure, the seat 250 first ascends from the state before operation shown in FIG. 26 in a direction of arrow drawn in a solid line in the figure following an instruction from the control portion, whereby the PCR vessel 201 passes through the through-hole 243 of the heating plate 242, while the reaction chamber 212 of the PCR vessel 201 fits into the recess 244 of the first heater 241.

Then, a portion of the PCR vessel 201 in which the reagent cassette 216 is stored is warmed up through the through-hole 243 by heating in PCR, to melt paraffin on the upper and lower step portions of the reagent cassette 216, and to discharge the reagents or the specimen therein to the lower reaction chamber 212 (also refer to FIG. 28 described later). Further, the specimen and the reagents stored in the reaction chamber 212 of the PCR vessel 201 are heated through contact (first contact) between the surface of the reaction chamber 212 of the PCR vessel 201 and the surface of the recess 244 of the first heater 241.

The influx of the specimen and the reagents into the reaction chamber is now described.

Figure 28:
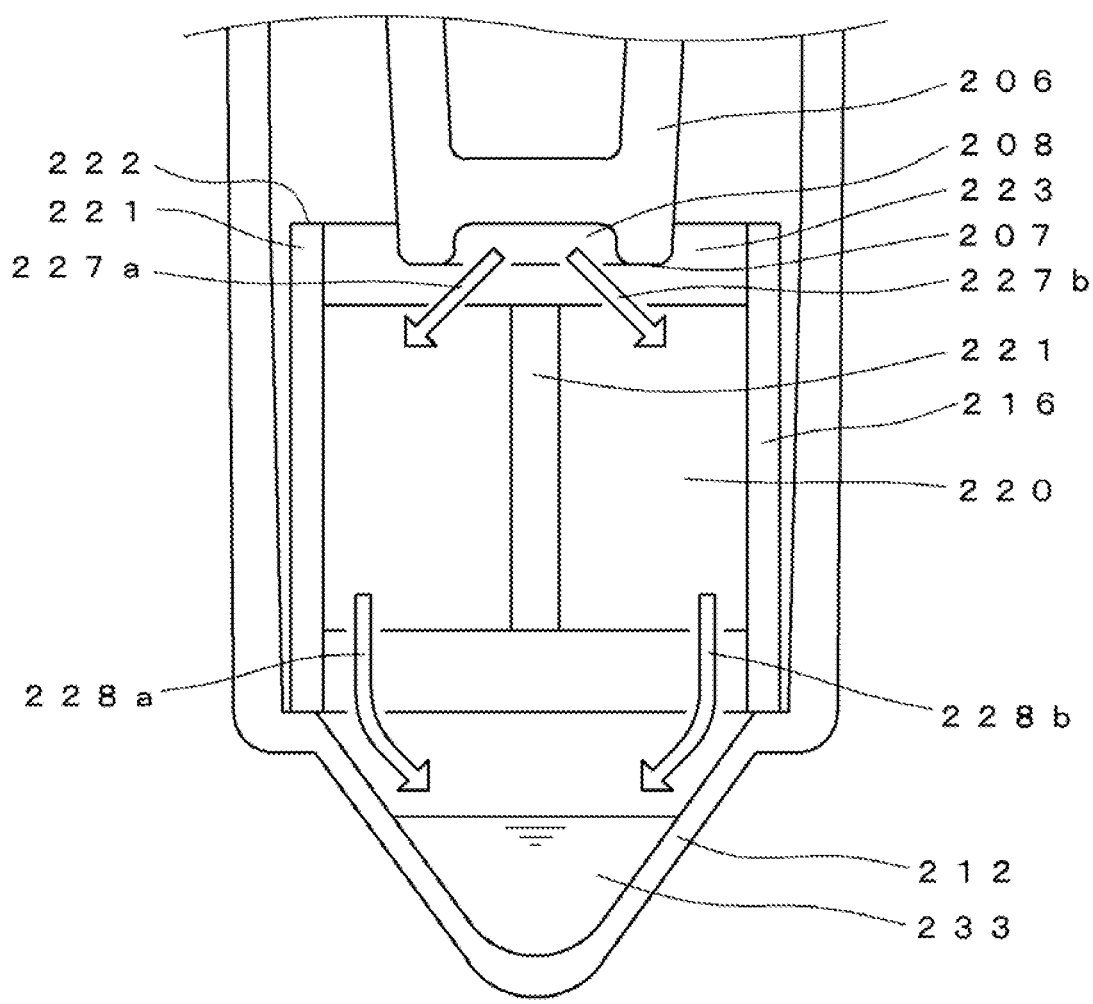
FIG. 28 A typical drawing showing the internal structure of the PCR vessel in a portion B shown in FIG. 27.

FIG. 28 is a typical drawing showing the internal structure of the PCR vessel in a portion B shown in FIG. 27.

Referring to the figure, unshown upper and lower paraffin members are first melted by first heating in PCR, so that the reagent cassette 216 enters a state penetrating in the vertical direction as described above. The lower surface 207 of the lid body 206 is configured to enter the step portion 223 of the reagent cassette 216 at this time as described above, whereby the specimen having been stored in the recess portion 208 of the lid body 206 is regulated not to go round toward the upper edge 218 of the sidewall 217 of the reagent cassette 216 and leak out of the reaction chamber 212. Therefore, the specimen stably moves to the reagent storing portion 220 while avoiding the partition wall 221, as shown by arrows 227*a* and 227*b*.

Then, the specimen and the reagents having been stored in the reagent storing portion 220 are mixed with each other, to move to the lower reaction chamber 212 as shown by arrows 228*a* and 228*b* and to form a PCR solution 233 corresponding to the specimen and the reagents necessary for PCR.

Returning and referring also to FIG. 27, the reaction chamber 212 of the PCR vessel 201 fits into the recess 244 of the first heater 241, and the PCR solution 233 stored in the reaction chamber 212 is heated.

The reaction chamber 212 has the downwardly tapered conical shape as described above so that the forward end is sharpened as compared with a reaction chamber 212 having a semispherical shape or a cylindrical shape, whereby adhesiveness to the first heater 241 heating the PCR vessel 201 and the second heater 246 shown in FIG. 26 increases. In other words, portions of these heaters in contact with the PCR vessel 201 are made of silicone rubber, whereby high adhesiveness to the surface of the reaction chamber 212 which is tapered (in other words, gradually widened upward) since silicone rubber is excellent in elasticity (shape recoverability from compressive deformation).

The portion of the reaction chamber 212 is advantageous in strength against force from the lower direction or the lateral direction due to the shape thereof so that the thickness thereof can be easily reduced in production, whereby heating efficiency from the heaters so increases that the heating time can be shortened. According to this embodiment, the average thickness of the reaction chamber 212 is 0.3 mm, and the reaction chamber 212 is configured to be thinner than the thickness of 0.5 mm in other portions of the vessel body 211. This is thinner than the thickness of 0.5 mm of the reaction chamber of the PCR vessel according to the first embodiment.

As described above, the reaction chamber 212 is so provided in the downwardly tapered conical shape as to improve efficiency in PCR in the PCR vessel 201 according to this embodiment.

When heating through first contact for a prescribed time is completed, the seat 250 descends following an instruction from the control portion, and is released from the first contact to return to the state shown in FIG. 26. While illustration is hereinafter omitted, the support portion 238 thereafter horizontally moves the vessel holder 237 following an instruction from the control portion so that the PCR vessel 201 comes to a portion above the second heater 246, and the seat 250 so ascends that the reaction chamber 212 of the PCR vessel 201 fits into the recess 249 of the second heater 246 to result in contact (second contact) between the surface of the reaction chamber 212 of the PCR vessel 201 and the surface of the recess 249 of the second heater 246, similarly to the case of the first contact described above with reference to FIG. 27. The PCR solution 233 is cooled to 65° C., for example, due to this second contact, and annealing is performed.

When cooling through the second contact for a prescribed time is completed, the seat 250 descends following an instruction from the control portion, the vessel holder 237 is horizontally moved by the support portion 238, and the PCR vessel 201 returns to the state shown in FIG. 26 positioned above the first heater 241.

The first contact and the second contact are thus alternately repeated, whereby PCR progresses. When the first contact and the second contact are repeated by a prescribed number of times to complete PCR, the process advances to a step of detecting amplified DNA.

Figure 29:
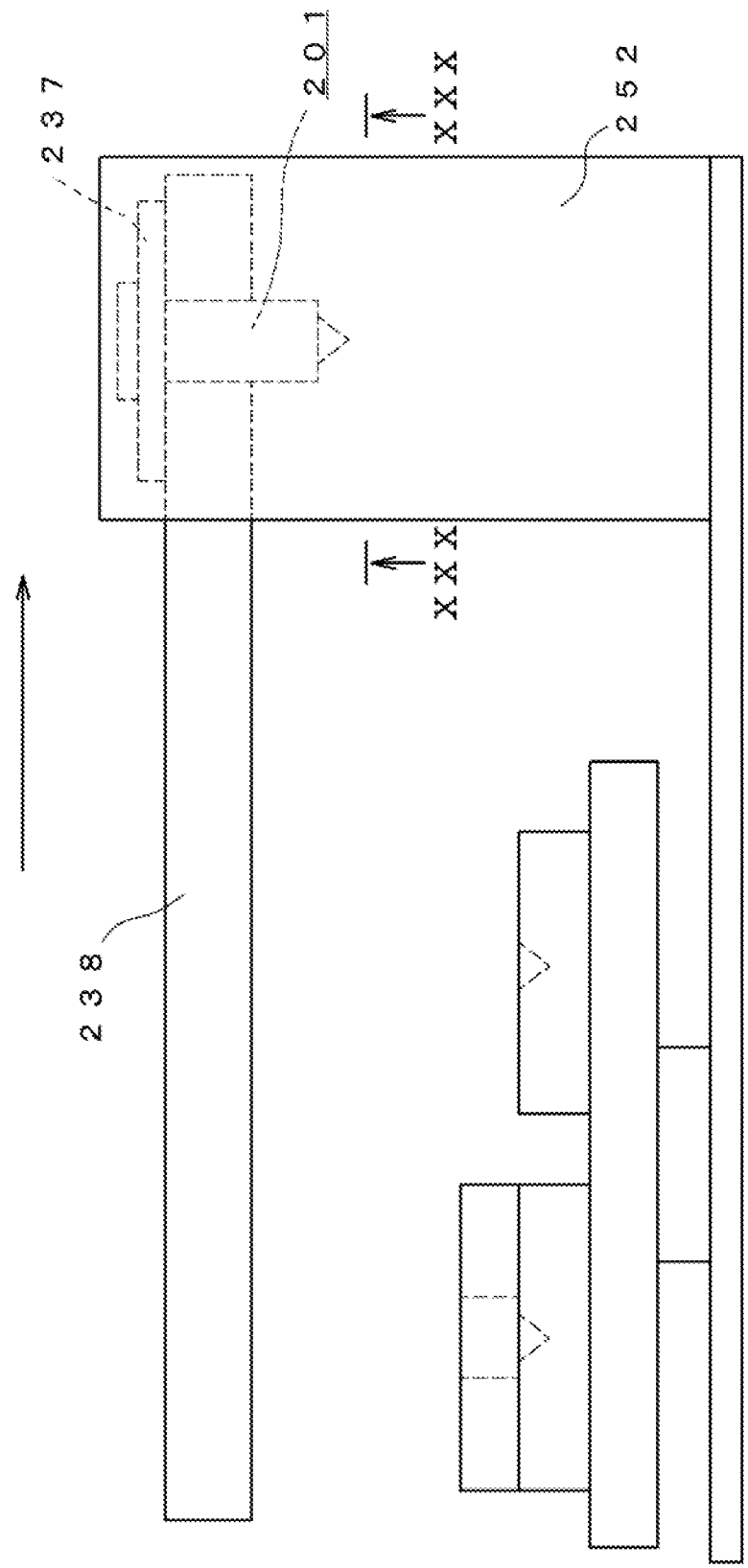
FIG. 29 A schematic front elevational view, corresponding to FIG. 26, showing a state where PCR is completed and the PCR vessel moves to a detecting portion.

FIG. 29 is a schematic front elevational view, corresponding to FIG. 26, showing a state where PCR is completed and the PCR vessel moves to the detecting portion.

Referring to the figure, the support portion 238 moves the vessel holder 237 in a direction shown by arrow in the figure following an instruction from the control portion after PCR is completed, whereby the PCR vessel 201 moves to the detecting portion 252.

Figure 30:
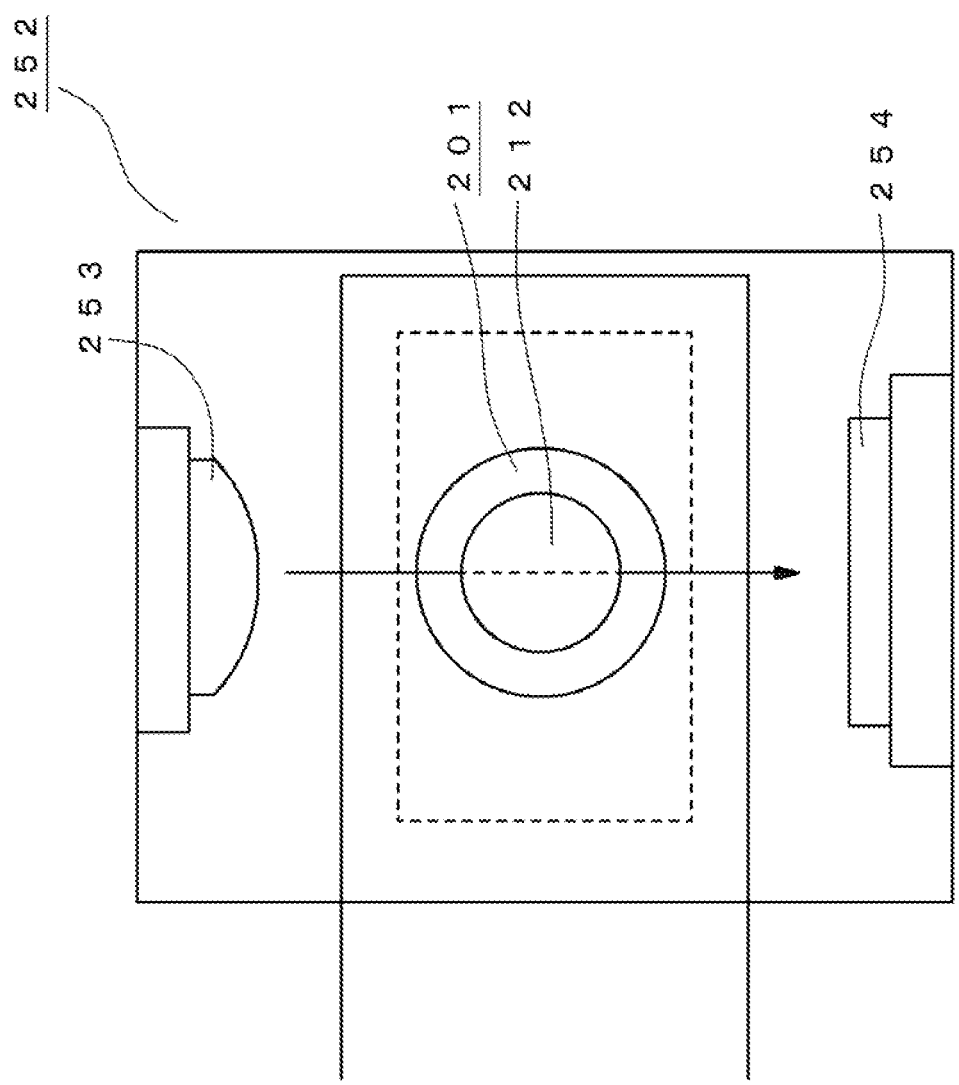
FIG. 30 A drawing seen along a line XXX-XXX shown in FIG. 29.

FIG. 30 is a drawing seen along a line XXX-XXX shown in FIG. 29.

Referring to the figure, the detecting portion 252 is mainly constituted of a light emitter 253 and a photodetector 254. The light emitter 253 and the photodetector 254 are arranged to face each other in the horizontal direction on a coaxial straight line. The PCR vessel 201 is so positioned that the straight line passes through the reaction chamber 212 in which amplified DNA is stored. The light emitter 253 is an LED lamp whose effective wavelength is 450 nm to 570 nm. The photodetector 254 is a photodiode whose effective wavelength is 300 nm to 820 nm.

In detection, the light emitter 253 emits excitation light toward the reaction chamber 212 of the PCR vessel 201 following an instruction from the control portion. The amplified DNA in the reaction chamber 212 is bonded to a fluorescent reagent included in the reagents, and reacts to the excitation light to fluoresce. The reaction chamber 212 transmits light since the same is made of a transparent material, and the photodetector 254 can receive light emission intensity of the fluorescing DNA. Thus, photodetection of the DNA is possible without transferring PCR products from the PCR vessel to another detection vessel. Then, quantitative measurement of the amplified DNA can be performed on the basis of the received light emission intensity.

As described above, at least one of the vessel body 211, the lid body 206 and the reagent cassette 216 includes regulation means regulating the specimen or the reagents not to leak out of the reaction chamber 212 at the time of PCR in the PCR vessel 201 according to the present invention.

The PCR vessel is so structured in this manner that the specimen or the reagents are induced by the regulation means to stably flow from the reagent storing portions 220a to 220c of the reagent cassette 216 into the reaction chamber 212 at the time of PCR, whereby stability of PCR is improved, and PCR efficiency is also improved.

Figure 32:
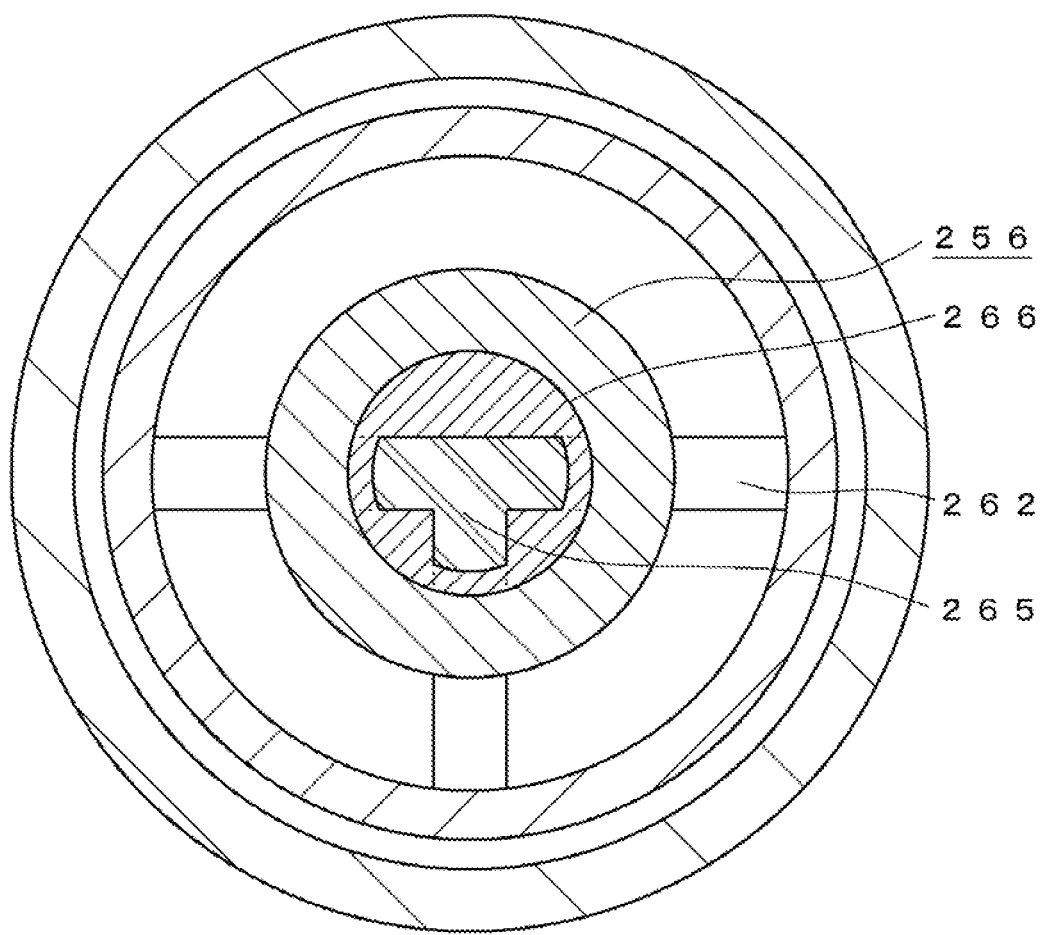
FIG. 32 A sectional view along a line XXXII-XXXII shown in FIG. 31.

FIG. 31 illustrates sectional views showing a central sectional structure around an upper portion of a reagent cassette and a lower portion of a lid body in a PCR vessel according to a fifth embodiment of the present invention, with (1) in a state before the lid body is mounted, and (2) in a state where the lid body is mounted, and FIG. 32 is a sectional view along a line XXXII-XXXII shown in FIG. 31.

A PCR vessel 255 according to the fifth embodiment has a structure basically similar to that of the aforementioned PCR vessel 201 according to the fourth embodiment, and hence the same is described mainly with reference to different points.

First referring to (1) in FIG. 31, a lid body 256 is in such a state that a specimen 264 is stored in a recess portion 258 thereof. The lid body 256 is so mounted on a vessel body 251 as shown by arrow 269, as to enter the state mounted on the vessel body shown at (2) in FIG. 31.

An upper edge 263 of a partition wall 262 of a reagent cassette 259 of the PCR vessel 255 further includes an upwardly convex projecting portion 265 on a portion inward beyond a lower edge (a lower peripheral edge) 266 (266a, 266b) of the recess portion 258 of the lid body 256 in plan view projection indirectly shown in FIG. 32.

An upper edge 267 of the projecting portion 265 is arranged on a vertical height position (a range shown by arrow 270) between a lower surface 257 of the lid body 256 and an upper edge 261 of a partition wall 260 as a basic framework, to be downward beyond an upper edge 268 of the recess portion 258.

Therefore, the projecting portion 265 enters the recess portion 258 of the lid body 256 without forming an obstacle at a time of performing sealing with unshown paraffin or the like, whereby the specimen 264 stored in the recess portion 258 of the lid body 256 is pushed out by the projecting portion 265, and discharged out of the recess portion 258 (into the reagent cassette 259) as shown by arrows 274a and 274b. Thus, the specimen 264 is prevented from remaining in the recess portion 258.

FIG. 33 illustrates sectional views, corresponding to FIG. 31, showing the structures of reagent cassettes of PCR vessels according to further embodiments of the present invention.

The PCR vessels according to these embodiments have structures basically similar to that of the aforementioned PCR vessel 255 according to the fifth embodiment, and hence the same are described mainly with reference to different points.

First referring to (1) of the figure, a projecting portion 301 of a reagent cassette 300 is so provided as to have a triangular shape in sectional view with an upper edge 302 serving as an apex above the whole of an upper edge 308 of a partition wall 307. Such a structure is also included in the present invention as a mode upwardly convex in a portion inward beyond lower edges 306a and 306b of a recess portion 305 of a lid body 303.

Then, referring to (2) of the figure, a projecting portion 311 of a reagent cassette 310 is so arranged that an upper edge 312 thereof is in contact with a part of an upper edge 316 of a recess portion 315 of a lid body 313. Such a structure is also included in the present invention as such a mode that the upper edge 312 of the projecting portion 311 is arranged downward beyond the upper edge 316 of the recess portion 315.

While the regulation means have been provided in all of the vessel body, the lid body and the reagent cassette in the aforementioned fourth of fifth embodiment, the regulation means (the structure rendering the upper edge of the reaction chamber circular, or the structure of the dimensional relation of the upper edge of the reaction chamber or the clearance) may be mainly provided on the vessel body, the regulation means (the structure thinning and lengthening the forward end of the lid body) may be mainly provided on the lid body, or the regulation means (the structure providing the step portions on the reagent cassette) may be mainly provided on the reagent cassette.

While the reagent cassette has had the cylindrical shape in the aforementioned fourth or fifth embodiment, the same may have another tubular shape. For example, the reagent cassette may have a tubular shape with a polygonal ring-shaped section. However, the reagent cassette preferably has a rotationally symmetrical shape in plan view, in consideration of the degree of freedom in storage.

While the PCR vessel as well as the vessel body, the lid body and the reagent cassette constituting the same have had specific shapes in the aforementioned fourth or fifth embodiment, the same may have other shapes. For example, the volumes thereof may be varied in response to the use.

While the reagent cassette has had the plurality of reagent storing portions and the plurality of reagent storing portions have been separated from each other by the partition wall in the aforementioned fourth or fifth embodiment, the reagent cassette may simply have at least one reagent storing portion.

While no slit extending in the vertical direction and communicating with the reagent storing portion has been formed on the sidewall of the reagent cassette in the aforementioned fourth or fifth embodiment, a slit may be formed.

While the upper edge of the reaction chamber has been circular in plan view and set to be positioned outward beyond the maximum movable region of the outer edge of the lower end of the reagent storing portion at the time of storage in the aforementioned fourth or fifth embodiment, the same may have a structure including only one regulation means. In other words, also in a case where the upper edge of the reaction chamber is set to be narrower than the outer edge of the lower end of the reagent storing portion, compatibility to a case of being stored in a state rotating in the peripheral direction of the reagent cassette is improved so far as the same is circular in plan view. Even if the upper edge of the reaction chamber is not circular in plan view, further, the upper edge may have another shape in plan view so far as the same is set to be positioned outward beyond the maximum movable region of the outer edge of the lower end of the reagent storing portion at the time of storage.

While the reaction chamber has had the downwardly tapered conical shape in the aforementioned fourth or fifth embodiment, the same may have another shape such as a downwardly convex semispherical shape, for example.

While the reaction chamber has been made of a transparent material in the aforementioned fourth or fifth embodiment, the present invention can be applied without influencing PCR itself even if the reaction chamber is not made of a transparent material.

While the rib has been formed on the whole periphery of the bottom of the step portion of the reagent cassette in the aforementioned fourth or fifth embodiment, the rib may not be formed.

The thickness of the reaction chamber of the vessel body is preferably at least 0.05 mm and not more than 0.5 mm in the aforementioned fourth or fifth embodiment. When structuring the reaction chamber in this manner, heat transmission efficiency from outside the vessel with respect to the reaction chamber is rendered excellent, whereby the sealing means is properly melted by heating in PCR, and PCR is properly performed.

While paraffin has been employed as the sealing means in the aforementioned fourth or fifth embodiment, the sealing means may be wax, grease, paraffin or wax. All of these are sealing means solid at ordinary temperature and entering liquid states at the time of first heating in PCR, whereby reliability of PCR is improved. Solid includes semisolid or glassy so far as the sealing means is capable of sealing. Further, the liquid state (melted state) may simply be a state where fluidity increases as compared with the solid state to be released from sealing.

While the melting point of the sealing means has been about 50° C. in the aforementioned fourth or fifth embodiment, the melting point (the temperature at which the sealing means shifts to the aforementioned melted state) is preferably 40° C. to 80° C., and more preferably 45° C. to 60° C. Further, the specific gravity is preferably smaller than that of water. Thus, the function/effect of being solid at ordinary temperature for isolating the reagents or the specimen and melted by first heating in PCR for inducing the reagents or the specimen to the lower reaction chamber can be more reliably attained.

While the reagent storing portion of the reagent cassette has been in a state storing no reagents in the aforementioned fourth or fifth embodiment, the same may be in a state where reagents are stored and sealed with sealing means at the time of selling, for example. When structuring the reagent cassette in this manner, reagents are previously stored and sealed in the reagent cassette, whereby the same can previously store desired quantities and types of reagents, and reliability and rapidity of PCR can be simply and stably improved by employing the same for a PCR vessel.

While the reaction chamber has been in a state storing no substance or storing only the specimen until PCR is started in the aforementioned fourth or fifth embodiment, the same may be deaerated to enter a decompressed state or a vacuum state by chemical or physical treatment.

The reaction chamber may be brought into a state filled with sealing means. When structuring the reaction chamber in this manner, the reaction chamber enters a state where air is discharged before PCR while the sealing means is so melted that the specimen and the reagents are stored through the reagent cassette at the time of PCR, whereby the specimen and the reagents can be easily guided to the reaction chamber, and reliability of PCR is improved.

While the heaters of the DNA detector have been made of silicone rubber in the aforementioned fourth or fifth embodiment, the same may be made of another material. For example, heaters made of a metal having high heat conductivity and previously provided with recesses can be listed. The heaters are so structured in this manner that durability against shape change at the time of repetitive use increases. Also in such a case, the recesses of the heaters can be formed to attain high adhesiveness to the surface of the reaction chamber in the case where the reaction chamber has the downwardly tapered conical shape.

While reagents have been stored in all reagent storing portions of the reagent cassette in the aforementioned fourth or fifth embodiment, there may be a reagent storing portion in which no reagent is stored at the time of use.

While the inner portion of the reagent cassette has been divided by the partition wall T-shaped in plan view to be provided with three reagent storing portions in the aforementioned fourth or fifth embodiment, the partition wall may have another shape, and the reagent storing portions may be in another number.

While the basic framework of the reagent cassette has had the cylindrical shape perpendicularly extending in the vertical direction in the aforementioned fourth or fifth embodiment, the basic framework (the sidewall) may have a tapered shape along the inner surface of the vessel body. When the inner surface of the vessel body and the basic framework have tapered shapes whose widths gradually narrow downward, the clearance between the inner surface of the vessel body and the outer surface of the reagent cassette can be narrowed, and the reagents or the specimen can be regulated not to leak into the clearance due to surface tension.

While the PCR vessel has been made of polypropylene in the aforementioned fourth or fifth embodiment, the same is preferably made of at least one type of material selected from a group consisting of polyethylene, polystyrene, polyethylene terephthalate, polyethylene naphthalate, polycarbonate, polyamide, acrylic, cyclic polyolefin and aromatic nylon. This is to make the whole PCR vessel including the reagent cassette not deformed or the like by heating in PCR.

While the specific DNA detector is employed in amplification of DNA and detection of the amplified DNA in the aforementioned fourth or fifth embodiment, another DNA amplifier or an apparatus performing detection of amplified DNA may be employed.

While only such a mode that the projecting portion of the reagent cassette is provided on the upper edge of the partition wall has been described in the aforementioned fifth embodiment, a downwardly convex projecting portion may similarly be provided also on the lower edge of the partition wall so that the reagent cassette is vertically symmetrical.

While the projecting portion of the reagent cassette has been described as if the same is made of a material different from that of the partition wall in the aforementioned fifth embodiment, the projecting portion and the partition wall may be made of the same material and integrally formed.

INDUSTRIAL AVAILABILITY

As hereinabove described, the PCR vessel, the PCR vessel containing a reagent, and the reagent cassette according to the present invention are suitable to be employed for a DNA detector for performing PCR, for example.

The invention claimed is:

1. A PCR (polymerase chain reaction) vessel (1, 41, 201, 255) comprising:
    a vessel body (11, 42, 211, 251) having a reaction chamber (12, 47, 212) storing and reacting a specimen (31, 264) and a reagent (32) at the time of a PCR on a bottom portion (14, 48, 213) thereof;
    a lid body (6, 43, 53, 206, 256, 303, 313) fittable with the vessel body; and
    a reagent cassette (16, 18, 44, 63, 64, 65, 66, 67, 68, 123, 124, 125, 126, 216, 259, 300, 310) stored in a portion of the vessel body between a lower surface (7, 45, 55, 207, 257) of the lid body and the reaction chamber, wherein
    the reagent cassette has at least one reagent storing portion (21, 57, 220) that seals the reagent with a sealing material (25, 61, 224) that is solid before the PCR, the sealing material being melted by heating in the PCR,
    an upwardly concave recess portion (10, 58, 208, 258, 305, 315), which stores at least a part of the specimen through contact with the specimen, is formed on the lower surface of the lid body,
    the regent cassette has a basic framework (24) that is not melted by heating in the PCR, and
    each of the at least one reagent storing portion is formed in the basic framework, the basic framework having a tubular shape opened on both ends in a vertical direction, said both ends being sealed with the sealing material.

2. The PCR vessel according to claim 1, wherein
    the at least one reagent storing portion in the reagent cassette includes a plurality of the reagent storing portions, and
    the reagent cassette is separated by a partition wall (22) into the plurality of reagent storing portions.

3. The PCR vessel according to claim 1, wherein
    a slit (23), extending in the vertical direction and communicating with the at least one reagent storing portion, is formed on a sidewall (24) of the basic framework.

4. The PCR vessel according to claim 1, wherein
    the reaction chamber is in the shape of a truncated quadrangular pyramid, and made of a transparent material.

5. The PCR vessel according to claim 1, wherein
    the vessel body, the lid body and the reagent cassette are set in such a dimensional relation that a clearance is formed between the lower surface of the lid body and the reagent cassette when the lid body fits with the vessel body.

6. The PCR vessel according to claim 1, wherein
    at least a part (46) of the inner surface of the vessel body inwardly projects toward the reagent cassette.

7. The PCR vessel according to claim 1, wherein
    a thickness of a vessel body wall is at least 0.05 mm and not more than 0.5 mm.

8. The PCR vessel according to claim 1, wherein
    the sealing material is wax, grease or paraffin.

9. The PCR vessel according to claim 1, wherein
    an inwardly concave recess portion (127, 128) is formed on at least one of an upper surface (17, 129, 130, 135) and a lower surface (131, 133) of the reagent cassette.

10. The PCR vessel according to claim 1, wherein
    an upwardly convex projecting portion (134, 136) is formed on an upper surface of the reagent cassette, and the projecting portion enters at least a part of the recess portion when the lid body fits with the vessel body.

11. The PCR vessel according to claim 1, wherein
    a downwardly convex portion is formed on a lower surface of the reagent cassette.

12. A PCR vessel containing a reagent employing the PCR vessel according to claim 1, wherein
    the reagent is stored in the at least one reagent storing portion and sealed by the sealing material in the reagent cassette.

13. The PCR vessel containing a reagent according to claim 12, wherein
    the reaction chamber is filled with the sealing material.

14. A PCR (polymerase chain reaction) vessel, comprising:
    a vessel body (11, 42, 211, 251) having a reaction chamber (12, 47, 212) storing and reacting a specimen (31, 264) and a reagent (32) at the time of a PCR on a bottom portion (14, 48, 213) thereof;
    a lid body (6, 43, 53, 206, 256, 303, 313) fittable with the vessel body; and
    a reagent cassette (16, 18, 44, 63, 64, 65, 66, 67, 68, 123, 124, 125, 126, 216, 259, 300, 310) stored in a portion of the vessel body between a lower surface (7, 45, 55, 207, 257) of the lid body and the reaction chamber, wherein
    the reagent cassette has a basic framework and at least one reagent storing portion (21, 57, 220) that seals the reagent with a sealing material (25, 61, 224) that is solid before the PCR, the sealing material being melted by heating in the PCR,
    an upwardly concave recess portion (10, 58, 208, 258, 305, 315), which stores at least a part of the specimen through contact with the specimen, is formed on the lower surface of the lid body,
    each of the at least one reagent storing portion is formed in the basic framework, the basic framework having a tubular shape opened on both ends in a vertical direction, said both ends being sealed with the sealing material, and
    an upper edge of the reaction chamber has a circular shape in a plan view for regulating the specimen or the reagent not to leak out of the reaction chamber at the time of the PCR.

15. The PCR vessel according to claim 14, wherein
    the reaction chamber has a downwardly tapered conical shape.

16. A PCR (polymerase chain reaction) vessel comprising:
    a vessel body (11, 42, 211, 251) having a reaction chamber (12, 47, 212) storing and reacting a specimen (31, 264) and a reagent (32) at the time of a PCR on a bottom portion (14, 48, 213) thereof;
    a lid body (6, 43, 53, 206, 256, 303, 313) fittable with the vessel body; and
    a reagent cassette (16, 18, 44, 63, 64, 65, 66, 67, 68, 123, 124, 125, 126, 216, 259, 300, 310) stored in a portion of the vessel body between a lower surface (7, 45, 55, 207, 257) of the lid body and the reaction chamber, wherein
    the reagent cassette has at least one reagent storing portion (21, 57, 220) that seals the reagent with a sealing material (25, 61, 224) that is solid before the PCR, the sealing material being melted by heating in the PCR,
    an upwardly concave recess portion (10, 58, 208, 258, 305, 315), which stores at least a part of the specimen through contact with the specimen, is formed on the lower surface of the lid body, the regent cassette has a basic framework (24), and each of the at least one reagent storing portion is formed in the basic framework, the basic framework having a tubular shape opened on both ends in a vertical direction, said both ends being sealed with the sealing material, and an upper edge of the reaction chamber is set to be positioned outward beyond the maximum movable region of an outer edge (226) of a lower end of the at least one reagent storing portion at the time of storage for regulating the specimen or the reagent not to leak out of the reaction chamber at the time of the PCR.

17. A PCR (polymerase chain reaction) vessel, comprising:

a vessel body (11, 42, 211, 251) having a reaction chamber (12, 47, 212) storing and reacting a specimen (31, 264) and a reagent (32) at the time of a PCR on a bottom portion (14, 48, 213) thereof;

a lid body (6, 43, 53, 206, 256, 303, 313) fittable with the vessel body; and a reagent cassette (16, 18, 44, 63, 64, 65, 66, 67, 68, 123, 124, 125, 126, 216, 259, 300, 310) stored in a portion of the vessel body between a lower surface (7, 45, 55, 207, 257) of the lid body and the reaction chamber, wherein the reagent cassette has a plurality of reagent storing portions (21, 57, 220) that seals the reagent with a sealing material (25, 61, 224) that is solid before the PCR, the sealing material being melted by heating in the PCR, an upwardly concave recess portion (10, 58, 208, 258, 305, 315), which stores at least a part of the specimen through contact with the specimen, is formed on the lower surface of the lid body, the regent cassette has a basic framework (24), and each of the plurality of storing portions is provided in the basic framework, the basic framework having a tubular shape opened on both ends in a vertical direction, said both ends being sealed with the sealing material, the reagent cassette is separated by a partition wall (22) into the plurality of reagent storing portions, and an upper edge of the partition wall is positioned downward beyond an upper edge (218, 261) of the basic framework, and the lower surface of the lid body is arranged between the upper edge of the partition wall and the upper edge of the basic framework in a state where the lid body and the reagent cassette are mounted on the vessel body.

18. The PCR vessel according to claim 17, wherein the upper edge of the partition wall further includes an upwardly convex projecting portion (265, 301, 311) projecting in the vertical direction in a portion of the upper edge inward beyond a lower edge of the recess portion of the lid body, and an upper edge (267, 301, 312) of the projecting portion is arranged on a vertical height position between the lower surface of the lid body and the upper edge of the basic framework and downward beyond an upper edge (218, 268, 316) of the recess portion.

* * * * *